US012385065B2

(12) United States Patent
Wilson et al.

(10) Patent No.: US 12,385,065 B2
(45) **Date of Patent: *Aug. 12, 2025**

(54) GENE THERAPY FOR TREATING CITRULLENEMIA

(71) Applicant: The Trustees of the University of Pennsylvania, Philadelphia, PA (US)

(72) Inventors: James M. Wilson, Philadelphia, PA (US); Jenny Agnes Sidrane, Phoenixville, PA (US); Lili Wang, Phoenixville, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 165 days.

This patent is subject to a terminal disclaimer.

(21) Appl. No.: 18/057,572

(22) Filed: Nov. 21, 2022

(65) Prior Publication Data

US 2023/0295660 A1 Sep. 21, 2023

Related U.S. Application Data

(63) Continuation of application No. 16/478,971, filed as application No. PCT/US2018/016413 on Feb. 1, 2018, now Pat. No. 11,535,866.

(60) Provisional application No. 62/453,424, filed on Feb. 1, 2017, provisional application No. 62/469,650, filed on Mar. 10, 2017.

(51) Int. Cl.

| | |
|---|---|
| ***A61K 48/00*** | (2006.01) |
| ***A61P 43/00*** | (2006.01) |
| ***C12N 15/86*** | (2006.01) |

(52) U.S. Cl.

CPC .............. *C12N 15/86* (2013.01); *A61P 43/00* (2018.01); *C12Y 603/04005* (2013.01); *A61K 48/00* (2013.01); *C12N 2750/14143* (2013.01); *C12N 2830/008* (2013.01); *C12N 2830/42* (2013.01)

(58) Field of Classification Search

CPC .... A61K 48/00; A61K 48/0058; C12N 15/86; C12N 2750/14143; C12N 2830/008; C12N 2830/42; C12Y 603/04005

See application file for complete search history.

(56) References Cited

U.S. PATENT DOCUMENTS

| | | | | |
|---|---|---|---|---|
| 11,535,866 | B2 * | 12/2022 | Wilson | C12N 9/93 |
| 2003/0147853 | A1 * | 8/2003 | McClelland | C07K 14/755 435/235.1 |
| 2003/0198620 | A1 * | 10/2003 | Ozawa | A61K 38/44 435/235.1 |
| 2004/0009151 | A1 * | 1/2004 | Kay | C12Y 304/21022 435/456 |
| 2006/0051333 | A1 * | 3/2006 | Arbetman | A61P 3/10 435/456 |
| 2006/0136184 | A1 | 6/2006 | Gustafsson et al. | |
| 2014/0032186 | A1 | 1/2014 | Gustafsson et al. | |
| 2015/0315612 | A1 | 11/2015 | Wilson et al. | |
| 2015/0376144 | A1 | 12/2015 | DeRosa et al. | |

FOREIGN PATENT DOCUMENTS

| | | |
|---|---|---|
| WO | WO 2003/052051 | 6/2003 |
| WO | WO 2005/033321 | 4/2005 |
| WO | WO 2011/126808 | 10/2011 |
| WO | WO 2013/049493 | 4/2013 |
| WO | WO 2015/012924 | 1/2015 |
| WO | WO 2017/015102 | 1/2017 |
| WO | WO 2017/100676 | 6/2017 |

OTHER PUBLICATIONS

Calcedo et al., Worldwide Epidemiology of Neutralizing Antibodies to Adeno-Associated Viruses. J Infect Dis. Feb. 1, 2009;199(3):381-90.

Castelhano-Carlos et al., Identification methods in newborn C57BL/6 mice: a developmental and behavioural evaluation. Lab Anim. Apr. 2010;44(2):88-103.

Chandler et al., Liver-directed adeno-associated virus serotype 8 gene transfer rescues a lethal murine model of citrullinemia type 1. Gene Ther. Dec. 2013;20(12):1188-91. Epub Oct. 17, 2013.

Engel et al., Mutations and polymorphisms in the human argininosuccinate synthetase (ASS1) gene. Hum Mutat. Mar. 2009;30(3):300-7.

Gao et al., Adeno-associated viruses undergo substantial evolution in primates during natural infections. Proc Natl Acad Sci U S A. May 13, 2003;100(10):6081-6. Epub Apr. 25, 2003.

GenBank Accession: AF513852.1, Adeno-associated virus 8 nonstructural protein and capsid protein genes, complete cds, Sep. 5, 2002.

Grimm et al., Titration of AAV-2 particles via a novel capsid ELISA: packaging of genomes can limit production of recombinant AAV-2. Gene Ther. Jul. 1999;6(7):1322-30.

Kelly et al., Splicing of many human genes involves sites embedded within introns. Nucleic Acids Res. May 19, 2015;43(9):4721-32. Epub Apr. 20, 2015.

Kobayashi et al. Messenger RNA coding for argininosuccinate synthetase in citrullinemia. Am J Hum Genet. May 1986;38(5):667-80.

Kok et al., Adeno-associated virus-mediated rescue of neonatal lethality in argininosuccinate synthetase-deficient mice. Mol Ther. Oct. 2013;21(10):1823-31. doi: 10.1038/mt.2013.139. Epub Jul. 2, 2013.

(Continued)

*Primary Examiner* — Kevin K Hill

(74) *Attorney, Agent, or Firm* — Howson & Howson LLP; Colleen M. Schaller

(57) ABSTRACT

Compositions and regimens useful in treating type I citrullenemia are provided. The compositions include recombinant adeno-associated virus (rAAV) with a transthyretin enhancer and promoter driving expression of a human Argininosuccinate Synthase 1 (ASS1).

20 Claims, 18 Drawing Sheets

Specification includes a Sequence Listing.

(56) References Cited

OTHER PUBLICATIONS

Lock et al., Absolute determination of single-stranded and self-complementary adeno-associated viral vector genome titers by droplet digital PCR. Hum Gene Ther Methods. Apr. 2014;25(2):115-25. Epub Feb. 14, 2014.

Miyatake et al., Transcriptional targeting of herpes simplex virus for cell-specific replication. J Virol. Jul. 1997;71(7):5124-32.

NCBI Reference Sequence: YP_077180.1, capsid protein [Adeno-associated virus—8], Mar. 11, 2010.

Saheki et al., Qualitative and quantitative abnormalities of argininosuccinate synthetase in citrullinemia. Clin Chim Acta. Feb. 5, 1981;109(3):325-35.

Sandig et al., HBV-derived promoters direct liver-specific expression of an adenovirally transduced LDL receptor gene. Gene Ther. Nov. 1996;3(11):1002-9.

Shepelev and Fedorov. Advances in the Exon-Intron Database. Brief Bioinform. Jun. 2006;7(2):178-85. Epub Mar. 9, 2006.

Sommer et al., Quantification of adeno-associated virus particles and empty capsids by optical density measurement. Mol Ther. Jan. 2003;7(1):122-8.

Thompson et al., A comprehensive comparison of multiple sequence alignments, Nucleic Acids Res. Jul. 1, 1999;27(13):2682-90.

Wobus et al., Monoclonal antibodies against the adeno-associated virus type 2 (AAV-2) capsid: epitope mapping and identification of capsid domains involved in AAV-2-cell interaction and neutralization of AAV-2 infection. J Virol. Oct. 2000;74(19):9281-93.

Wu et al., Effect of genome size on AAV vector packaging. Mol Ther. Jan. 2010;18(1):80-6. Epub Nov. 10, 2009.

Wu et al., Optimization of self-complementary AAV vectors for liver-directed expression results in sustained correction of hemophilia B at low vector dose. Mol Ther. Feb. 2008;16(2):280-9. Epub Dec. 4, 2007.

Search Report and Written Opinion in International Patent Application No. PCT/US18/16413, mailed Oct. 4, 2018.

Requirement for Election/Restriction in U.S. Appl. No. 16/478,971, issued Sep. 3, 2021.

Applicant's Response to Requirement for Election/Restriction in U.S. Appl. No. 16/478,971, filed Jan. 3, 2022.

Non-Final Rejection in U.S. Appl. No. 16/478,971, issued Mar. 4, 2022.

Applicant's Response to Non-Final Rejection in U.S. Appl. No. 16/478,971, filed Jul. 28, 2022.

Notice of Allowance in U.S. Appl. No. 16/478,971, issued Aug. 25, 2022.

* cited by examiner

MAP of pAAV8.ApoE.A1AT(full).IVS2.hASS1co.bGH.

GENE THERAPY FOR TREATING CITRULLENEMIA

CROSS-REFERENCE TO RELATED APPLICATIONS

This is a continuation of U.S. patent application Ser. No. 16/478,971, filed Jul. 18, 2019, which is a national stage application under 35 USC 371 of PCT/US2018/061413, filed Jan. 2, 2018, which claims the benefit under 35 USC 119 (e) of U.S. Provisional Patent Application No. 62/453,424, filed Feb. 1, 2017, and U.S. Provisional Patent Application No. 62/469,650, filed Mar. 10, 2017. Each of these applications is hereby incorporated by reference in its entirety.

INCORPORATION-BY-REFERENCE OF MATERIAL SUBMITTED IN ELECTRONIC FORM

Applicant hereby incorporates by reference the Sequence Listing material filed in electronic form herewith. This file is labeled "16-7938USC1.xml" (created Feb. 19, 2025 and 139,685 bytes in size).

1. BACKGROUND

The application relates to embodiments useful for a gene therapy for treating type I citrullenemia. Type I citrullenemia is an autosomal recessive disease caused by mutations in argininosuccinate synthase 1 (ASS1) enzyme that catalyzes the synthesis of argininosuccinate from citrulline and aspartate, resulting in citrullinemia and buildup of ammonia.

The clinical spectrum of Type I citrullenemia (CTLN1) ranges from severe neonatal onset form to milder late-onset forms. Owing to its relatively recent addition to the newborn screening panel, patients with type I citrullinemia will be identified early, allowing immediate implementation of treatment. However, despite this early identification of disease and treatment, some patients may progress. The untreated mortality rate in untreated classical CTLN1 is 100%, with most deaths occurring before 17 days of life.

Current treatment approaches for type I citrullenemia include dietary restriction (restriction of protein intake), medications (nitrogen scavenger therapy and carnitine), and arginine supplementation. Liver transplantation is curative for citrullinemia but transplant recipients are required to maintain a constant immune suppression regimen to prevent rejection. Liver directed AAV treatments for type I citrullenemia have been shown. See, e.g., Chandler et al, Liver-directed adeno-associated virus serotype 8 gene transfer rescues a lethal murine model of citrullinemia type 1, Gene Therapy (2013) 20, 1188-1191, which is incorporated herein by reference. However, liver-directed gene therapy did not fully correct the biochemical phenotype of systemic ASS1 deficiency; arginine levels plummeted in treated individuals of a murine model for CTLN1 (fold/fold) due to persistent renal deficiency. See also, Kok et al, Adeno-associated Virus-mediated Rescue of Neonatal Lethality in Argininosuccinate Synthase-deficient Mice, Molecular Therapy vol. 21 no. 10, 1823-1831 Oct. 2013, which is incorporated herein by reference.

What are needed are more effective treatments for type 1 citrullinemia.

2. SUMMARY

The embodiments described herein relate to an AAV gene therapy vector for delivering normal human Argininosuccinate Synthase 1 (ASS1) to a subject in need thereof, following intravenous administration of the vector resulting in long-term, perhaps 10 years or more, of clinically meaningful correction of Type I citrullenemia (CTLN1) (also sometimes called citrullinuria or ASS1 deficiency). The subject patient population is patients with moderate to severe Type I citrullenemia, including those with the acute neonatal form (the "classic" form), a milder late-onset form (the "non-classic" form), or the form in which women have onset of severe symptoms during pregnancy or post-partum. The intended vector dose is, in one embodiment, intended to deliver ASS1 which results in near normal citrulline, glutamine and ammonia plasma levels. However, even nominal reductions in citrulline, glutamine and ammonia levels are desirable, and a desirable endpoint. As reported by Quinonez and Thoene, Pagon R A, Adam M P, Ardinger H H, et al., editors. Seattle (WA): University of Washington, Seattle; 1993-2016 (incorporated herein by reference), elevation of either citrulline or ammonia above acceptable levels (ammonia >100 μmol/L or plasma citrulline >~100 μmol/L) is sufficient evidence to initiate treatment for CTLN1. In another embodiment, a neonatal diagnosis based on genetic testing is sufficient to initiate treatment.

In one aspect, this application provides the use of a replication deficient adeno-associated virus (AAV) to deliver a human Argininosuccinate Synthase 1 (hASS1) gene to liver cells of patients (human subjects) diagnosed with CTLN1. The recombinant AAV vector (rAAV) used for delivering the hASS1 gene ("rAAV.hASS1") should have a tropism for the liver (e.g., a rAAV bearing an AAV8 capsid), and the hASS1 transgene should be controlled by liver-specific expression control elements. In one embodiment, the expression control elements include one or more of the following: an enhancer; a promoter; an intron; a WPRE; and a polyA signal. Such elements are further described herein.

In one embodiment, the ASS1 protein sequence is shown in SEQ ID NO: 1. In one embodiment, the hASS1 coding sequence is shown in SEQ ID NO: 3. The coding sequence for hASS1 is, in one embodiment, codon optimized for expression in humans. Such sequence may share at least 80% identity to the native hASS1 coding sequence (SEQ ID NO: 3). In another embodiment, the hASS1 coding sequence is that shown in SEQ ID NO: 3.

In another aspect, provided herein is an aqueous suspension suitable for administration to a CTLN1 patient which includes the rAAV described herein. In some embodiments, the suspension includes an aqueous suspending liquid and about $1\times10^{12}$ to about $1\times10^{14}$ genome copies (GC) of the rAAV/mL. The suspension is, in one embodiment, suitable for intravenous injection. In other embodiment, the suspension further includes a surfactant, preservative, and/or buffer dissolved in the aqueous suspending liquid.

In another embodiment, provided herein is a method of treating a patient having CTLN1 with an rAAV as described herein. In one embodiment, about $1\times10^{11}$ to about $3\times10^{13}$ genome copies (GC) of the rAAV/kg patient body weight are delivered the patient in an aqueous suspension.

3. BRIEF DESCRIPTION OF THE DRAWINGS

Figure 2A:
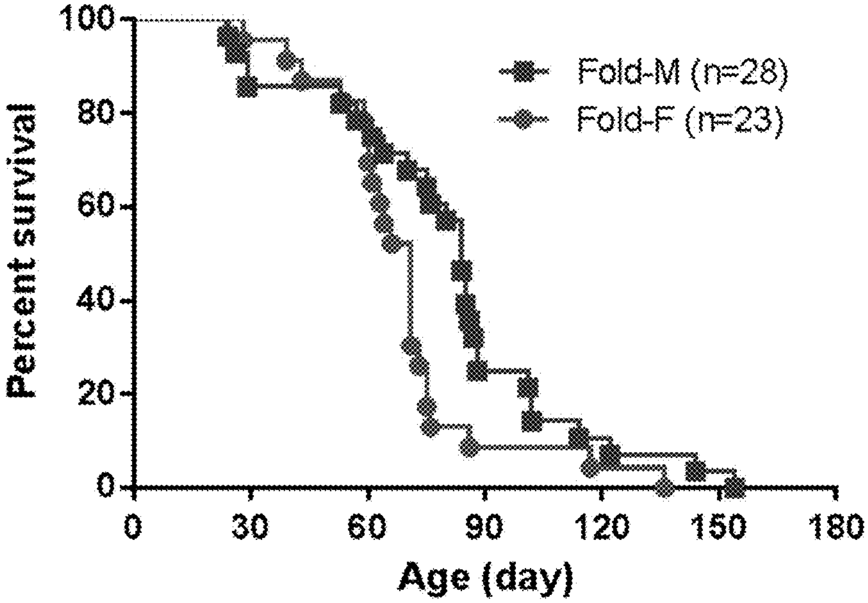
FIG. 2A is a survival curve of ASS1$^{fold/fold}$ mice as described in Example 2. Squares are male mice and circles are female mice.
Figure 2B:
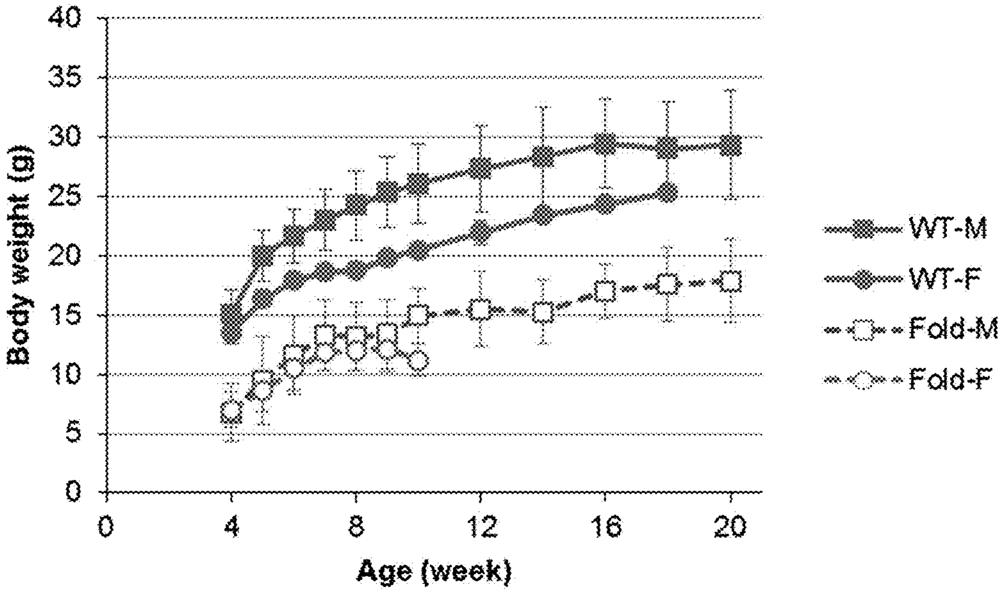

FIG. 2B is a line graph of body weights in both genders (M, male; F, female) of ASS1$^{fold/fold}$ mice (Fold). Wild-type littermates (WT) were provided as controls.

Figure 2C:
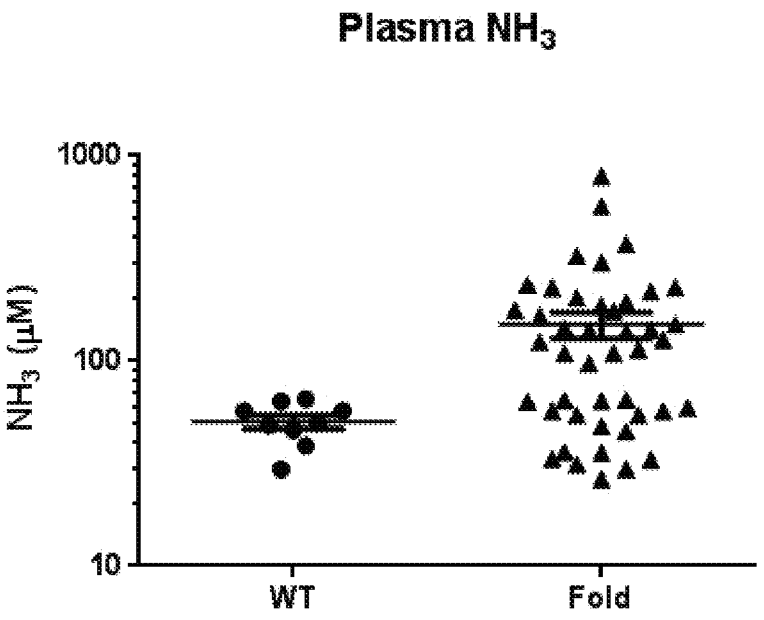

FIG. 2C is a graph showing elevated plasma $NH_3$ levels of ASS1$^{fold/fold}$ mice. Wild-type (WT) mice were provided as controls. Each circle or triangle indicates one sample. Mean±SEM is also plotted. Mann Whitney test was performed and the p value between indicated groups is shown in the figure.

Figure 2D:
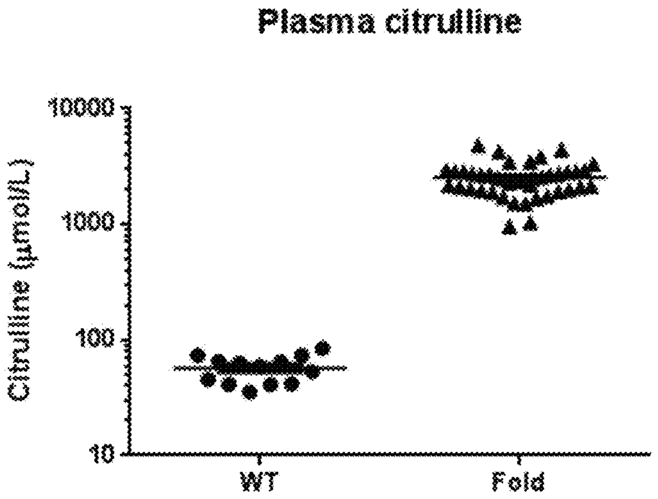

FIG. 2D is a graph showing elevated plasma citrulline levels of ASS1$^{fold/fold}$ mice. Wild-type (WT) mice were provided as controls. Each circle or triangle indicates one sample. Mean±SEM is also plotted. Mann Whitney test was performed and the p value between indicated groups is shown in the figure.

Figure 2E:
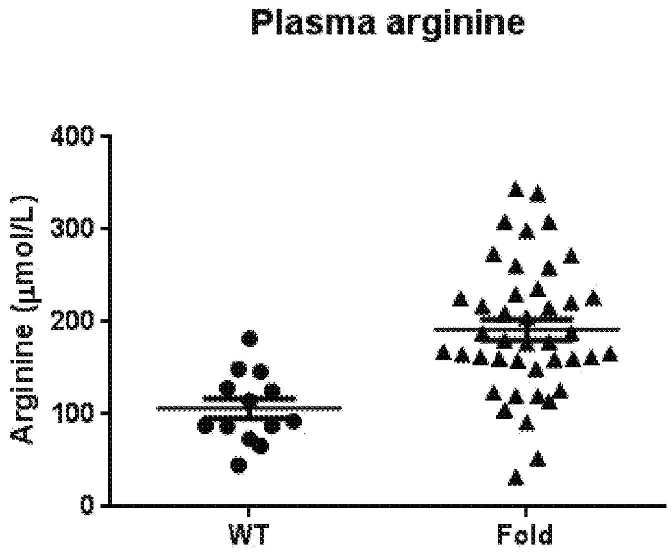

FIG. 2E is a graph showing elevated plasma arginine levels of ASS1$^{fold/fold}$ mice. Wild-type (WT) mice were provided as controls. Each circle or triangle indicates one sample. Mean±SEM is also plotted. Mann Whitney test was performed and the p value between indicated groups is shown in the figure.

Figure 2F:
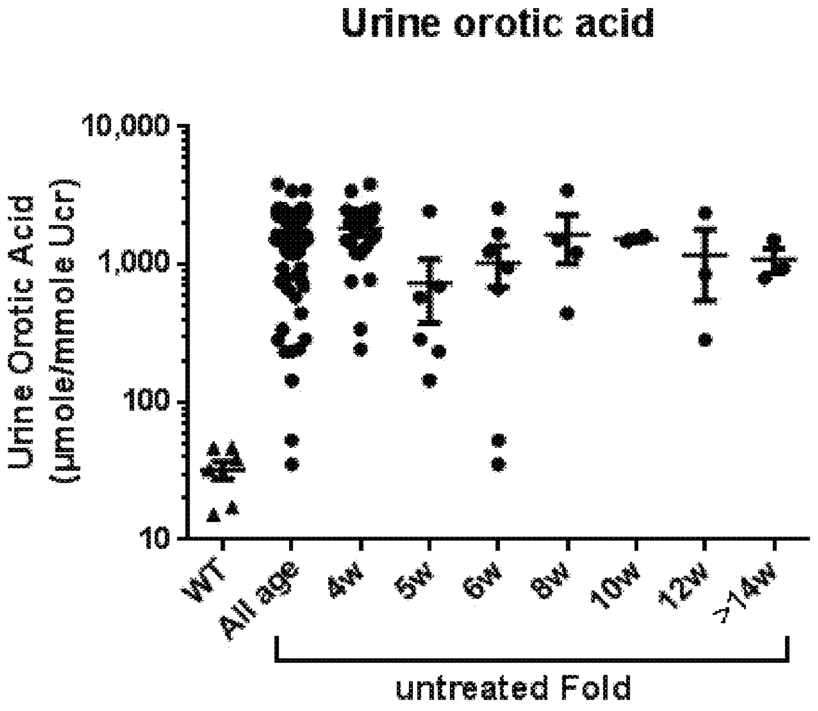

FIG. 2F is a graph showing elevated urine orotic acid levels of ASS1$^{fold/fold}$ mice at all age, or at the age of 4 weeks, 5 weeks, 6 weeks, 8 weeks, 10 weeks, 12 weeks and 14 weeks and older. Wild-type (WT) mice were provided as controls. Each dot indicates one sample. Mean±SEM is also plotted.

Figure 3A:
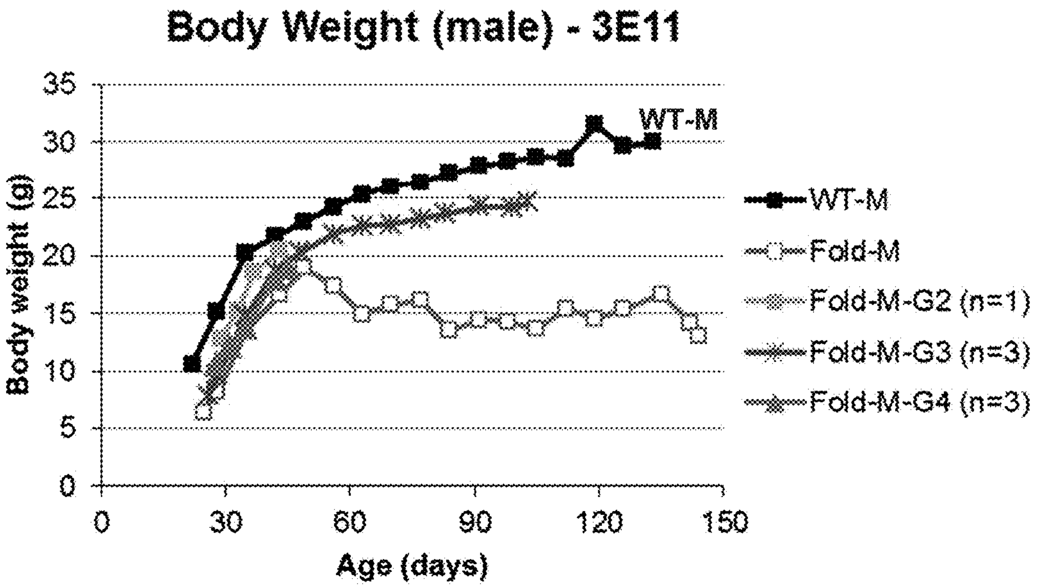

FIG. 3A is a line graph of body weights of male ASS1$^{fold/fold}$ mice injected intravenously at birth with $3\times10^{11}$ GC/pup of AAV8.TBG.PI.hASS1co. WPRE.bGH (Fold-M-G2, solid gray square, n=1) or AAV8.LSP.IVS2.hASS1co.bGH (Fold-M-G3, asterisk, n=3) or AAV8.TBG.PI.hASS1co.bGH (Fold-M-G4, triangle, n=3). Male ASS1$^{fold/fold}$ (Fold-M, open square) and wild-type (WT-M, solid black square) mice without treatment were provided as controls.

Figure 3B:
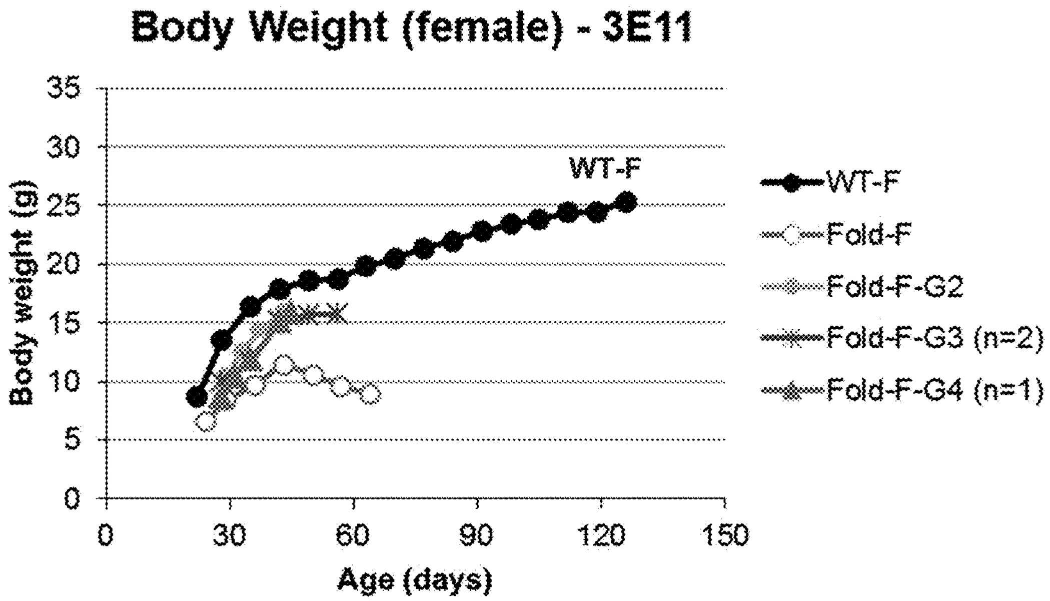

FIG. 3B is a line graph of body weights of female ASS1$^{fold/fold}$ mice injected intravenously at birth with $3\times10^{11}$ GC/pup of AAV8.TBG.PI.hASS1co. WPRE.bGH (Fold-F-G2, solid grey circle, n=1) or AAV8.LSP.IVS2.hASS1co.bGH (Fold-F-G3, asterisk, n=2) or AAV8.TBG.PI.hASS1co.bGH (Fold-F-G4, triangle, n=1). Female ASS1$^{fold/fold}$ (Fold-F, open circle) and wild-type (WT-F, solid black circle) mice without treatment were provided as controls.

Figure 3C:
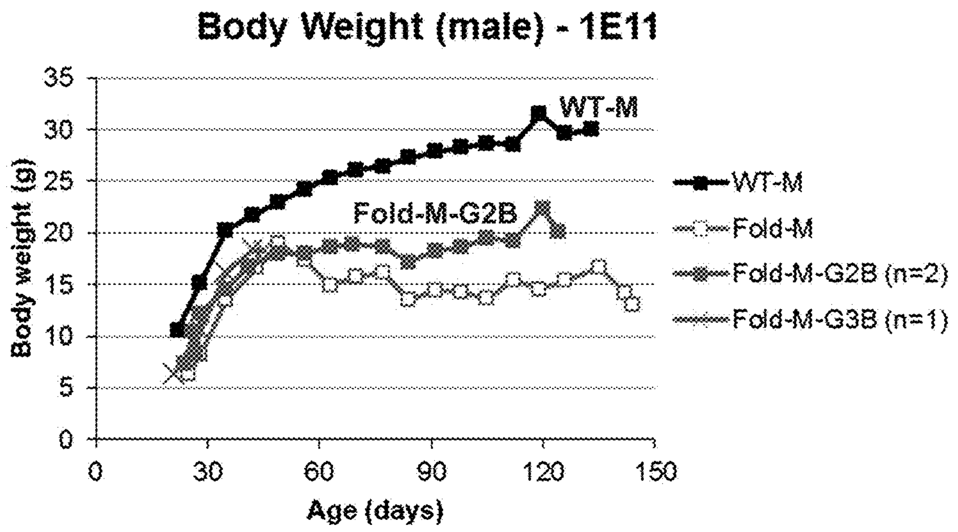

FIG. 3C is a line graph of body weights of male ASS1$^{fold/fold}$ mice injected intravenously at birth with $1\times10^{11}$ GC/pup of AAV8.TBG.PI.hASS1co.WPRE.bGH (Fold-M-G2, red, n=2) or AAV8.LSP.IVS2.hASS1co.bGH (Fold-M-G3, purple, n=1). Male ASS1$^{fold/fold}$ (Fold-M, blue) and wild-type (WT-M, black) mice without treatment were provided as controls.

Figure 3D:
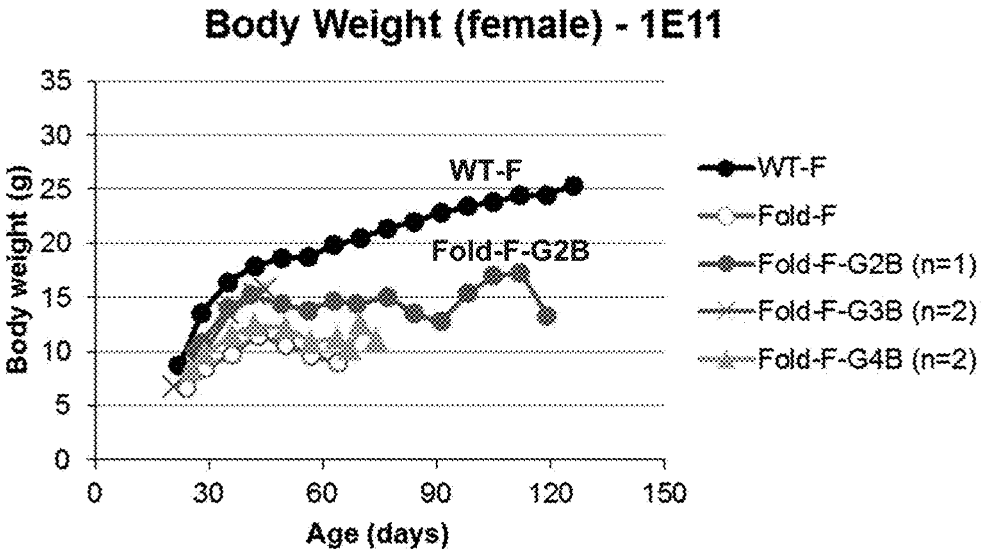

FIG. 3D is a line graph of body weights of female ASS1$^{fold/fold}$ mice injected intravenously at birth with $1\times10^{11}$ GC/pup of AAV8.TBG.PI.hASS1co.WPRE.bGH (Fold-F-G2, red, n=1) or AAV8.LSP.IVS2.hASS1co.bGH (Fold-F-G3, purple, n=2) or AAV8.TBG.PI.hASS1co.bGH (Fold-F-G4, green, n=2). Female ASS1$^{fold/fold}$ (Fold-F, blue) and wild-type (WT-F, black) mice without treatment were provided as controls.

Figure 3E:
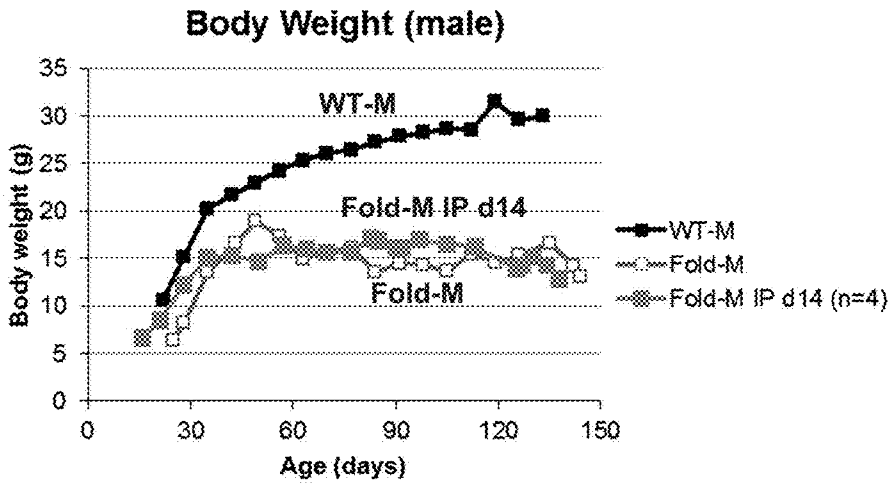

FIG. 3E is a line graph of body weights of male ASS1$^{fold/fold}$ mice injected intraperitoneal on postnatal day 14 with $1\times10^{11}$ GC/mouse of AAV8.TBG.PI.hASS1co.WPRE.bGH (Fold-M-IP d14, light blue, n=4). Male ASS1$^{fold/fold}$ (Fold-M, blue) and wild-type (WT-M, black) mice without treatment were provided as controls.

Figure 3F:
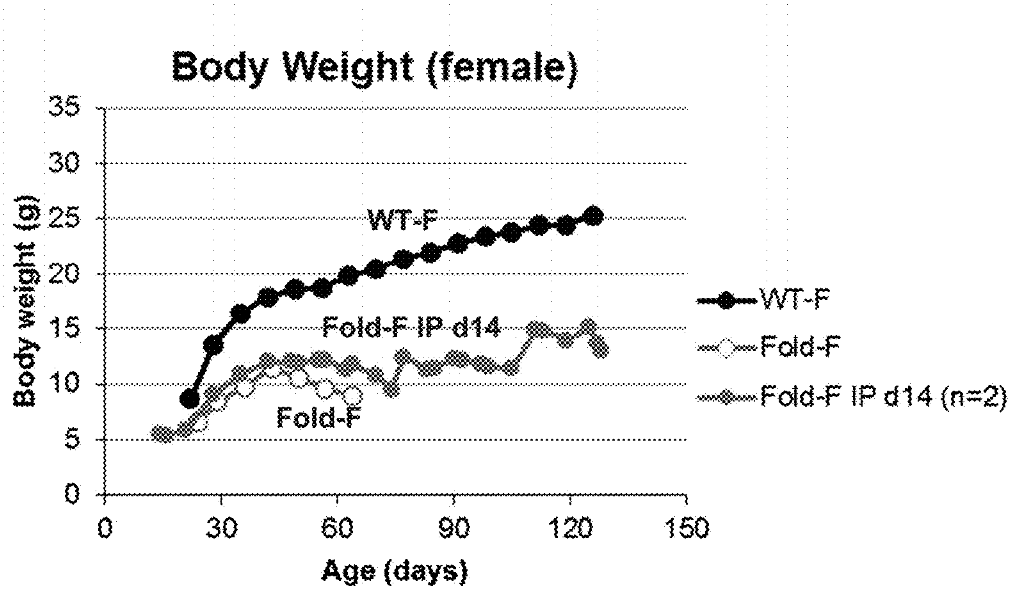

FIG. 3F is a line graph of body weights of female ASS1$^{fold/fold}$ mice injected intraperitoneal on postnatal day 14 with $1\times10^{11}$ GC/mouse of AAV8.TBG.PI.hASS1co. WPRE.bGH (Fold-F-IP d14, magenta, n=2). Female ASS1$^{fold/fold}$ (Fold-F, blue) and wild-type (WT-F, black) mice without treatment were provided as controls.

Figure 4A:
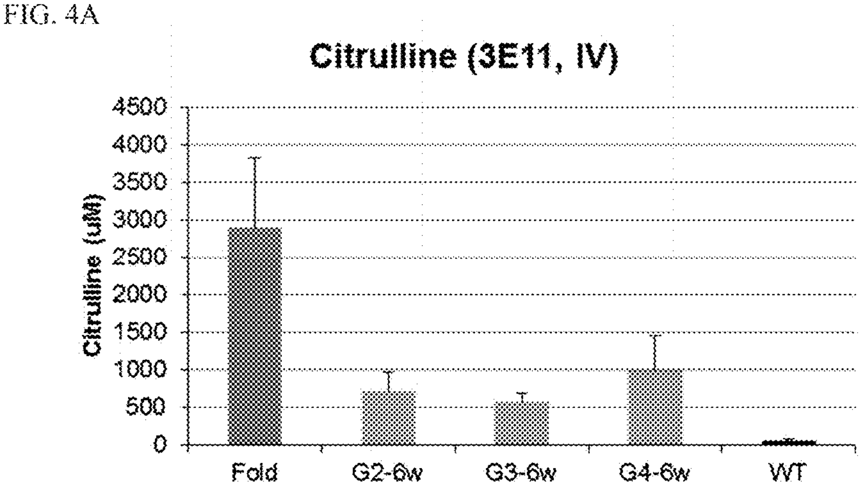

FIG. 4A is a bar graph of citrulline levels in the blood of ASS1$^{fold/fold}$ mice injected intravenously at birth with $3\times10^{11}$ GC/pup of AAV8.TBG.PI.hASS1co.WPRE.bGH (G2-6w) or AAV8.LSP.IVS2.hASS1co.bGH (G3-6w) or AAV8.TBG.PI.hASS1co.bGH (G4-6w). ASS1$^{fold/fold}$ (Fold) and wild-type (WT-M) mice without treatment were provided as controls.

Figure 4B:
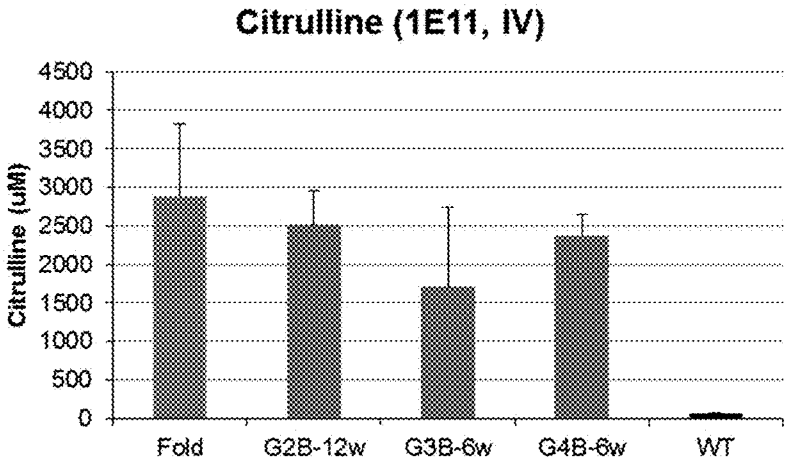

FIG. 4B is a bar graph of citrulline levels in the blood of ASS1$^{fold/fold}$ mice injected intravenously at birth with $1\times10^{11}$ GC/pup of AAV8.TBG.PI.hASS1co.WPRE.bGH (G2B-12w) or AAV8.LSP.IVS2.hASS1co.bGH (G3B-6w) or AAV8.TBG.PI.hASS1co.bGH (G4B-6w). ASS1$^{fold/fold}$ (Fold) and wild-type (WT-M) mice without treatment were provided as controls.

Figure 5A:
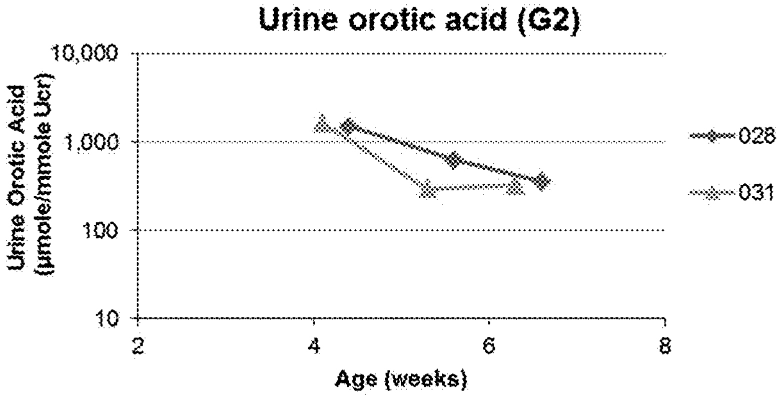

FIG. 5A is a line graph of urine orotic acid levels in ASS1$^{fold/fold}$ mice injected intravenously at birth with $3\times10^{11}$ GC/pup of AAV8.TBG.PI.hASS1co. WPRE.bGH. Data from mice with identification number 028 and 031 was acquired and plotted.

Figure 5B:
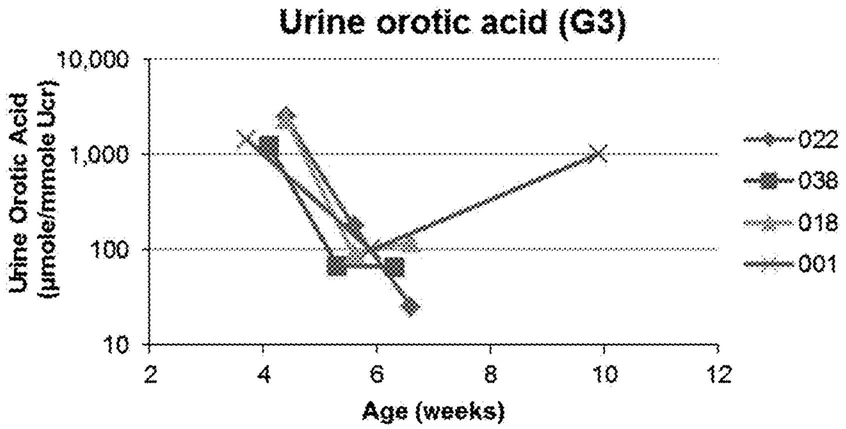

FIG. 5B is a line graph of urine orotic acid levels in ASS1$^{fold/fold}$ mice injected intravenously at birth with $3\times10^{11}$ GC/pup of AAV8.LSP.IVS2.hASS1co.bGH. Data from mice with identification number 022, 038, 018 and 001 was acquired and plotted.

Figure 5C:
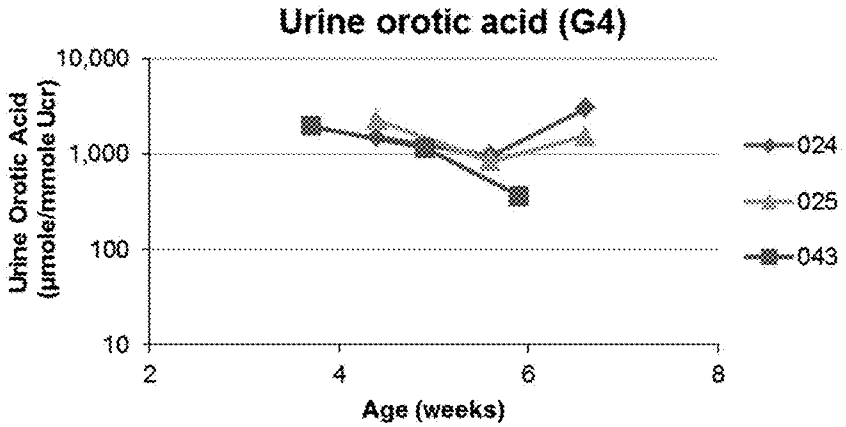

FIG. 5C is a line graph of urine orotic acid levels in ASS1$^{fold/fold}$ mice injected intravenously at birth with $3\times10^{11}$ GC/pup of AAV8.TBG.PI.hASS1co.bGH. Data from mice with identification number 024, 025 and 043 was acquired and plotted.

Figure 5D:
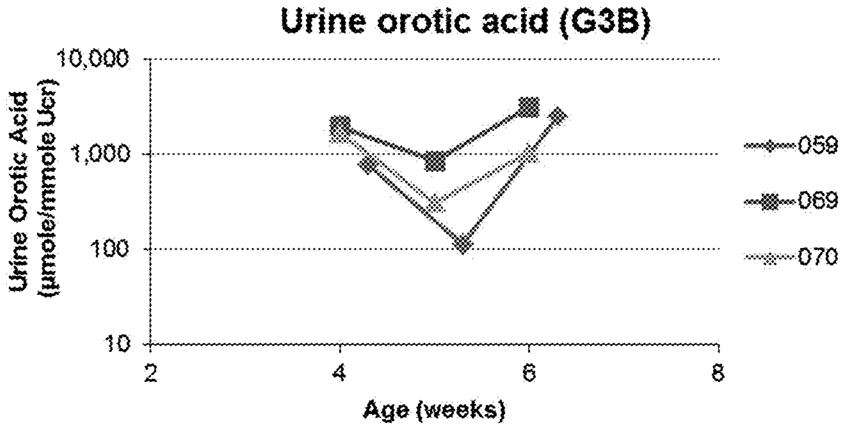

FIG. 5D is a line graph of urine orotic acid levels in ASS1$^{fold/fold}$ mice injected intravenously at birth with $1\times10^{11}$ GC/pup of AAV8.LSP.IVS2.hASS1co.bGH. Data from mice with identification number 059, 069 and 070 was acquired and plotted.

Figure 6A:
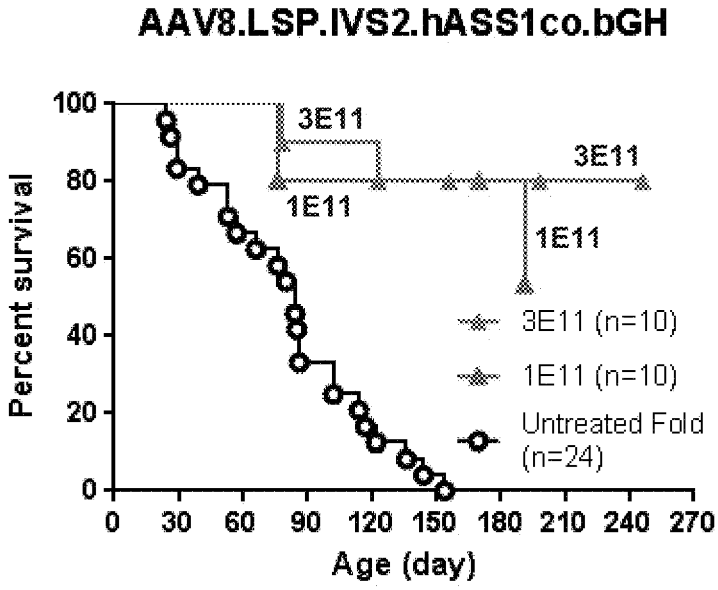

FIG. 6A is a survival curve of ASS1$^{fold/fold}$ mice demonstrating liver-directed gene therapy improves the survival of ASS1$^{fold/fold}$. Four-week old ASS1$^{fold/fold}$ (both males and females) received a single retro-orbital injection of AAV8.LSP.IVS.hASS1co.bGH vector at the dose of $3\times10^{11}$ GC/mouse (n=10) or $1\times10^{11}$ GC/mouse (n=10). Survival was monitored. Untreated ASS1$^{fold/fold}$ mice were provided as controls (n=24).

Figure 6B:
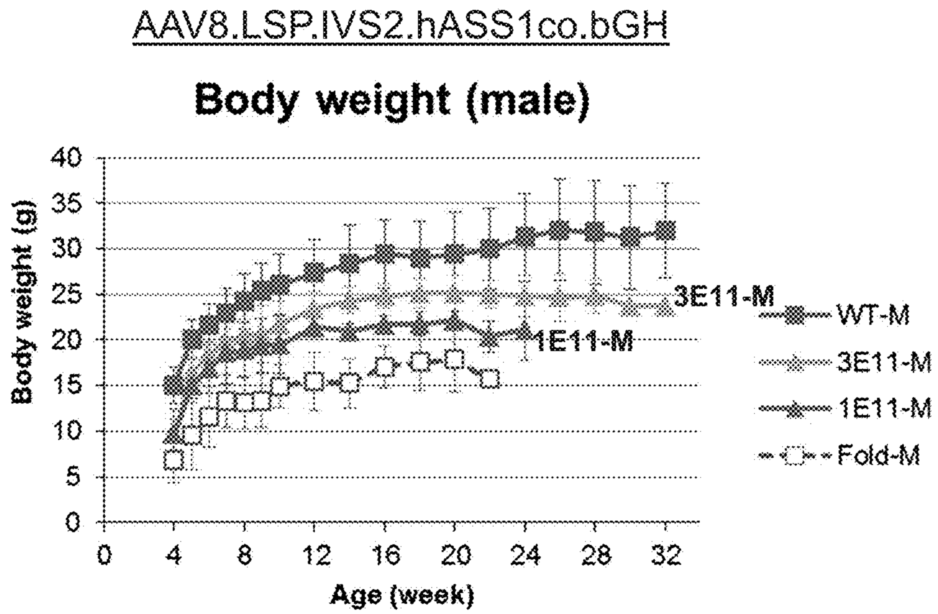

FIG. 6B is a line graph of body weights of male ASS1$^{fold/fold}$ mice demonstrating liver-directed gene therapy improves the body weight of ASS1$^{fold/fold}$ Four-week old ASS1$^{fold/fold}$ received a single retro-orbital injection of AAV8.LSP.IVS.hASS1co.bGH vector at the dose of $3\times10^{11}$ GC/mouse or $1\times10^{11}$ GC/mouse. Body weights were monitored. Gender-matched untreated ASS1$^{fold/fold}$ (Fold) and wild-type (WT) mice were provided as controls.

Figure 6C:
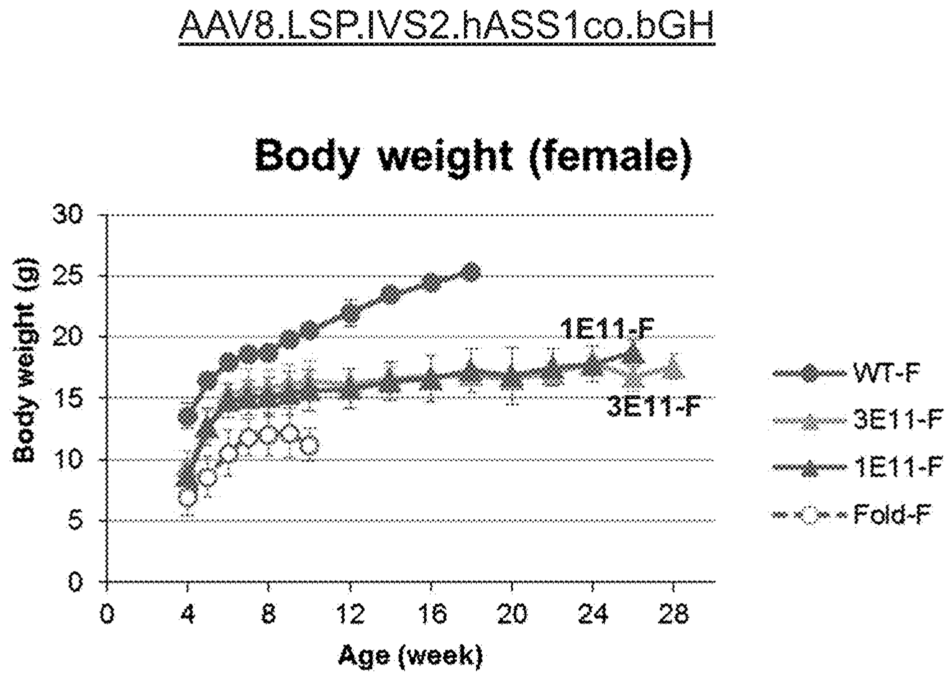

FIG. 6C is a line graph of body weights of female ASS1$^{fold/fold}$ mice demonstrating liver-directed gene therapy improves the body weight of ASS1$^{fold/fold}$ Four-week old ASS1$^{fold/fold}$ received a single retro-orbital injection of AAV8.LSP.IVS.hASS1co.bGH vector at the dose of $3\times10^{11}$ GC/mouse or $1\times10^{11}$ GC/mouse. Body weights were monitored. Gender-matched untreated ASS1$^{fold/fold}$ (Fold) and wild-type (WT) mice were provided as controls.

Figure 7A:
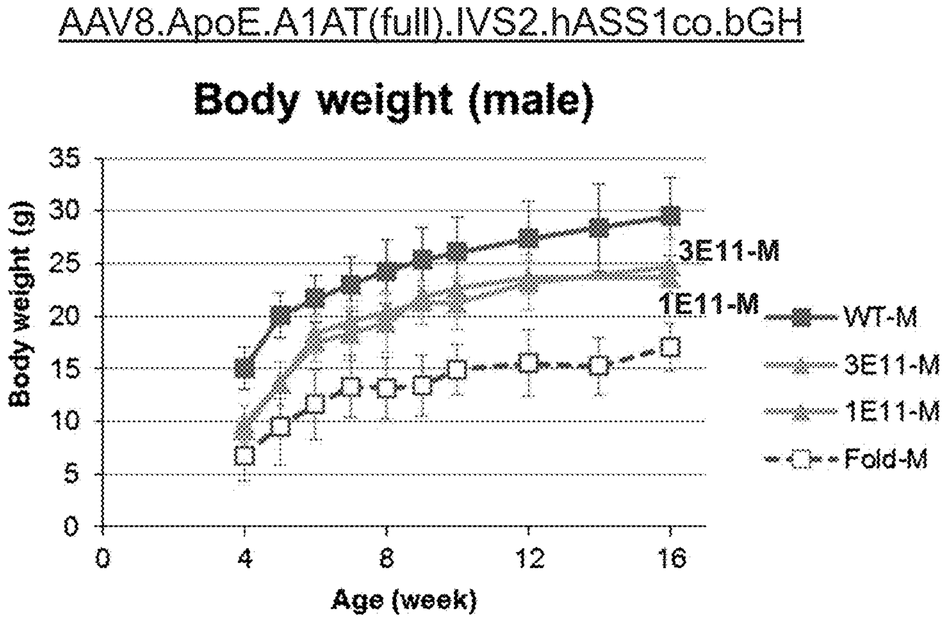

FIG. 7A is a line graph of body weights of male ASS1$^{fold/fold}$ mice demonstrating liver-directed gene therapy improves the body weight of ASS1$^{fold/fold}$ Four-week old ASS1$^{fold/fold}$ received a single retro-orbital injection of AAV8.ApoE.A1AT (full).IVS2.hASS1co.bGH vector at the dose of $3\times10^{11}$ GC/mouse or $1\times10^{11}$ GC/mouse. Body weights were monitored. Gender-matched untreated ASS1$^{fold/fold}$ (Fold) and wild-type (WT) mice were provided as controls.

Figure 7B:
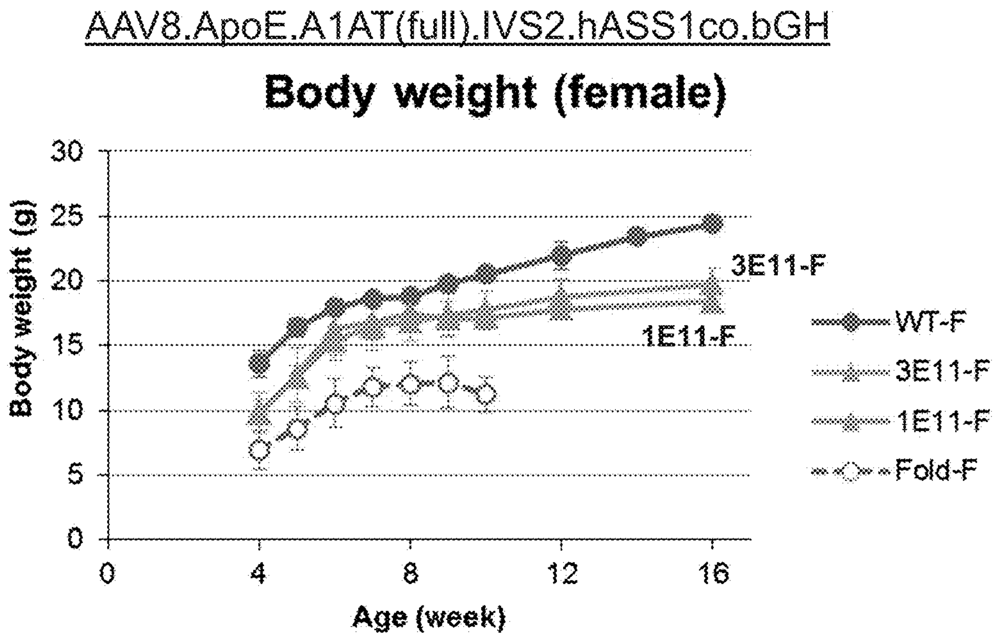

FIG. 7B is a line graph of body weights of female ASS1$^{fold/fold}$ mice demonstrating liver-directed gene therapy improves the body weight of ASS1$^{fold/fold}$ Four-week old ASS1$^{fold/fold}$ received a single retro-orbital injection of AAV8.ApoE.A1AT (full).IVS2.hASS1co.bGH vector at the dose of $3\times10^{11}$ GC/mouse or $1\times10^{11}$ GC/mouse. Body weights were monitored. Gender-matched untreated ASS1$^{fold/fold}$ (Fold) and wild-type (WT) mice were provided as controls.

Figure 8:
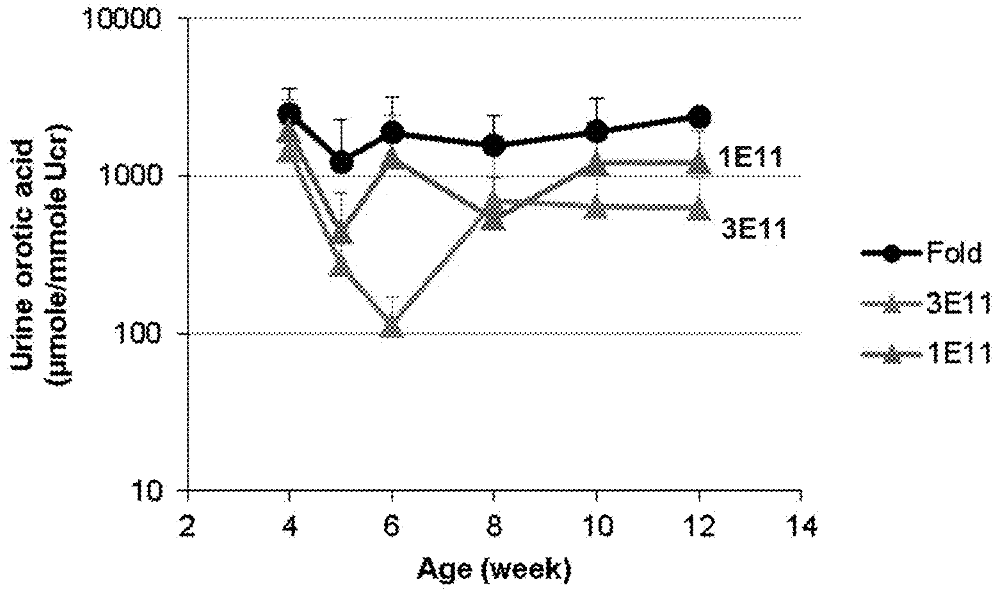

FIG. 8 is a line graph showing reduction of urine orotic acid in ASS1fold/fold following vector administration. Four-week old ASS1$^{fold/fold}$ received a single retro-orbital injection of AAV8.LSP.IVS2.hASS1co.bGH vector at the dose of $3\times10^{11}$ or $1\times10^{11}$ GC/mouse. ASS1$^{fold/fold}$ (Fold) mice were provided as controls.

Figure 9A:
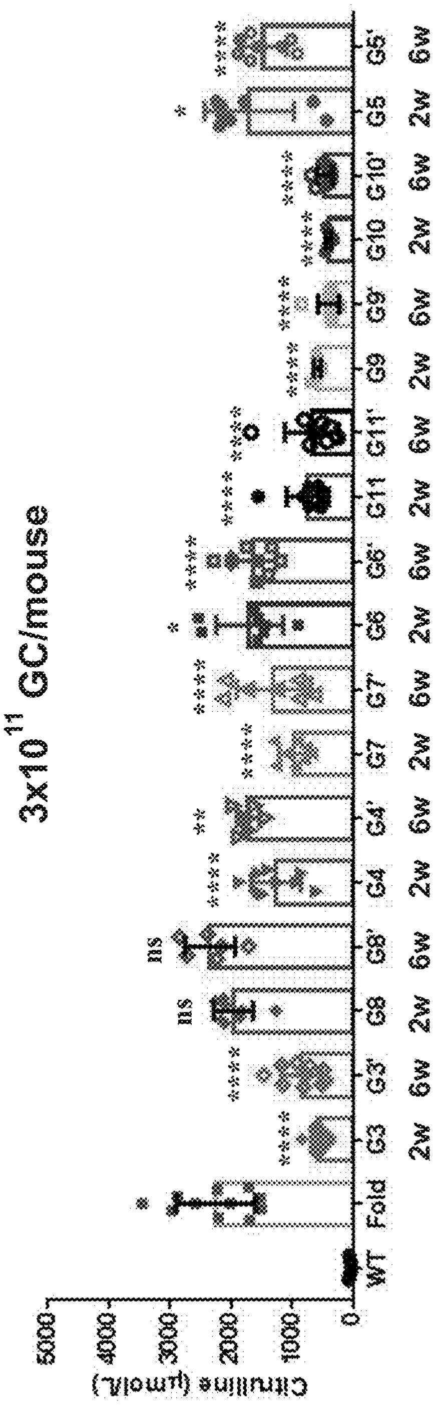
Figure 9B:
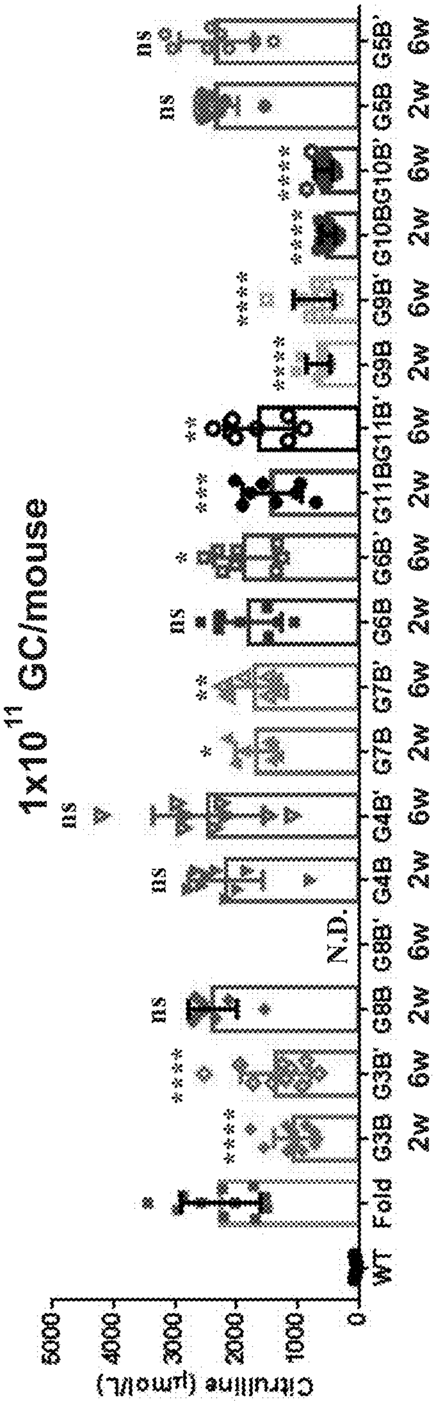

FIGS. 9A to 9B provide graphs showing citrulline levels in ASS1$^{fold/fold}$ mice at 2 weeks and 6 weeks post AAV8 vector administration. Four-week old ASS1fold/fold received a single retro-orbital injection of the indicated vector at the dose of $3\times10^{11}$ GC/mouse (FIG. 9A) or $1\times10^{11}$ GC/mouse (FIG. 9B). Code for each vector is listed in Table 1. Untreated ASS1$^{fold/fold}$ (Fold) and wild-type (WT) mice were provided as controls. Significant differences compared to untreated fold mice were calculated using one-way ANOVA Dunnett's multiple comparisons test. * $P<0.05$,  $P<0.01$, * $P<0.001$, **** $P<0.0001$.

Figure 10:
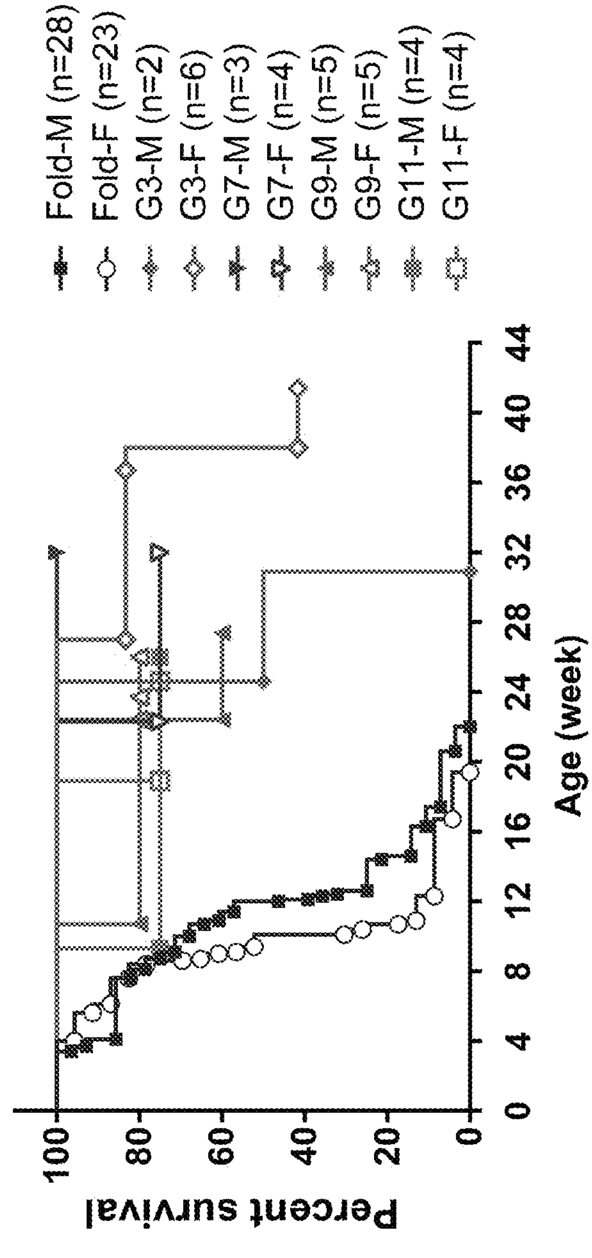

FIG. 10 is a graph showing percent survival in ASS1$^{fold/fold}$ mice. Four-week old ASS1$^{fold/fold}$ received a single retro-orbital injection of the indicated vector at the dose of $1\times10^{11}$ GC/mouse. Code for each vector is listed in Table 1. Untreated ASS1$^{fold/fold}$ (Fold) and wild-type (WT) mice were provided as controls.

Figure 11A:
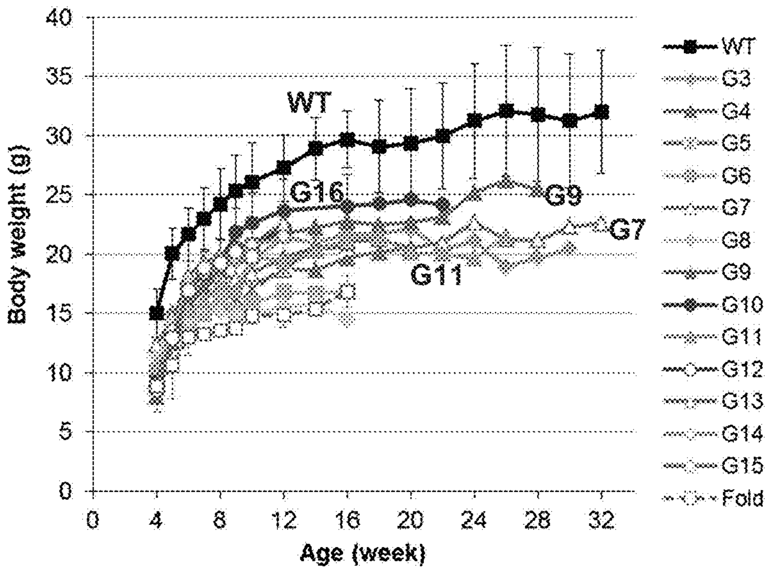

FIG. 11A is a graph showing body weight in male ASS1$^{fold/fold}$ mice. Four-week old ASS1$^{fold/fold}$ received a single retro-orbital injection of the indicated vector at the dose of $1\times10^{11}$ GC/mouse. Code for each vector is listed in Table 1. Untreated ASS1$^{fold/fold}$ (Fold) and wild-type (WT) mice were provided as controls. Liver-directed gene therapy improves the body weight of ASS1$^{fold/fold}$.

Figure 11B:
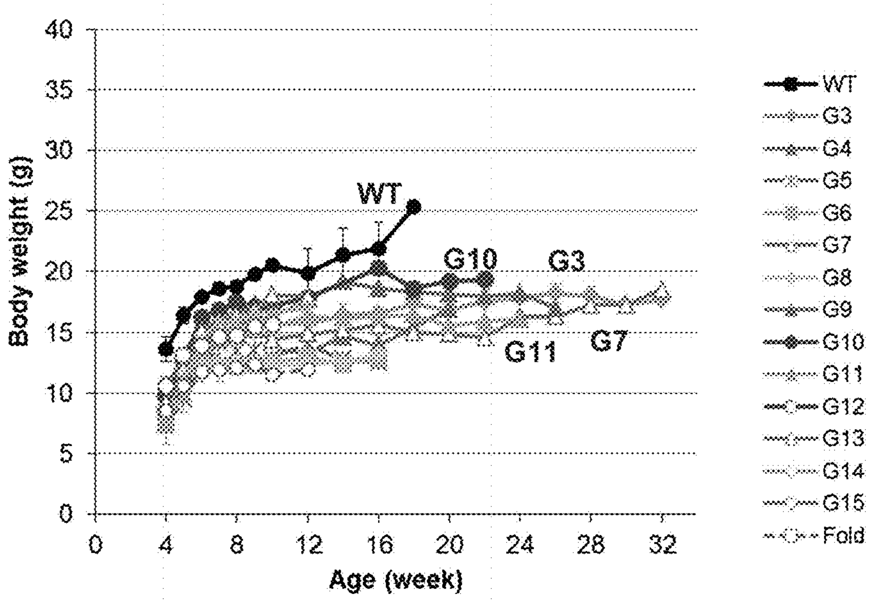

FIG. 11B is a graph showing body weight in female ASS1$^{fold/fold}$ mice. Four-week old ASS1$^{fold/fold}$ received a single retro-orbital injection of the indicated vector at the dose of $1\times10^{11}$ GC/mouse. Code for each vector is listed in Table 1. Untreated ASS1$^{fold/fold}$ (Fold) and wild-type (WT) mice were provided as controls. Liver-directed gene therapy improves the body weight of ASS1$^{fold/fold}$.

Figure 12A:
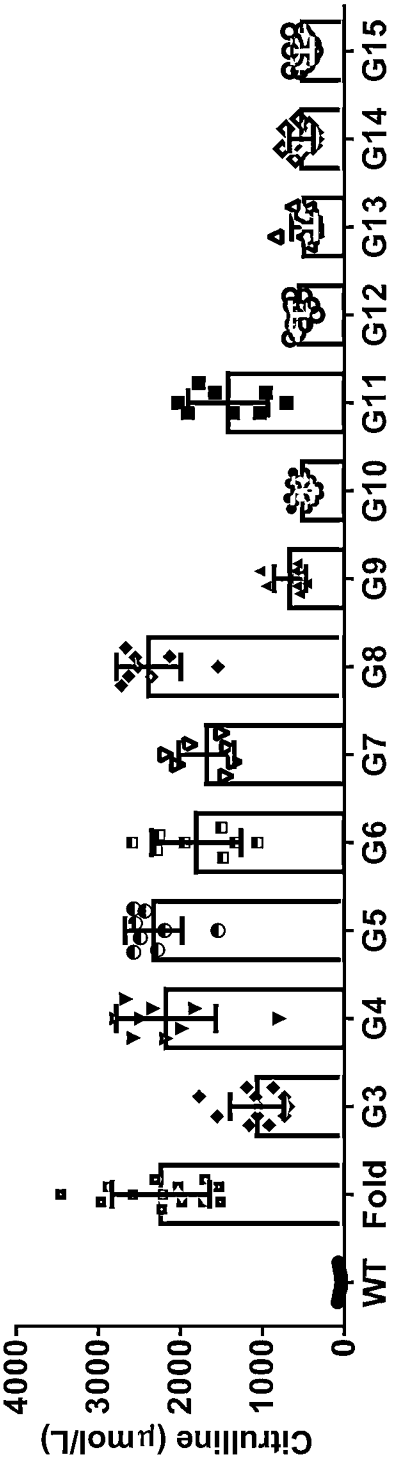
Figure 12B:
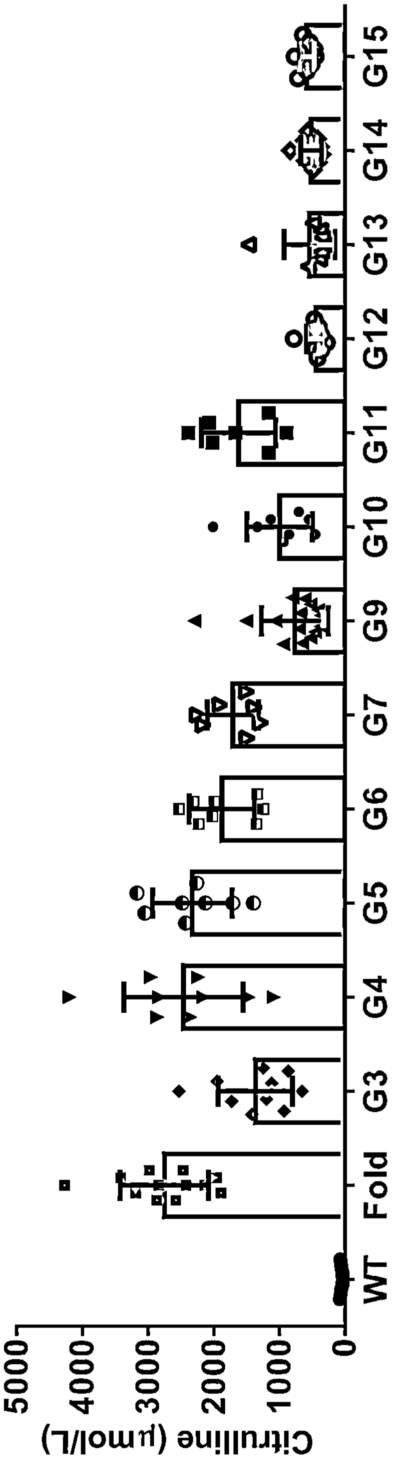

FIGS. 12A and 12B are graphs showing a reduction in plasma citrulline levels by AAV. Four-week old ASS1$^{fold/fold}$ (both males and females) received a single retro-orbital injection of AAV8-hASS1 vectors at the dose of $1\times10^{11}$ GC/mouse. Code for each vector is listed in Table 1. Plasma citrulline levels at 2 weeks (A) and 6 weeks (B) post vector administration.  $P<0.01$; ** $P<0.0001$, one-way ANOVA, Kruskal-Wallis test, compared to untreated fold mice.

Figure 13:
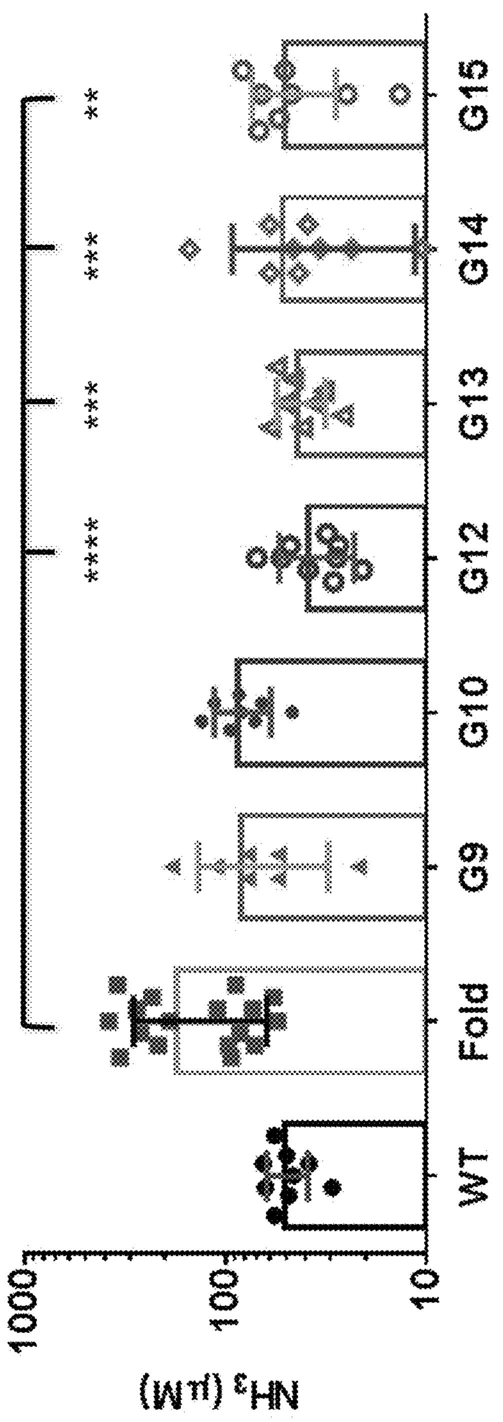

FIG. 13 is a graph showing a reduction in plasma citrulline levels by AAV. Four-week-old fold mice received a single retro orbital injection of AAV8-hASS1 vectors at the dose of $1.0\times10^{11}$ GC. Plasma $NH_3$ levels at 6 weeks post vector injection are shown here.  $P<0.01$; * $P<0.001$; **** $P<0.0001$, one-way ANOVA, Kruskal-Wallis test, compared to untreated fold mice.

4. DETAILED DESCRIPTION

The embodiments described in the application relate to the use of a replication deficient adeno-associated virus (AAV) to deliver a human Argininosuccinate Synthase 1 (hASS1) gene to liver cells of patients (human subjects) diagnosed with type 1 citrullenemia (CTLN1). The recombinant AAV vector (rAAV) used for delivering the hASS gene ("rAAV.hASS1") should have a tropism for the liver (e.g., an rAAV bearing an AAV8 capsid), and the hASS1 transgene should be controlled by liver-specific expression control elements. In one embodiment, the expression control elements include one or more of the following: an enhancer; a promoter; an intron; a WPRE; and a polyA signal. Such elements are further described herein.

As used herein, "AAV8 capsid" refers to the AAV8 capsid having the amino acid sequence of GenBank, accession: YP_077180.1, SEQ ID NO: 19, and/or an AAV8 capsid encoded by the nucleic acid sequence of GenBank: AF513852.1, nt 2121-4337, SEQ ID NO: 36, which sequences are incorporated by reference herein. Some variation from this encoded sequence is permitted, which may include sequences having about 99% identity to the referenced amino acid sequence in YP_077180.1 and WO 2003/052051 (which is incorporated herein by reference) (i.e., less than about 1% variation from the referenced sequence). Methods of generating the capsid, coding sequences therefore, and methods for production of rAAV viral vectors have been described. See, e.g., Gao, et al, Proc. Natl. Acad. Sci. U.S.A. 100 (10), 6081-6086 (2003) and US 2015/0315612.

As used herein, the term "NAb titer" a measurement of how much neutralizing antibody (e.g., anti-AAV Nab) is produced which neutralizes the physiologic effect of its targeted epitope (e.g., an AAV). Anti-AAV NAb titers may be measured as described in, e.g., Calcedo, R., et al., Worldwide Epidemiology of Neutralizing Antibodies to Adeno-Associated Viruses. Journal of Infectious Diseases, 2009. 199 (3): p. 381-390, which is incorporated by reference herein.

The terms "percent (%) identity", "sequence identity", "percent sequence identity", or "percent identical" in the context of amino acid sequences refers to the residues in the two sequences which are the same when aligned for correspondence. Percent identity may be readily determined for amino acid sequences over the full-length of a protein, polypeptide, about 32 amino acids, about 330 amino acids, or a peptide fragment thereof or the corresponding nucleic acid sequence coding sequencers. A suitable amino acid fragment may be at least about 8 amino acids in length, and may be up to about 700 amino acids. Generally, when referring to "identity", "homology", or "similarity" between two different sequences, "identity", "homology" or "similarity" is determined in reference to "aligned" sequences. "Aligned" sequences or "alignments" refer to multiple nucleic acid sequences or protein (amino acids) sequences, often containing corrections for missing or additional bases or amino acids as compared to a reference sequence. Alignments are performed using any of a variety of publicly or commercially available Multiple Sequence Alignment Programs. Sequence alignment programs are available for amino acid sequences, e.g., the "Clustal X", "MAP", "PIMA", "MSA", "BLOCKMAKER", "MEME", and "Match-Box" programs. Generally, any of these programs are used at default settings, although one of skill in the art can alter these settings as needed. Alternatively, one of skill in the art can utilize another algorithm or computer program which provides at least the level of identity or alignment as that provided by the referenced algorithms and programs. See, e.g., J. D. Thomson et al, Nucl. Acids. Res., "A comprehensive comparison of multiple sequence alignments", 27 (13): 2682-2690 (1999).

As used herein, the term "operably linked" refers to both expression control sequences that are contiguous with the gene of interest and expression control sequences that act in trans or at a distance to control the gene of interest.

A "replication-defective virus" or "viral vector" refers to a synthetic or artificial viral particle in which an expression cassette containing a gene of interest is packaged in a viral capsid or envelope, where any viral genomic sequences also packaged within the viral capsid or envelope are replication-deficient; i.e., they cannot generate progeny virions but retain the ability to infect target cells. In one embodiment, the genome of the viral vector does not include genes encoding the enzymes required to replicate (the genome can be engineered to be "gutless"-containing only the transgene of interest flanked by the signals required for amplification and packaging of the artificial genome), but these genes may be supplied during production. Therefore, it is deemed safe for use in gene therapy since replication and infection by progeny virions cannot occur except in the presence of the viral enzyme required for replication.

It is to be noted that the term "a" or "an" refers to one or more. As such, the terms "a" (or "an"), "one or more," and "at least one" are used interchangeably herein. The words "comprise", "comprises", and "comprising" are to be interpreted inclusively rather than exclusively. The words "consist", "consisting", and its variants, are to be interpreted exclusively, rather than inclusively. While various embodiments in the specification are presented using "comprising" language, under other circumstances, a related embodiment is also intended to be interpreted and described using "consisting of" or "consisting essentially of" language.

As used herein, the term "about" means a variability of 10% from the reference given, unless otherwise specified.

Unless defined otherwise in this specification, technical and scientific terms used herein have the same meaning as commonly understood by one of ordinary skill in the art and by reference to published texts, which provide one skilled in the art with a general guide to many of the terms used in the present application.

4.1 Gene Therapy Vectors

In one aspect, a recombinant adeno-associated virus (rAAV) vector carrying the human ASS1 gene is provided for use in gene therapy. The rAAV.hASS1 vector should have a tropism for the liver (e.g., a rAAV bearing an AAV8 capsid) and the hASS1 transgene should be controlled by liver-specific expression control elements. In another embodiment, the rAAV.hASS1 vector has a tropism for kidney. The vector is formulated in a buffer/carrier suitable for infusion in human subjects. The buffer/carrier should include a component that prevents the rAAV from sticking to the infusion tubing but does not interfere with the rAAV binding activity in vivo.

4.1.1. The rAAV.hASS Vector 4.1.1.1. The hASS1 Sequence

Citrullinemia type I (CTLN1) (also called "classic citrullinemia") results from deficiency of the enzyme argininosuccinate synthase 1 (ASS1), the third step in the urea cycle, in which citrulline is condensed with aspartate to form arginosuccinic acid.

Type I citrullinemia shows kinetically abnormal ASS1 in the liver, kidney, and cultured fibroblasts. In quantitative-type citrullinemia, low ASS1 is found in the liver but not in kidney or cultured skin fibroblasts. Residual enzyme in the liver has normal kinetic properties (Saheki et al., 1981). In a study of mRNA coding for ASS1, Kobayashi et al. (Am J. Hum. Genet., 38:667-80, 1986, which is incorporated herein by reference) found that patients with the quantitative type of citrullinemia had, as demonstrated in previous studies, about 10% of the control value of the enzyme in the liver but a normal level of mRNA. They concluded that in quantitative-type citrullinemia, the decrease in the enzyme protein is due either to increased degradation of the enzyme or to decreased or inhibited translation in the liver.

Although certain pathogenic variants are identified with some phenotypes, the phenotype cannot be predicted in all instances. Severe, classic citrullinemia type I typically results from 22 defined pathogenic variants (Engel et al, Human Mutation, 2009 March; 30 (3): 300-7, which is incorporated herein by reference). The pathogenic variant in exon 15, p.Gly390Arg, remains the most prevalent associated with the classic phenotype. Mild (i.e., late-onset) citrullinemia type I is associated with 12 pathogenic variants.

One goal of therapies described herein would provide functional ASS1 enzyme resulting in citrulline, glutamine, and/or ammonia levels less than 100 μmol/L. In another embodiment, any reduction in citrulline, glutamine, and/or ammonia levels is desirable. Other suitable clinical outcomes may include reduction in the use of scavenger, less restrictive diet or no need for liver transplant.

In one embodiment, the "subject" or "patient" is a mammalian subject having CTLN1 as described above. It is intended that a patient having CTLN1 of any severity is the intended subject. In addition, it is intended that a patient having any mutation in their native ASS1 gene is the intended subject.

In one embodiment, the hASS1 gene encodes the hASS1 protein shown in SEQ ID NO: 1. Thus, in one embodiment, the hASS1 transgene can include, but is not limited to, the sequence provided by SEQ ID NO:2 or SEQ ID NO: 3 which are provided in the attached Sequence Listing, which is incorporated by reference herein. SEQ ID NO: 3 provides the cDNA for native human ASS1. SEQ ID NO: 2 provides an engineered cDNA for human ASS1, which has been codon optimized for expression in humans (sometimes referred to herein as hASS1co). It is to be understood that reference to hASS1 herein may, in some embodiments, refer to the hASS1 native or codon optimized sequence. Alternatively or additionally, web-based or commercially available computer programs, as well as service based companies may be used to back translate the amino acid sequences to nucleic acid coding sequences, including both RNA and/or cDNA. See, e.g., backtranseq by EMBOSS,/www.ebi.ac.uk/Tools/st/; Gene Infinity (www.geneinfinity.org/sms-/sms_backtranslation.html); ExPasy (www.expasy.org/tools/). It is intended that all nucleic acids encoding the described hASS1 polypeptide sequences are encompassed, including nucleic acid sequences which have been optimized for expression in the desired target subject (e.g., by codon optimization).

In one embodiment, the nucleic acid sequence encoding hASS1 shares at least 95% identity with the native hASS1 coding sequence of SEQ ID NO: 3. In another embodiment, the nucleic acid sequence encoding hASS1 shares at least 90, 85, 80, 75, 70, or 65% identity with the native hASS1 coding sequence of SEQ ID NO: 3. In one embodiment, the nucleic acid sequence encoding hASS1 shares about 84% identity with the native hASS1 coding sequence of SEQ ID NO: 3. In one embodiment, the nucleic acid sequence encoding hASS1 is SEQ ID NO: 2.

In one embodiment, the hASS1 coding sequence is codon optimized for expression in the desirable subject species, e.g., humans. Codon-optimized coding regions can be designed by various different methods. This optimization may be performed using methods which are available online (e.g., GeneArt,), published methods, or a company which provides codon optimizing services, e.g., as DNA2.0 (Menlo Park, CA). One codon optimizing approach is described, e.g., in International Patent Publication No. WO 2015/012924, which is incorporated by reference herein. See also, e.g., US Patent Publication No. 2014/0032186 and US Patent Publication No. 2006/0136184. Suitably, the entire length of the open reading frame (ORF) for the product is modified. However, in some embodiments, only a fragment of the ORF may be altered (e.g., one or more of the individual immunoglobulin domains). By using one of these methods, one can apply the frequencies to any given polypeptide sequence, and produce a nucleic acid fragment of a codon-optimized coding region which encodes the polypeptide.

A number of options are available for performing the actual changes to the codons or for synthesizing the codon-optimized coding regions designed as described herein. Such modifications or synthesis can be performed using standard and routine molecular biological manipulations well known to those of ordinary skill in the art. In one approach, a series of complementary oligonucleotide pairs of 80-90 nucleotides each in length and spanning the length of the desired sequence are synthesized by standard methods. These oligonucleotide pairs are synthesized such that upon annealing, they form double stranded fragments of 80-90 base pairs, containing cohesive ends, e.g., each oligonucleotide in the pair is synthesized to extend 3, 4, 5, 6, 7, 8, 9, 10, or more bases beyond the region that is complementary to the other oligonucleotide in the pair. The single-stranded ends of each pair of oligonucleotides are designed to anneal with the single-stranded end of another pair of oligonucleotides. The oligonucleotide pairs are allowed to anneal, and approximately five to six of these double-stranded fragments are then allowed to anneal together via the cohesive single stranded ends, and then they ligated together and cloned into a standard bacterial cloning vector, for example, a TOPO® vector available from Thermo Fisher Scientific Inc. The construct is then sequenced by standard methods. Several of these constructs consisting of 5 to 6 fragments of 80 to 90 base pair fragments ligated together, i.e., fragments of about 500 base pairs, are prepared, such that the entire desired sequence is represented in a series of plasmid constructs. The inserts of these plasmids are then cut with appropriate restriction enzymes and ligated together to form the final construct. The final construct is then cloned into a standard bacterial cloning vector, and sequenced. Additional methods would be immediately apparent to the skilled artisan. In addition, gene synthesis is readily available commercially.

4.1.1.2. The rAAV Vector

Because ASS1 is natively expressed in the liver, it is desirable to use an AAV which shows tropism for liver. In one embodiment, the AAV supplying the capsid is AAV8. In another embodiment, the AAV supplying the capsid is AAVrh.10. In yet another embodiment, the AAV supplying the capsid is a Clade E AAV. Such AAV include rh.2; rh.10; rh. 25; bb.1, bb.2, pi.1, pi.2, pi.3, rh.38, rh.40, rh.43, rh.49, rh.50, rh.51, rh.52, rh.53, rh.57, rh.58, rh.61, rh.64, hu.6, hu. 17, hu.37, hu.39, hu.40, hu.41, hu.42, hu.66, and hu.67. This clade further includes modified rh. 2; modified rh. 58; and modified rh.64. See, WO 2005/033321, which is incorporated herein by reference. However, any of a number of rAAV vectors with liver tropism can be used. In another embodiment, the rAAV vector has a tropism for kidney.

In a specific embodiment described in the Examples, infra, the gene therapy vector is an AAV8 vector expressing an hASS1 transgene under control of a thyroxine binding globulin (TBG) promoter referred to as AAV8.TBG.PI.hASS1co. WPRE.bGH. In another embodiment, the WPRE is removed. In another embodiment, the gene therapy vector is an AAV8 vector expressing an hASS1 transgene under control of a A1AT promoter, with an ApoE1 enhancer referred to as AAV8.ApoE.A1AT (full) .IVS2.hASS1co.bGH. The external AAV vector component is a serotype 8, T=1 icosahedral capsid consisting of 60 copies of three AAV viral proteins, VP1, VP2, and VP3, at a ratio of 1:1:10. The capsid contains a single-stranded DNA rAAV vector genome.

In one embodiment, the rAAV.hASS1 genome contains an hASS1 transgene flanked by two AAV inverted terminal repeats (ITRs). In one embodiment, the hASS1 transgene includes one or more of an enhancer, promoter, an intron, a Woodchuck Hepatitis Virus (WHP) Posttranscriptional Regulatory Element (WPRE), an hASS1 coding sequence, and polyadenylation (polyA) signal. These control sequences are "operably linked" to the hASS1 gene sequences. The expression cassette containing these sequences may be engineered onto a plasmid which is used for production of a viral vector.

The ITRs are the genetic elements responsible for the replication and packaging of the genome during vector production and are the only viral cis elements required to generate rAAV. The minimal sequences required to package the expression cassette into an AAV viral particle are the AAV 5' and 3' ITRs, which may be of the same AAV origin as the capsid, or which of a different AAV origin (to produce an AAV pseudotype). In one embodiment, the ITR sequences from AAV2, or the deleted version thereof (ΔITR), are used. However, ITRs from other AAV sources may be selected. Where the source of the ITRs is from AAV2 and the AAV capsid is from another AAV source, the resulting vector may be termed pseudotyped. Typically, an expression cassette for an AAV vector comprises an AAV 5' ITR, the hASS1 coding sequences and any regulatory sequences, and an AAV 3' ITR. However, other configurations of these elements may be suitable. A shortened version of the 5' ITR, termed ΔITR, has been described in which the D-sequence and terminal resolution site (trs) are deleted. In other embodiments, the full-length AAV 5' and 3' ITRs are used. In one embodiment, the 5' ITR is that shown in SEQ ID NO: 16. In one embodiment, the 3' ITR is that shown in SEQ ID NO: 17.

Exemplary production plasmids to generate rAAVs are shown in SEQ ID NOs: 22 to 35. In one embodiment, provided herein is the plasmid of SEQ ID NO: 22. In another embodiment, provided herein is the plasmid of SEQ ID NO: 23. In another embodiment, provided herein is the plasmid of SEQ ID NO: 24. In another embodiment, provided herein is the plasmid of SEQ ID NO: 25. In another embodiment, provided herein is the plasmid of SEQ ID NO: 26. In another embodiment, provided herein is the plasmid of SEQ ID NO: 27. In another embodiment, provided herein is the plasmid of SEQ ID NO: 28. In another embodiment, provided herein is the plasmid of SEQ ID NO: 29. In another embodiment, provided herein is the plasmid of SEQ ID NO: 30. In another embodiment, provided herein is the plasmid of SEQ ID NO: 31. In another embodiment, provided herein is the plasmid of SEQ ID NO: 32. In another embodiment, provided herein is the plasmid of SEQ ID NO: 33. In another embodiment, provided herein is the plasmid of SEQ ID NO: 34. In another embodiment, provided herein is the plasmid of SEQ ID NO: 35.

Expression of the hASS1 coding sequence is driven from a liver-specific promoter. An illustrative plasmid and vector described herein uses the thyroxine binding globulin (TBG) promoter (SEQ ID NO: 9), or a modified version thereof. One modified version of the TBG promoter is a shortened version, termed TBG-S1. A modified thyroxine binding globulin (TBG-S1) promoter sequence is shown in SEQ ID NO: 8. Alternatively, other liver-specific promoters may be used such as the transthyretin promoter (TTR) (SEQ ID NO: 11). Another suitable promoter is the alpha 1 anti-trypsin (A1AT), or a modified version thereof (which sequence is shown in SEQ ID NO: 10). In one embodiment, the promoter is an A1AT promoter combined with an ApoE enhancer, sometimes referred to as ApoE.A1AT (full). In one embodiment, the sequence is shown in SEQ ID NO: 20. Another suitable promoter is the Liver specific promoter LSP (TH-binding globulin promoter/alpha1-microglobulin/bikunin enhancer) (SEQ ID NO: 21). Other suitable promoters include human albumin (Miyatake et al., J. Virol., 71:5124 32 (1997)), humAlb; and hepatitis B virus core promoter, (Sandig et al., Gene Ther., 3:1002-9 (1996). See, e.g., The Liver Specific Gene Promoter Database, Cold Spring Harbor, rulai.schl.edu/LSPD, which is incorporated by reference. Although less desired, other promoters, such as viral promoters, constitutive promoters, regulatable promoters [see, e.g., WO 2011/126808 and WO 2013/04943], or a promoter responsive to physiologic cues may be used may be utilized in the vectors described herein.

In one embodiment, the expression control sequences include one or more enhancer. In one embodiment, the En34 enhancer is included (34 bp core enhancer from the human apolipoprotein hepatic control region), which is shown in SEQ ID NO: 4. In another embodiment, the EnTTR (100 bp enhancer sequence from transthyretin) is included. Such sequence is shown in SEQ ID NO: 5. See, Wu et al, Molecular Therapy, 16 (2): 280-289, February 2008, which is incorporated herein by reference. In yet another embodiment, the α1-microglogulin/bikunin precursor enhancer is included. In yet another embodiment, the ABPS (shortened version of the 100 bp distal enhancer from the al-microglogulin/bikunin precursor [ABP] to 42 bp) enhancer is included. Such sequence is shown in SEQ ID NO: 6. In yet another embodiment, the ApoE enhancer is included. Such sequence is shown in SEQ ID NO: 7. In another embodiment, more than one enhancer is present. Such combination may include more than one copy of any of the enhancers described herein, and/or more than one type of enhancer.

In addition to a promoter, an expression cassette and/or a vector may contain other appropriate transcription initiation, termination, enhancer sequences, and efficient RNA processing signals. Such sequences include splicing and polyadenylation (polyA) signals; regulatory elements that enhance expression (i.e., WPRE (SEQ ID NO: 15); sequences that stabilize cytoplasmic mRNA; sequences that enhance translation efficiency (i.e., Kozak consensus sequence); sequences that enhance protein stability; and when desired, sequences that enhance secretion of the encoded product. In one embodiment, a polyadenylation (polyA) signal is included to mediate termination of hASS1 mRNA transcripts. Examples of other suitable polyA sequences include, e.g., bovine growth hormone (SEQ ID NO: 12), SV40, rabbit beta globin, and TK polyA, amongst others.

In one embodiment, the regulatory sequences are selected such that the total rAAV vector genome is about 2.0 to about 5.5 kilobases in size. In one embodiment, the regulatory sequences are selected such that the total rAAV vector genome is about 2.1, 2.3, 2.8, 3.1, 3.2, 3.3 or 4.0 kb in size. In one embodiment, it is desirable that the rAAV vector genome approximate the size of the native AAV genome. Thus, in one embodiment, the regulatory sequences are selected such that the total rAAV vector genome is about 4.7 kb in size. In another embodiment, the total rAAV vector genome is less about 5.2 kb in size. The size of the vector genome may be manipulated based on the size of the regulatory sequences including the promoter, enhancer, intron, poly A, etc. See, Wu et al, Mol Ther, January 2010 18 (1): 80-6, which is incorporated herein by reference.

Thus, in one embodiment, an intron is included in the vector. Suitable introns include the human beta globin IVS2 (SEQ ID NO: 13). See, Kelly et al, Nucleic Acids Research, 43 (9): 4721-32 (2015), which is incorporated herein by reference. Another suitable promoter includes the Promega chimeric intron (SEQ ID NO: 14). See, Almond, B. and Schenborn, E. T. A Comparison of pCI-neo Vector and pcDNA4/HisMax Vector. [Internet] 2000, which is incorporated herein by reference. Available from: www.promega-.com/resources/pubhub/enotes/a-comparison-of-pcineo-vector-and-pcdna4hismax-vector/). Another suitable intron includes the hFIX intron (SEQ ID NO: 18). Various introns suitable herein are known in the art and include, without limitation, those found at bpg.utoledo.edu/~afedorov/lab/eid.html, which is incorporated herein by reference. See also, Shepelev V., Fedorov A. Advances in the Exon-Intron Database. Briefings in Bioinformatics 2006, 7:178-185, which is incorporated herein by reference.

In one embodiment, the rAAV vector genome comprises a sequence selected from nt 1 to nt 3216 of SEQ ID NO: 22, nt 1 to nt 2331 of SEQ ID NO: 23, nt 1 to nt 3261 of SEQ ID NO: 24, nt 1 to nt 3325 of SEQ ID NO: 25, nt 1 to nt 2777 of SEQ ID NO: 26, nt 1 to nt 2777 of SEQ ID NO: 27, nt 1 to nt 3216 of SEQ ID NO: 28, nt 1 to nt 3066 of SEQ ID NO: 29, nt 1 to nt 2083 of SEQ ID NO: 30, nt 1 to nt 2121 of SEQ ID NO: 31, nt 1 to nt 3221 of SEQ ID NO: 32, nt 1 to nt 4040 of SEQ ID NO: 33, nt 1 to nt 2798 of SEQ ID NO: 34, or nt 1 to nt 3066 of SEQ ID NO: 35.

4.1.2. Compositions

In one embodiment, the rAAV.hASS1 virus is provided in a pharmaceutical composition which comprises an aqueous carrier, excipient, diluent or buffer. In one embodiment, the buffer is PBS. In a specific embodiment, the rAAV.hASS1 formulation is a suspension containing an effective amount of rAAV.hASS1 vector suspended in an aqueous solution containing 0.001% Pluronic F-68 in TMN200 (200 mM sodium chloride, 1 mM magnesium chloride, 20 mM Tris, pH 8.0). However, various suitable solutions are known including those which include one or more of: buffering saline, a surfactant, and a physiologically compatible salt or mixture of salts adjusted to an ionic strength equivalent to about 100 mM sodium chloride (NaCl) to about 250 mM sodium chloride, or a physiologically compatible salt adjusted to an equivalent ionic concentration.

For example, a suspension as provided herein may contain both NaCl and KCl. The pH may be in the range of 6.5 to 8.5, or 7 to 8.5, or 7.5 to 8. A suitable surfactant, or combination of surfactants, may be selected from among Poloxamers, i.e., nonionic triblock copolymers composed of a central hydrophobic chain of polyoxypropylene (poly (propylene oxide)) flanked by two hydrophilic chains of polyoxyethylene (poly(ethylene oxide)), SOLUTOL® HS 15 (Macrogol-15 Hydroxystearate), LABRASOL® (Polyoxy caprylic glyceride), polyoxy 10 oleyl ether, TWEEN® (polyoxyethylene sorbitan fatty acid esters), ethanol and polyethylene glycol. In one embodiment, the formulation contains a poloxamer. These copolymers are commonly named with the letter "P" (for poloxamer) followed by three digits: the first two digits x 100 give the approximate molecular mass of the polyoxypropylene core, and the last digit x 10 gives the percentage polyoxyethylene content. In one embodiment Poloxamer 188 is selected. The surfactant may be present in an amount up to about 0.0005% to about 0.001% of the suspension. In another embodiment, the vector is suspended in an aqueous solution containing 180 mM sodium chloride, 10 mM sodium phosphate, 0.001% Poloxamer 188, pH 7.3.

In one embodiment, the formulation is suitable for use in human subjects and is administered intravenously. In one embodiment, the formulation is delivered via a peripheral vein by bolus injection. In one embodiment, the formulation is delivered via a peripheral vein by infusion over about 10 minutes (+5 minutes). In one embodiment, the formulation is delivered via a peripheral vein by infusion over about 20 minutes (+5 minutes). In one embodiment, the formulation is delivered via a peripheral vein by infusion over about 30 minutes (+5 minutes). In one embodiment, the formulation is delivered via a peripheral vein by infusion over about 60 minutes (+5 minutes). In one embodiment, the formulation is delivered via a peripheral vein by infusion over about 90 minutes (+10 minutes). However, this time may be adjusted as needed or desired. Any suitable method or route can be used to administer an AAV-containing composition as described herein, and optionally, to co-administer other active drugs or therapies in conjunction with the AAV-mediated delivery of hASS1 described herein. Routes of administration include, for example, systemic, oral, inhalation, intranasal, intratracheal, intraarterial, intraocular, intravenous, intramuscular, subcutaneous, intradermal, and other parental routes of administration.

In one embodiment, the formulation may contain, e.g., about $1.0\times10^{11}$ genome copies per kilogram of patient body weight (GC/kg) to about $1\times10^{14}$ GC/kg, about 5 $\times10^{11}$ genome copies per kilogram of patient body weight (GC/kg) to about $3\times10^{13}$ GC/kg, or about $1\times10^{12}$ to about $1\times10^{14}$ GC/kg, as measured by oqPCR or digital droplet PCR (ddPCR) as described in, e.g., M. Lock et al, Hum Gene Ther Methods. 2014 April; 25 (2): 115-25. doi: 10.1089/hgtb.2013.131. Epub 2014 Feb. 14, which is incorporated herein by reference. In one embodiment, the rAAV.hASS formulation is a suspension containing at least $1\times10^{13}$ genome copies (GC)/mL, or greater, as measured by oqPCR or digital droplet PCR (ddPCR) as described in, e.g., M. Lock et al, supra.

In order to ensure that empty capsids are removed from the dose of AAV.hASS1 that is administered to patients, empty capsids are separated from vector particles during the vector purification process, e.g., using the method discussed herein. In one embodiment, the vector particles containing packaged genomes are purified from empty capsids using the process described in U.S. Patent Appln No. 62/322,098, filed on Apr. 13, 2016, and entitled "Scalable Purification Method for AAV8", which is incorporated by reference herein. Briefly, a two-step purification scheme is described which selectively captures and isolates the genome-containing rAAV vector particles from the clarified, concentrated supernatant of a rAAV production cell culture. The process utilizes an affinity capture method performed at a high salt concentration followed by an anion exchange resin method performed at high pH to provide rAAV vector particles which are substantially free of rAAV intermediates. Similar purification methods can be used for vectors having other capsids.

While any conventional manufacturing process can be utilized, the process described herein (and in U.S. Patent Appln No. 62/322,098) yields vector preparations wherein between 50 and 70% of the particles have a vector genome, i.e., 50 to 70% full particles. Thus for an exemplary dose of $1.6\times10^{12}$ GC/kg, and the total particle dose will be between $2.3\times10^{12}$ and $3\times10^{12}$ particles. In another embodiment, the proposed dose is one half log higher, or $5\times10^{12}$ GC/kg, and the total particle dose will be between $7.6\times10^{12}$ and $1.1\times10^{13}$ particles. In one embodiment, the formulation is be characterized by an rAAV stock having a ratio of "empty" to "full" of 1 or less, preferably less than 0.75, more preferably, 0.5, preferably less than 0.3.

A stock or preparation of rAAV8 particles (packaged genomes) is "substantially free" of AAV empty capsids (and other intermediates) when the rAAV8 particles in the stock are at least about 75% to about 100%, at least about 80%, at least about 85%, at least about 90%, at least about 95%, or at least 99% of the rAAV8 in the stock and "empty capsids" are less than about 1%, less than about 5%, less than about 10%, less than about 15% of the rAAV8 in the stock or preparation.

Generally, methods for assaying for empty capsids and AAV vector particles with packaged genomes have been known in the art. See, e.g., Grimm et al., *Gene Therapy* (1999) 6:1322-1330; Sommer et al., Molec. Ther. (2003) 7:122-128. To test for denatured capsid, the methods include subjecting the treated AAV stock to SDS-polyacrylamide gel electrophoresis, consisting of any gel capable of separating the three capsid proteins, for example, a gradient gel containing 3-8% Tris-acetate in the buffer, then running the gel until sample material is separated, and blotting the gel onto nylon or nitrocellulose membranes, preferably nylon. Anti-AAV capsid antibodies are then used as the primary antibodies that bind to denatured capsid proteins, preferably an anti-AAV capsid monoclonal antibody, most preferably the B1 anti-AAV-2 monoclonal antibody (Wobus et al., J. Virol. (2000) 74:9281-9293). A secondary antibody is then used, one that binds to the primary antibody and contains a means for detecting binding with the primary antibody, more preferably an anti-IgG antibody containing a detection molecule covalently bound to it, most preferably a sheep anti-mouse IgG antibody covalently linked to horseradish peroxidase. A method for detecting binding is used to semi-quantitatively determine binding between the primary and secondary antibodies, preferably a detection method capable of detecting radioactive isotope emissions, electromagnetic radiation, or colorimetric changes, most preferably a chemiluminescence detection kit. For example, for SDS-PAGE, samples from column fractions can be taken and heated in SDS-PAGE loading buffer containing reducing agent (e.g., DTT), and capsid proteins were resolved on pre-cast gradient polyacylamide gels (e.g., Novex). Silver staining may be performed using SilverXpress (Invitrogen, CA) according to the manufacturer's instructions. In one embodiment, the concentration of AAV vector genomes (vg) in column fractions can be measured by quantitative real time PCR (Q-PCR). Samples are diluted and digested with DNase I (or another suitable nuclease) to remove exogenous DNA. After inactivation of the nuclease, the samples are further diluted and amplified using primers and a TaqMan™ fluorogenic probe specific for the DNA sequence between the primers. The number of cycles required to reach a defined level of fluorescence (threshold cycle, Ct) is measured for each sample on an Applied Biosystems Prism 7700 Sequence Detection System. Plasmid DNA containing identical sequences to that contained in the AAV vector is employed to generate a standard curve in the Q-PCR reaction. The cycle threshold (Ct) values obtained from the samples are used to determine vector genome titer by normalizing it to the Ct value of the plasmid standard curve. End-point assays based on the digital PCR can also be used.

In one aspect, an optimized q-PCR method is provided herein which utilizes a broad spectrum serine protease, e.g., proteinase K (such as is commercially available from Qiagen). More particularly, the optimized qPCR genome titer assay is similar to a standard assay, except that after the DNase I digestion, samples are diluted with proteinase K buffer and treated with proteinase K followed by heat inactivation. Suitably samples are diluted with proteinase K buffer in an amount equal to the sample size. The proteinase K buffer may be concentrated to 2 fold or higher. Typically, proteinase K treatment is about 0.2 mg/mL, but may be varied from 0.1 mg/mL to about 1 mg/mL. The treatment step is generally conducted at about 55° C. for about 15 minutes, but may be performed at a lower temperature (e.g., about 37° C. to about 50° C.) over a longer time period (e.g., about 20 minutes to about 30 minutes), or a higher temperature (e.g., up to about 60° C.) for a shorter time period (e.g., about 5 to 10 minutes). Similarly, heat inactivation is generally at about 95° C. for about 15 minutes, but the temperature may be lowered (e.g., about 70 to about 90° C.) and the time extended (e.g., about 20 minutes to about 30 minutes). Samples are then diluted (e.g., 1000 fold) and subjected to TaqMan analysis as described in the standard assay.

Additionally, or alternatively, droplet digital PCR (ddPCR) may be used. For example, methods for determining single-stranded and self-complementary AAV vector genome titers by ddPCR have been described. See, e.g., M. Lock et al, Hu Gene Therapy Methods, Hum Gene Ther Methods. 2014 April; 25 (2): 115-25. doi: 10.1089/hgtb.2013.131. Epub 2014 Feb. 14.

4.2 Patient Population

As discussed above, a subject having CTLN1 of any severity is the intended recipient of the compositions and methods described herein.

Subjects may be permitted to continue their standard of care treatment(s) (e.g., protein restricted diet, and/or medications (including nitrogen scavenger therapy and carnitine)) prior to and concurrently with the gene therapy treatment at the discretion of their caring physician. In the alternative, the physician may prefer to stop standard of care therapies prior to administering the gene therapy treatment and, optionally, resume standard of care treatments as a co-therapy after administration of the gene therapy.

Desirable endpoints of the gene therapy regimen are an increase in ASS activity resulting in citrulline levels below about 100 μmol/L and/or ammonia levels below about 100 μmol/L. In another embodiment, any reduction in citrulline, glutamine, and/or ammonia levels is desirable. Other suitable clinical outcomes may include reduction in the use of scavenger, less restrictive diet or no need for liver transplant. In one embodiment, patients achieve reduced circulating ASS1 levels after treatment with rAAV.hASS1, alone and/or combined with the use of adjunctive treatments.

4.3. Dosing & Route of Administration

In one embodiment, the rAAV.hASS1 vector is delivered as a single dose per patient. In one embodiment, the subject is delivered the minimal effective dose (MED) (as determined by preclinical study described in the Examples herein). As used herein, MED refers to the rAAV.hASS1 dose required to achieve ASS1 activity resulting in citrulline levels below about 100 μmol/L and/or ammonia levels below about 100 μmol/L.

As is conventional, the vector titer is determined on the basis of the DNA content of the vector preparation. In one embodiment, quantitative PCR or optimized quantitative PCR as described in the Examples is used to determine the DNA content of the rAAV.hASS1 vector preparations. In one embodiment, digital droplet PCR as described in the Examples is used to determine the DNA content of the rAAV.hASS1 vector preparations. In one embodiment, the dosage is about $1\times10^{11}$ genome copies (GC)/kg body weight to about $1\times10^{13}$ GC/kg, inclusive of endpoints. In one embodiment, the dosage is $5\times10^{11}$ GC/kg. In another embodiment, the dosage is $5\times10^{12}$ GC/kg. In specific embodiments, the dose of rAAV.hASS1 administered to a patient is at least $5\times10^{11}$ GC/kg, $1\times10^{12}$ GC/kg, $1.5\times10^{12}$ GC/kg, $2.0\times10^{12}$ GC/kg, $2.5\times10^{12}$ GC/kg, $3.0\times10^{12}$ GC/kg, $3.5\times10^{12}$ GC/kg, $4.0\times10^{12}$ GC/kg, $4.5\times10^{12}$ GC/kg, $5.0\times10^{12}$ GC/kg, $5.5\times10^{12}$ GC/kg, $6.0\times10^{12}$ GC/kg, $6.5\times10^{12}$ GC/kg, $7.0\times10^{12}$ GC/kg, or $7.5\times10^{12}$ GC/kg. Also, the replication-defective virus compositions can be formulated in dosage units to contain an amount of replication-defective virus that is in the range of about $1.0\times10^{9}$ GC to about $1.0\times10^{15}$ GC. As used herein, the term "dosage" can refer to the total dosage delivered to the subject in the course of treatment, or the amount delivered in a single (of multiple) administration.

In some embodiments, rAAV.hASS1 is administered in combination with one or more therapies for the treatment of CTLN1, such as a low protein diet or administration nitrogen scavenger therapy or dialysis.

4.4. Measuring Clinical Objectives

Measurements of efficacy of treatment can be measured by transgene expression and activity as determined by ammonia or citrulline levels and/or ASS1 activity. Further assessment of efficacy can be determined by clinical assessment of dietary citrulline tolerance.

As used herein, the rAAV.hASS1 vector herein "functionally replaces" or "functionally supplements" the patients defective ASS1 with active ASS1 when the patient expresses a sufficient level of ASS1 to achieve ASS1 activity resulting in citrulline and/or ammonia levels less than about 100 μmol/L. In another embodiment, the rAAV.hASS1 vector functionally replaces or functionally supplements the patient's defective ASS1 when partial rescue is provided. This allows for treatment with a combination of scavengers and dietary control. In one embodiment, the treatment provides sufficient rescue such that liver transplantation is not required. In another embodiment, a reduction in the rate of complications such as viral diseases (e.g., flu) is desired.

5. EXAMPLES

The following examples are illustrative only and are not intended to limit the present invention.

EXAMPLE 1: AAV Vectors Containing hASS1

An exemplary gene therapy vector AAV8.TBG.PI.hASS1co. WPRE.bGH was constructed by an AAV8 vector bearing a codon-optimized human ASS1 cDNA (hASS1co) under the control of TBG, a hybrid promoter based on the human thyroid hormone-binding globulin promoter and microglobin/bikunin enhancer. The ASS1 expression cassette was flanked by AAV2 derived inverted terminal repeats (ITRs) and the expression was driven by a hybrid of the TBG enhancer/promoter and the Woodchuck Hepatitis Virus (WHP) posttranscriptional regulatory element (WPRE) as an enhancer. The transgene also included the Promega SV40 misc intron (PI) and a bovine growth hormone polyadenylation signal (bGH).

Another Exemplary Gene Therapy Vector

Figure 1:
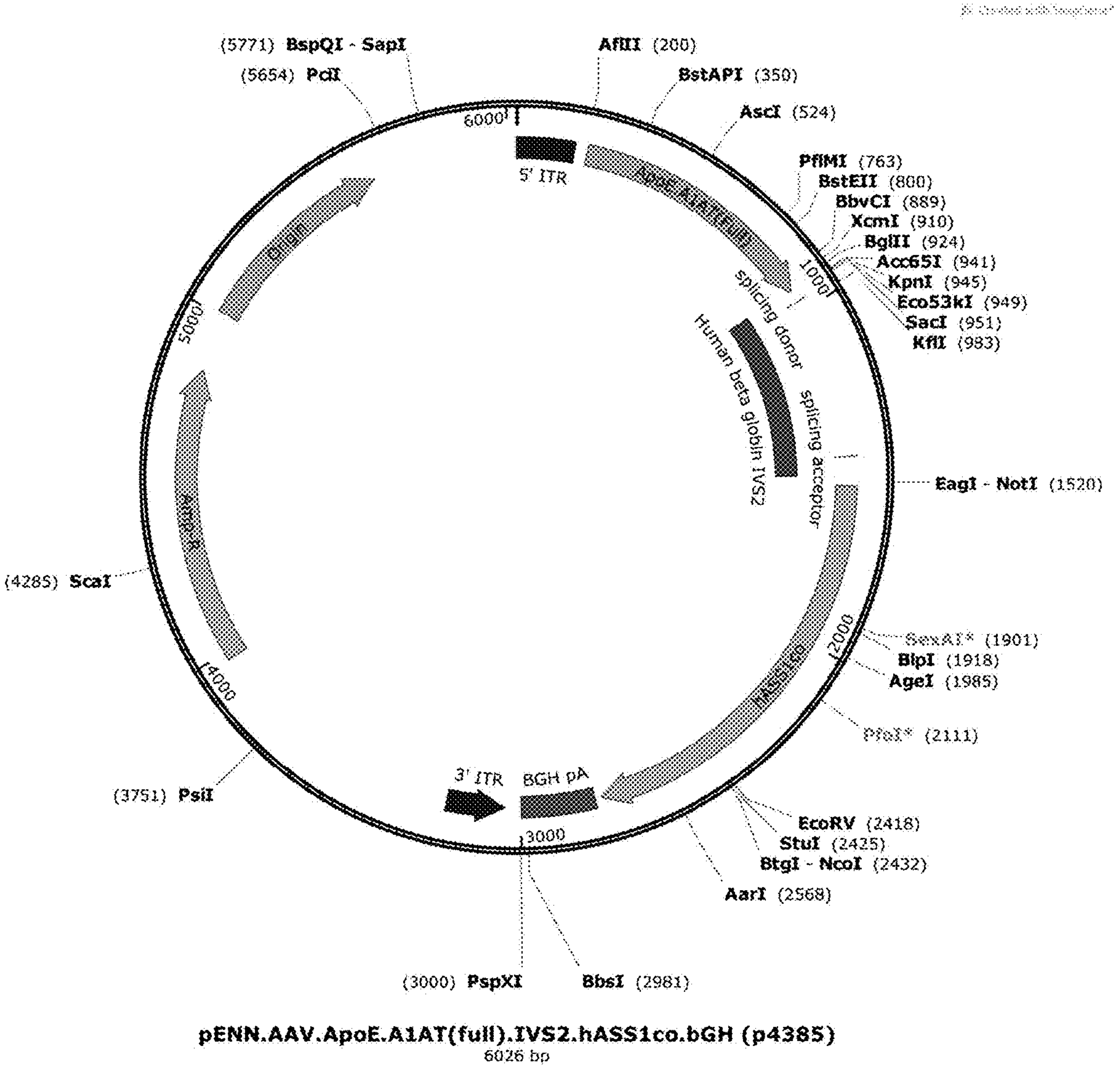
FIG. 1 is a schematic representation of AAV.hASS1co cis plasmid.

AAV8.ApoE.A1AT (full).IVS2.hASS1co.bGH was constructed by an AAV8 vector bearing a codon-optimized human ASS1 cDNA (hASS1co) under the control of A1AT promoter and a ApoE enhancer (FIG. 1). The ASS1 expression cassette was flanked by AAV2 derived inverted terminal repeats (ITRs) and the expression was driven by the ApoE.A1AT enhancer/promoter. The transgene also included the human beta globin IVS2 as an intron and a bovine growth hormone polyadenylation signal (bGH).

The vector AAV8.TBG.PI.hASS1co.bGH was constructed as described above without WPRE as an enhancer.

The AAV8.LSP.IVS2.hASS1co.bGH vector encodes a codon-optimized human ASS1 cDNA (hASS1co) under the control of a liver-specific promoter (LSP), with intervening sequence 2 (IVS2) and a bovine growth hormone polyadenylation signal (bGH).

The vector was prepared using conventional triple transfection techniques in 293 cells as described e.g., by Mizukami, Hiroaki, et al. *A Protocol for AAV vector production and purification*. Diss. Di-vision of Genetic Therapeutics, Center for MolecularMedicine, 1998., which is incorporated herein by reference. All vectors were produced by the Vector Core at the University of Pennsylvania as previously described [Lock, M., et al, Hum Gene Ther, 21:1259-1271 (2010)].

EXAMPLE 2: Natural History Study

All animal procedures were performed in accordance with protocols approved by the Institutional Animal Care and Use Committee (IACUC) of the University of Pennsylvania.

Citrullinemia is an autosomal recessive disease caused by mutations in argininosuccinate synthase (ASS1) enzyme that catalyzes the synthesis of argininosuccinate from citrulline and aspartate, results in citrullinemia and buildup of ammonia. ASS1$^{fold/fold}$ mouse express deficient argininosuccinate synthase 1 (ASS1) [Harris BS, et al., Follicular dystrophy: a new skin and hair mutation on mouse Chromosome 2. MGI Direct Data Submission. 2007]. FOLD allele mice have a T389I substitution in exon 15 leading to an unstable protein structure with normal ASS1 mRNA and protein levels. Homozygotes survive up to 3 weeks or longer, have 5-10% enzyme activity and display clinical and biochemical parameters similar to CTLN1. At 1 week of age fold homozygotes lack hair such that they can be distinguished from their control littermates, and at 2 weeks of age fold homozygotes have wrinkled skin, a sparse coat does grow in. By P14 mice show a 10- to 40-fold increase in the levels of citrulline, and a 1.5- to threefold increase in the plasma levels of many amino acids, including glutamine, cystine, methionine, and lysine and arginine, glutamic acid, leucine, and ornithine levels are decreased.

ASS1$^{fold/fold}$ mice thus served as a mouse model for Citrullinemia. Survival curve was generated based on the observation of 28 male and 23 female ASS1$^{fold/fold}$ mice (FIG. 2A). The result demonstrated that functionally deficient ASS1 reduced the lifespan of ASS1$^{fold/fold}$ mice significantly.

As a second parameter for normal development and growth, the body weights of ASS1$^{fold/fold}$ mice and healthy littermates after weaning were closely monitored and recorded. The results showed that female ASS1$^{fold/fold}$ mice weight remained relatively constant and the body weights of male ASS1$^{fold/fold}$ mice reached plateau at about 8 weeks old while both genders of wild-type littermates exhibited a steady growth over the observation period (FIG. 2B). It further demonstrated that functionally deficient ASS1 compromised the development and growth of the mice.

Additional testing was done on the untreated ASS1$^{fold/fold}$ mice and healthy littermates, including measurement of plasma ammonia (FIG. 2C), plasma citrulline (FIG. 2D). plasma arginine (FIG. 2E), urine orotic acid (FIG. 2E). Ammonia, citrulline, arginine and orotic acid levels were all elevated in untreated ASS1$^{fold/fold}$ mice as compared to healthy littermates.

EXAMPLE 3: AAV8.hASS1 vectors in the Model of Citrullenemia

To evaluate the efficacy and determine the dose-dependent effects of AAV8.hASS1co vectors, ASS1$^{fold/fold}$ mice were injected with $1\times10^{11}$ GC/mouse or $3\times10^{11}$ GC/mouse of the gene therapy vectors intravenously at birth, as shown in the Table 1 below. Wild-type and heterozygous littermates served as controls.

$3\times10^{11}$ GC/pup of AAV8.LSP.IVS2.hASS1co.bGH vector successfully increased the rate of weight gain in male ASS1$^{fold/fold}$ mice (FIG. 3A). In females, $3\times10^{11}$ GC/pup of all three tested vectors rescued the reduction in body weight upon growth (FIG. 3B). Meanwhile, mice injected intravenously at birth with $1\times10^{11}$ GC/pup of the vectors demonstrated a slight increase in weights (FIG. 3C and FIG. 3D). Mice which received an intraperitoneal injection of the AAV8.TBG.PI.hASS1co.WPRE.bGH vector at postnatal day 14 did not exhibit any increase in body weight (FIG. 3E and FIG. 3F).

A further experiment was performed to assess the survival of citrullenemia mice treated with the AAV8.hAASco vectors. To assess citrulline accumulation in the blood, concentration of citrulline in ASS1$^{fold/fold}$ mice with intravenous injections of AAV8.TBG.PI.hASS1co.WPRE.bGH, AAV8.LSP.IVS2.hASS1co.bGH or AAV8.TBG.PI.hASS1co.bGH on postnatal day 0 at $1\times10^{11}$ or $3\times10^{11}$ GC/pup were examined (FIG. 4B and FIG. 4A, respectively). Injection of $1\times10^{11}$ GC/pup of the vectors resulted in a minor decrease in citrulline compared to the untreated ASS1$^{fold/fold}$ mice (FIG. 4B), while $3\times10^{11}$ GC/pup of the vectors successfully brought the citrulline level down (FIG. 4A).

A further study of expression and enzyme activity of ASS1 in the injected ASS1$^{fold/fold}$ mice is performed. Livers from the tested mice injected with AAV8.hASSco vectors and the healthy littermate controls are collected and lysates are prepared. The mRNA is extracted and the expression of ASS1 is evaluated via RT-PCR. The protein expression of ASS1 is determined by western blot and immunohistochemistry. Experiments are also performed to assess the ASS1 activity in the ASS1$^{fold/fold}$ mice treated with the vector as well as controls.

An additional experiment was performed, where weight (FIG. 5A), ALT (FIG. 5B), and alkaline phosphatase (FIG. 5C) were measured on ASS1$^{fold/fold}$ mice treated with $1\times10^{11}$ GC/pup of the vector AAV8.TBG.PI.hASS1co. WPRE.bGH. Wild-type and heterozygous littermates serves as controls.

Urine orotic acid levels were measured in ASS1$^{fold/fold}$ mice injected intravenously at birth with $3\times10^{11}$ GC/pup of AAV8.TBG.PI.hASS1co. WPRE.bGH (FIG. 6A), AAV8.LSP.IVS2.hASS1co.bGH (FIG. 6B), AAV8.TBG.PI.hASS1co.bGH (FIG. 6C), or with $1\times10^{11}$ GC/pup of AAV8.LSP.IVS2.hASS1co.bGH (FIG. 6D).

EXAMPLE 4: Additional Vectors

Additional AAV vectors as shown in Table below were produced. ASS1$^{fold/fold}$ mice were injected on postnatal day 0 at $1\times10^{11}$ or $3\times10^{11}$ GC/pup with the noted vectors. Citrulline levels at two and six week post injection were measured (FIGS. 9A and 9B).

FIG. 10 shows a survival curve of male and female mice injected with G3, G7, G9 and G11. All vectors tested provided significant increase in survival of ASS1$^{fold/fold}$ mice. Likewise, all vectors tested provided an increase in body weight in both male (FIG. 11A) and female (FIG. 11B) mice, a decrease in citrulline levels at 2 weeks (FIG. 12A) and 6 weeks (FIG. 12B) post injection, and a decrease in ammonia levels (FIG. 13).

In conclusion, a single injection of AAV8.hASSco vectors resulted in substantial blood citrulline reduction and concomitant functional correction when administered intravenously in ASS1-deficient mice.

EXAMPLE 5: Long-Term Rescue of a Hypomorphic Lethal Murine Model of Citrullinemia Type I by Liver-Directed, AAV8-Mediated Gene Therapy Citrullinemia type I (CTLN1) is an autosomal, recessive disorder of the urea cycle caused by a deficiency of argininosuccinate synthase 1 (ASS1). The clinical spectrum of CTLN1 ranges from a severe neonatal onset form to a milder form with later onset. Affected patients have persistent elevated plasma citrulline levels and are at risk of life-threatening elevation of ammonia that can lead to irreversible cognitive impairment, coma, and death. Current treatment for CTLN1 patients, which includes a low protein diet, supplementation of arginine and administration of nitrogen scavengers, is often unable to prevent ongoing hyperammonemic crises. Liver transplantation has shown successful reduction of plasma ammonia and citrulline levels, but donor liver is limiting, the procedure itself carries significant morbidity, and immunosuppressive drugs are necessary for the duration of the graft. Therefore, there is a need for other approaches to therapy for CTLN1.

TABLE 1

Summary of Vectors for liver directed therapy for treatment of citrullinemia

| Grp | Vector | Key elements in vector: Enhancer-Promoter | Intron | Transgene |
|---|---|---|---|---|
| G2 | AAV8.TBG.PI.hASS1co.WPRE.bGH (p3795) | ABPx2 - TBG | PI | hASS1co |
| G3 | AAV8.TBG.IVS2.hASS1co.bGH (p4169) | ABPx2 - TBG | IVS2 | hASS1co |
| G4 | AAV8.TBG.PI.hASS1co.bGH (p4157) | ABPx2 - TBG | PI | hASS1co |
| G5 | AAV8.EnTTR.TTR.hASS1co.bGH (p4319) | EnTTR - TTR | — | hASS1co |
| G6 | AAV8.En34.A1AT.hASS1co.bGH (p4320) | En34 - A1AT | — | hASS1co |
| G7 | AAV8.TBG.PI.hASS1-native.bGH (p4339) | ABPx2 - TBG | PI | hASS1-native |
| G8 | AAV8.TBG.hFIXintron.hASS1co.bGH (p4382) | ABPx2 - TBG | hFIX intron | hASS1co |
| G9 | AAV8.ApoE.A1AT.IVS2.hASS1co.bGH (p4383) | ApoE - A1AT | IVS2 | hASS1co |
| G10 | AAV8.ApoE.A1AT(full).IVS2.hASS1co.bGH (p4385) | ApoE - A1AT (full) | IVS2 | hASS1co |
| G11 | AAV8.En34.A1AT.PI.hASS1co.bGH (p4340) | En34 - A1AT | PI | hASS1co |
| G12 | AAV8.ApoE.A1AT(full).IVS2.hASS1-native.bGH (p4456) | ApoE - A1AT (full) | IVS2 | hASS1-native |
| G13 | AAV8.ApoE.A1AT.IVS2.hASS1-native.bGH (p4457) | ApoE - A1AT | IVS2 | hASS1-native |
| G14 | AAV8.TBG.IVS2.hASS1-native.bGH (p4458) | ABPx2 - TBG | IVS2 | hASS1-native |
| G15 | AAV8.EnTTR.TTR.IVS2.hASS1-native.bGH (p4459) | EnTTR - TTR | IVS2 | hASS1-native |

| Grp | Size (bp) (ITR-ITR) | Yield (GC)/ Cellstack | w2 citrulline (μM) Mean ± STD: 3E11 GC/mouse | w2 citrulline (μM) Mean ± STD: 1E11 GC/mouse | w6 citrulline (% reduction): 3E11 GC/mouse | w6 citrulline (% reduction): 1E11 GC/mouse |
|---|---|---|---|---|---|---|
| G2 | 3325 | 1.21E+14 | 714 ± 161 (n = 5)**** | N.D. | 68.4% | N.D. |
| G3 | 3261 | 8.60E+13 | 564 ± 122 (n = 13)**** | 1065 ± 329 (n = 12) | 75 | 52 |
| G4 | 2777 | 1.26E+14 | 1272 ± 406 (n = 9) | 2176 ± 607 (n = 9) | 43 | 3 |

TABLE 1-continued

Summary of Vectors for liver directed therapy for treatment of citrullinemia

| | | | | | | |
|---|---|---|---|---|---|---|
| G5 | 2121 | 9.90E+13 | 1707 ± 732 (n = 8) | 2328 ± 348 (n = 8) | 24 | −4 |
| G6 | 2083 | 6.60E+13 | 1702 ± 549 (n = 8) | 1808 ± 542 (n = 8) | 24 | 19 |
| G7 | 2777 | 1.17E+14 | 980 ± 231 (n = 8) | 1681 ± 337 (n = 7) | 56 | 25 |
| G8 | 4040 | 1.38E+14 | 1966 ± 319 (n = 8) | 2389 ± 392 (n = 8) | 12 | −7 |
| G9 | 3066 | 6.75E+13 | 591 ± 57 (n = 9)**** | 664 ± 196 (n = 9)** | 74 | 70 |
| G10 | 3216 | 1.01E+14 | 404 ± 45 (n = 9)**** | 509 ± 118 (n = 16)**** | 82 | 77 |
| G11 | 2331 | 1.17E+14 | 746 ± 348 (n = 8)** | 1420 ± 485 (n = 8) | 67 | 37 |
| G12 | 3216 | 7.27E+13 | N.D. | 548 ± 111 (n = 10)**** | N.D. | 76 |
| G13 | 3066 | 1.10E+14 | N.D. | 494 ± 148 (n = 10)**** | N.D. | 78 |
| G14 | 3221 | 7.12E+13 | N.D. | 523 ± 147 (n = 9)**** | N.D. | 77 |
| G15 | 2798 | 1.37E+14 | N.D. | 513 ± 119 (n = 10)**** | N.D. | 77 |
| | | Fold | 2239 ± 596 (n = 13) | | | |

AAV vector-based gene therapy provides an alternative to current treatment options as long as the vector delivers sufficient and sustained transgene expression in the liver without substantial toxicity. Several candidate AAV8 vectors for CTLN1 were generated with different liver-specific promoters, introns, and cDNA sequences (native or codon-optimized hASS1 cDNA). In vivo evaluation of vectors was performed in a murine model of CTLN1 (ASS1fold/fold). Homozygous $ASS1^{fold/fold}$ (fold) mice carried a hypomorphic mutation and display lethality after weaning. Half of the untreated fold mice perished before the age of 12 weeks old, while a few (5%) lived up to 5 months. In addition to significantly elevated plasma citrulline levels, untreated fold mice had significantly reduced body weight, variable elevated plasma ammonia levels and urine orotic acid levels, and they were not fertile.

Four-week-old fold mice were dosed via retro-orbital or intraperitoneal injection with $3\times10^{11}$ GC or $1\times10^{11}$ GC of vector. Reduction of plasma citrulline levels was chosen as the main criteria to differentiate the performance of different vectors. A lead vector containing the ApoE enhancer-alpha 1 antitrypsin promoter and the beta globulin intervening sequence 2 achieved 77% reduction of citrulline levels two weeks post vector administration at the dose of $1\times10^{11}$ GC. Intron played an important role in expression of ASS1 and vectors carrying the same promoter with other introns, or no intron, showed significantly perturbed efficiency in reducing citrulline levels. Vector with native cDNA sequences performed slightly better than a vector with codon-optimized cDNA sequences. Fold mice treated with the top candidate vectors gained weight, became fertile, and survived more than 9 months (still on-going).

Sequence Listing Free Text

The following information is provided for sequences containing free text under numeric identifier <223>.

| SEQ ID NO | Amino Acid or Nucleic Acid Sequence | Free text under <223> | Description |
|---|---|---|---|
| 1 | Amino Acid | | human ASS1 |
| 2 | Nucleic Acid | <223> constructed sequence | engineered cDNA for human ASS1 |
| 3 | Nucleic Acid | | cDNA for native human ASS1 |
| 4 | Nucleic Acid | <223> constructed sequence | En34 enhancer |
| 5 | Nucleic Acid | <223> constructed sequence | EnTTR enhancer |
| 6 | Nucleic Acid | <223> constructed sequence | ABPS enhancer |
| 7 | Nucleic Acid | <223> constructed sequence | ApoE enhancer |
| 8 | Nucleic Acid | <223> constructed sequence | TBG-S1 |
| 9 | Nucleic Acid | <223> constructed sequence | TBG promoter |
| 10 | Nucleic Acid | <223> constructed sequence | A1AT promoter |
| 11 | Nucleic Acid | <223> constructed sequence | TTR promoter |
| 12 | Nucleic Acid | <223> constructed sequence | bGH polyA |
| 13 | Nucleic Acid | <223> constructed sequence | human beta globin IVS2 |
| 14 | Nucleic Acid | <223> constructed sequence | Promega ® chimeric intron |
| 15 | Nucleic Acid | <223> constructed sequence | WPRE |
| 16 | Nucleic Acid | <223> constructed sequence | 5' ITR |
| 17 | Nucleic Acid | <223> constructed sequence | 3' ITR |
| 18 | Nucleic Acid | <223> constructed sequence | hFIX intron |
| 19 | Amino Acid | <223> AAV8 | AAV8 capsid |

-continued

| SEQ ID NO | Amino Acid or Nucleic Acid Sequence | Free text under <223> | Description |
|---|---|---|---|
| 20 | Nucleic Acid | <223> constructed sequence | A1AT promoter combined with an ApoE enhancer |
| 21 | Nucleic Acid | <223> constructed sequence | liver-specific promoter LSP |
| 22 | Nucleic Acid | <223> constructed sequence | ApoE.A1AT(full).IVS2.hASS1co.bGH cis plasmid |
| 23 | Nucleic Acid | <223> constructed sequence | En34.A1AT.PI.hASS1co.bGH cis plasmid |
| 24 | Nucleic Acid | <223> constructed sequence | TBG.IVS2.hASS1co.bGH cis plasmid |
| 25 | Nucleic Acid | <223> constructed sequence | TBG.PI.hASS1co.WPRE.bGH cis plasmid |
| 26 | Nucleic Acid | <223> constructed sequence | TBG.PI.hASS1co.bGH cis plasmid |
| 27 | Nucleic Acid | <223> constructed sequence | TBG.PI.hASS1-native.bGH cis plasmid |
| 28 | Nucleic Acid | <223> constructed sequence | ApoE.A1AT(full).IVS2.hASS1-native.bGH cis plasmid |
| 29 | Nucleic Acid | <223> constructed sequence | ApoE.A1AT.IVS2.hASS1co.bGH cis plasmid |
| 30 | Nucleic Acid | <223> constructed sequence | En34.A1AT.hASS1co.bGH cis plasmid |
| 31 | Nucleic Acid | <223> constructed sequence | EnTTR.TTR.hASS1co.bGH cis plasmid |
| 32 | Nucleic Acid | <223> constructed sequence | TBG.IVS2.hASS1-native.bGH cis plasmid |
| 33 | Nucleic Acid | <223> constructed sequence | TBG.hFIXintron.hASS1co.bGH cis plasmid |
| 34 | Nucleic Acid | <223> constructed sequence | EnTTR.TTR.IVS2.hASS1-native.bGH cis plasmid |
| 35 | Nucleic Acid | <223> constructed sequence | ApoE.A1AT.IVS2.hASS1-native.bGH cis plasmid |
| 36 | Nucleic Acid | | AAV8 capsid |

All publications cited in this specification are incorporated herein by reference in their entireties, as are U.S. Provisional Patent Application No. 62/453,424, filed Feb. 1, 2017, and U.S. provisional Patent Application No. 62/469,650, filed Mar. 10, 2017. Similarly, the SEQ ID NOs which are referenced herein and which appear in the appended Sequence Listing are incorporated by reference. While the invention has been described with reference to particular embodiments, it will be appreciated that modifications can be made without departing from the spirit of the invention. Such modifications are intended to fall within the scope of the appended claims.

The invention claimed is:

1. A recombinant adeno-associated virus (AAV) comprising an AAV capsid, and a vector genome packaged therein, the vector genome comprising an expression cassette comprising a promoter operably linked to a nucleotide sequence encoding a human argininosuccinate synthase 1 (ASS1);

wherein the nucleotide sequence encoding the human ASS1 comprises SEQ ID NO: 2.

2. The recombinant AAV according to claim 1, wherein the AAV capsid is an AAV8 capsid or variant thereof.

3. The recombinant AAV of claim 1, wherein the promoter is a liver-specific promoter.

4. The recombinant AAV of claim 1, wherein the promoter is a thyroxine binding globulin (TBG) promoter, an alpha 1 anti-trypsin (A1AT) promoter, or a transthyretin promoter (TTR) promoter.

5. The recombinant AAV of claim 1, wherein the promoter is a constitutive promoter.

6. The recombinant AAV of claim 1, wherein the vector genome further comprises an AAV 5' ITR sequence from AAV2 and an AAV 3' ITR sequence from AAV2.

7. A pharmaceutical composition comprising the recombinant AAV of claim 1 and an aqueous carrier, excipient, diluent, or buffer.

8. A method of treating citrullinemia in a patient in need thereof, the method comprising administering the pharmaceutical composition of claim 7 to the patient.

9. A recombinant adeno-associated virus (AAV) comprising an AAV capsid, and a vector genome packaged therein, the vector genome comprising:

(a) an AAV 5' ITR sequence;

(b) a nucleotide sequence encoding a human argininosuccinate synthase 1(ASS1); and (c) an AAV 3' ITR sequence, wherein the nucleotide sequence encoding the human ASS1 comprises SEQ ID NO: 2.

10. The recombinant AAV of claim 9, wherein the AAV capsid is an AAV8 capsid or variant thereof.

11. The recombinant AAV of claim 9, wherein the AAV 5' ITR sequence from AAV2 and the AAV 3' ITR sequence are from AAV2.

12. The recombinant AAV of claim 9, wherein the AAV 5' ITR sequence comprises SEQ ID NO: 16 and the AAV 3' ITR sequence comprises SEQ ID NO: 17.

13. A plasmid comprising an expression cassette, the expression cassette comprising a promoter operably linked to a nucleotide sequence encoding a human argininosuccinate synthase 1 (ASS1), wherein the nucleotide sequence encoding the human ASS1 comprises SEQ ID NO: 2.

14. The plasmid of claim 13, wherein the promoter is a thyroxine binding globulin (TBG) promoter, an alpha 1 anti-trypsin (A1AT) promoter, or a transthyretin promoter (TTR) promoter.

15. The plasmid of claim 13, wherein the promoter is a constitutive promoter.

16. The plasmid of claim 13, further comprising an AAV 5' ITR sequence from AAV2 and an AAV 3' ITR sequence from AAV2, wherein the AAV 5'ITR sequence and the AAV 3' ITR sequence flank the expression cassette.

17. The plasmid of claim 16, wherein the AAV 5' ITR sequence comprises SEQ ID NO: 16 and the AAV 3' ITR sequence comprises SEQ ID NO: 17.

18. A 293 cell comprising the plasmid of claim 13.

19. A 293 cell comprising the plasmid of claim 15.

20. A 293 cell comprising the plasmid of claim 17.

* * * * *

SEQUENCE LISTING

```
Sequence total quantity: 36
SEQ ID NO: 1            moltype = AA  length = 412
FEATURE                 Location/Qualifiers
source                  1..412
                        mol_type = protein
                        organism = Homo sapiens
SEQUENCE: 1
MSSKGSVVLA YSGGLDTSCI LVWLKEQGYD VIAYLANIGQ KEDFEEARKK ALKLGAKKVF  60
IEDVSREFVE EFIWPAIQSS ALYEDRYLLG TSLARPCIAR KQVEIAQREG AKYVSHGATG  120
KGNDQVRFEL SCYSLAPQIK VIAPWRMPEF YNRFKGRNDL MEYAKQHGIP IPVTPKNPWS  180
MDENLMHISY EAGILENPKN QAPPGLYTKT QDPAKAPNTP DILEIEFKKG VPVKVTNVKD  240
GTTHQTSLEL FMYLNEVAGK HGVGRIDIVE NRFIGMKSRG IYETPAGTIL YHAHLDIEAF  300
TMDREVRKIK QGLGLKFAEL VYTGFWHSPE CEFVRHCIAK SQERVEGKVQ VSVLKGQVYI  360
LGRESPLSLY NEELVSMNVQ GDYEPTDATG FININSLRLK EYHRLQSKVT AK          412

SEQ ID NO: 2            moltype = DNA  length = 1236
FEATURE                 Location/Qualifiers
misc_feature            1..1236
                        note = constructed sequence
source                  1..1236
                        mol_type = other DNA
                        organism = synthetic construct
SEQUENCE: 2
atgagcagca agggctctgt ggtgctggcc tactctggcg gcctggacac cagctgtatc  60
ctcgtgtggc tgaaagaaca gggctacgac gtgatcgcct acctggccaa catcggccag  120
aaagaggact tcgaggaagc ccggaagaag gccctgaagc tgggcgccaa gaaggtgttc  180
atcgaggacg tgtcccgcga gttcgtggaa gagttcatct ggcccgccat ccagagcagc  240
gccctgtacg aggacagata cctgctgggc accagcctgg ccagaccctg tatcgcccgg  300
aaacaggtgg aaatcgccca gcgcgagggc gccaaatacg tgtctcacgg cgccaccggc  360
aagggcaacg accaggtgcg ctttgagctg agctgctact ccctggcccc ccagatcaaa  420
gtgatcgccc cttggcggat gcccgagttc tacaaccggt tcaagggccg gaacgacctg  480
atggaatacg ccaagcagca cggcatcccc atccccgtga cccccaagaa cccttggagc  540
atggacgaga acctgatgca catcagctac gaggccggca tcctggaaaa ccccaagaat  600
caggcccctc ccggcctgta cacaaagacc caggaccctg ccaaggcccc caacaccccc  660
gacattctgg aaatcgagtt caagaaaggc gtgcccgtga aagtgaccaa cgtgaaggac  720
ggcaccaccc accagacctc cctggaactg ttcatgtacc tgaacgaggt ggccggcaag  780
cacggcgtgg gcagaatcga catcgtggaa aacagattca tcggcatgaa gtcccggggc  840
atctacgaga caccagccgg caccatcctg taccacgccc acctggatat cgaggccttc  900
```

-continued

```
accatggacc gggaagtgcg gaagatcaag cagggcctgg gcctgaagtt cgccgagctg  960
gtgtacacag gcttttggca cagccccgag tgcgagtttg tgcggcactg cattgccaag  1020
agccaggaac gggtggaagg caaggtgcag gtgtccgtgc tgaagggcca ggtgtacatt  1080
ctgggcagag agagcccccct gagcctgtac aacgaggaac tggtgtctat gaacgtgcag  1140
ggcgactacg agcccaccga cgccaccggc ttcatcaaca tcaacagcct gagactgaaa  1200
gagtaccacc ggctgcagtc caaagtgacc gccaag                            1236

SEQ ID NO: 3            moltype = DNA  length = 1236
FEATURE                 Location/Qualifiers
source                  1..1236
                        mol_type = genomic DNA
                        organism = Homo sapiens
SEQUENCE: 3
atgtccagca aaggctccgt ggttctggcc tacagtggcg gcctggacac ctcgtgcatc  60
ctcgtgtggc tgaaggaaca aggctatgac gtcattgcct atctggccaa cattggccag  120
aaggaagact tcgaggaagc caggaagaag gcactgaagc ttggggccaa aaaggtgttc  180
attgaggatg tcagcaggga gtttgtggag gagttcatct ggccggccat ccagtccagc  240
gcactgtatg aggaccgcta cctcctgggc acctctcttg ccaggccctg catcgcccgc  300
aaacaagtgg aaatcgccca gcgggagggg gccaagtatg tgtcccacgg cgccacagga  360
aaggggaacg atcaggtccg gtttgagctc agctgctact cactggcccc ccagataaag  420
gtcattgctc cctggaggat gcctgaattc tacaaccggt tcaagggccg caatgacctg  480
atggagtacg caaagcaaca cgggattccc atcccggtca ctcccaagaa cccgtggagc  540
atggatgaga acctcatgca catcagctac gaggctggaa tcctggagaa ccccaagaac  600
caagcgcctc caggtctcta cacgaagacc caggacccag ccaaagcccc caacacccct  660
gacattctcg agatcgagtt caaaaaaggg gtccctgtga aggtgaccaa cgtcaaggat  720
ggcaccaccc accagacctc cttggagctc ttcatgtacc tgaacgaagt cgcgggcaag  780
catggcgtgg gccgtattga catcgtggag aaccgcttca ttggaatgaa gtcccgaggt  840
atctacgaga ccccagcagg caccatcctt taccacgctc atttagacat cgaggccttc  900
accatggacc gggaagtgcg caaaatcaaa caaggcctgg gcttgaaatt tgctgagctg  960
gtgtataccg gtttctggca cagccctgag tgtgaatttg tccgccactg catcgccaag  1020
tcccaggagc gagtggaagg gaaagtgcag gtgtccgtcc tcaagggcca ggtgtacatc  1080
ctcggccggg agtccccact gtctctctac aatgaggagc tggtgagcat gaacgtgcag  1140
ggtgattatg agccaactga tgccaccggg ttcatcaaca tcaattccct caggctgaag  1200
gaatatcatc gtctccagag caaggtcact gccaaa                            1236

SEQ ID NO: 4            moltype = DNA  length = 34
FEATURE                 Location/Qualifiers
misc_feature            1..34
                        note = constructed sequence
source                  1..34
                        mol_type = other DNA
                        organism = synthetic construct
SEQUENCE: 4
tgtttgctgc ttgcaatgtt tgcccatttt aggg                              34

SEQ ID NO: 5            moltype = DNA  length = 100
FEATURE                 Location/Qualifiers
misc_feature            1..100
                        note = constructed sequence
source                  1..100
                        mol_type = other DNA
                        organism = synthetic construct
SEQUENCE: 5
ctacctcgtg atcgcccggc ccctgttcaa acatgtccta atactctgtc tctgcaaggg  60
tcatcagtag ttttccatct tactcaacat cctcccagtg                        100

SEQ ID NO: 6            moltype = DNA  length = 42
FEATURE                 Location/Qualifiers
misc_feature            1..42
                        note = constructed sequence
source                  1..42
                        mol_type = other DNA
                        organism = synthetic construct
SEQUENCE: 6
aggttaattt ttaaactgtt tgctctggtt aataatctca gg                     42

SEQ ID NO: 7            moltype = DNA  length = 322
FEATURE                 Location/Qualifiers
misc_feature            1..322
                        note = constructed sequence
source                  1..322
                        mol_type = other DNA
                        organism = synthetic construct
SEQUENCE: 7
aaggctcaga ggcacacagg agtttctggg ctcaccctgc cccccttccaa cccctcagtt  60
cccatcctcc agcagctgtt tgtgtgctgc ctctgaagtc cacactgaac aaacttcagc  120
ctactcatgt ccctaaaatg ggcaaacatt gcaagcagca aacagcaaac acacagccct  180
ccctgcctgc tgaccttgga gctggggcag aggtcagaga cctctctggg cccatgccac  240
ctccaacatc cactcgaccc cttggaattt cggtggagag gagcagaggt tgtcctggcg  300
```

```
tggtttaggt agtgtgagag gg                                          322

SEQ ID NO: 8            moltype = DNA  length = 176
FEATURE                 Location/Qualifiers
misc_feature            1..176
                        note = constructed sequence
source                  1..176
                        mol_type = other DNA
                        organism = synthetic construct
SEQUENCE: 8
actcaaagtt caaaccttat cattttttgc tttgttcctc ttggccttgg ttttgtacat  60
cagctttgaa aataccatcc cagggttaat gctggggtta atttataact aagagtgctc  120
tagttttgca atacaggaca tgctataaaa atggaaagat gttgctttct gagaga      176

SEQ ID NO: 9            moltype = DNA  length = 477
FEATURE                 Location/Qualifiers
misc_feature            1..477
                        note = constructed sequence
source                  1..477
                        mol_type = other DNA
                        organism = synthetic construct
SEQUENCE: 9
agggctggaa gctacctttg acatcatttc ctctgcgaat gcatgtataa tttctacaga  60
acctattaga aaggatcacc cagcctctgc ttttgtacaa ctttccctta aaaaactgcc  120
aattccactg ctgtttggcc caatagtgag aactttttcc tgctgcctct tggtgctttt  180
gcctatggcc cctattctgc ctgctgaaga cactcttgcc agcatggact taaacccctc  240
cagctctgac aatcctcttt ctcttttgtt ttacatgaag ggtctggcag ccaaagcaat  300
cactcaaagt tcaaacctta tcattttttg ctttgttcct cttggccttg gttttgtaca  360
tcagctttga aaataccatc ccagggttaa tgctggggtt aatttataac taagagtgct  420
ctagttttgc aatacaggac atgctataaa aatggaaaga tgttgctttc tgagaga     477

SEQ ID NO: 10           moltype = DNA  length = 218
FEATURE                 Location/Qualifiers
misc_feature            1..218
                        note = constructed sequence
source                  1..218
                        mol_type = other DNA
                        organism = synthetic construct
SEQUENCE: 10
tggacacagg acgctgtggt ttctgagcca gggggcgact cagatcccag ccagtggact  60
tagcccctgt ttgctcctcc gataactggg gtgaccttgg ttaatattca ccagcagcct  120
cccccgttgc ccctctggat ccactgctta aatacggacg aggacagggc cctgtctcct  180
cagcttcagg caccaccact gacctgggac agtgaata                          218

SEQ ID NO: 11           moltype = DNA  length = 190
FEATURE                 Location/Qualifiers
misc_feature            1..190
                        note = constructed sequence
source                  1..190
                        mol_type = other DNA
                        organism = synthetic construct
SEQUENCE: 11
atttcataga acgaatgttc cgatgctcta atctctctag acaaggttca tatttgtatg  60
ggttacttat tctctctttg ttgactaagt caataatcag aatcagcagg tttgcagtca  120
gattggcagg gataagcagc ctagctcagg agaagtgagt ataaaagccc caggctggga  180
gcagccatca                                                        190

SEQ ID NO: 12           moltype = DNA  length = 215
FEATURE                 Location/Qualifiers
misc_feature            1..215
                        note = constructed sequence
source                  1..215
                        mol_type = other DNA
                        organism = synthetic construct
SEQUENCE: 12
gcctcgactg tgccttctag ttgccagcca tctgttgttt gcccctcccc cgtgccttcc  60
ttgaccctgg aaggtgccac tcccactgtc ctttcctaat aaaatgagga aattgcatcg  120
cattgtctga gtaggtgtca ttctattctg gggggtgggg tggggcagga cagcaagggg  180
gaggattggg aagacaatag caggcatgct gggga                             215

SEQ ID NO: 13           moltype = DNA  length = 572
FEATURE                 Location/Qualifiers
misc_feature            1..572
                        note = constructed sequence
source                  1..572
                        mol_type = other DNA
                        organism = synthetic construct
SEQUENCE: 13
agcttacttg tggtaccgag ctcggatcct gagaacttca gggtgagtct atgggaccct  60
```

-continued

```
tgatgttttc tttccccttc ttttctatgg ttaagttcat gtcataggaa ggggagaagt  120
aacagggtac acatattgac caaatcaggg taattttgca tttgtaattt taaaaaatgc  180
tttcttcttt taatatactt ttttgtttat cttatttcta atactttccc taatctcttt  240
ctttcagggc aataatgata caatgtatca tgcctctttg caccattcta aagaataaca  300
gtgataattt ctgggttaag gcaatagcaa tatttctgca tataaatatt tctgcatata  360
aattgtaact gatgtaagag gtttcatatt gctaatagca gctacaatcc agctaccatt  420
ctgcttttat tttatggttg ggataaggct ggattattct gagtccaagc taggcccttt  480
tgctaatcat gttcatacct cttatcttcc tcccacagct cctgggcaac gtgctggtct  540
gtgtgctggc ccatcacttt ggcaaagaat tg                                572

SEQ ID NO: 14          moltype = DNA  length = 133
FEATURE                Location/Qualifiers
misc_feature           1..133
                       note = constructed sequence
source                 1..133
                       mol_type = other DNA
                       organism = synthetic construct
SEQUENCE: 14
gtaagtatca aggttacaag acaggtttaa ggagaccaat agaaactggg cttgtcgaga  60
cagagaagac tcttgcgttt ctgataggca cctattggtc ttactgacat ccactttgcc  120
tttctctcca cag                                                     133

SEQ ID NO: 15          moltype = DNA  length = 542
FEATURE                Location/Qualifiers
misc_feature           1..542
                       note = constructed sequence
source                 1..542
                       mol_type = other DNA
                       organism = synthetic construct
SEQUENCE: 15
aatcaacctc tggattacaa aatttgtgaa agattgactg gtattcttaa ctatgttgct  60
ccttttacgc tatgtggata cgctgcttta atgcctttgt atcatgctat tgcttcccgt  120
atggctttca ttttctcctc cttgtataaa tcctggttgc tgtctcttta tgaggagttg  180
tggcccgttg tcaggcaacg tggcgtggtg tgcactgtgt ttgctgacgc aacccccact  240
ggttggggca ttgccaccac ctgtcagctc ctttccggga ctttcgcttt ccccctccct  300
attgccacgg cggaactcat cgccgcctgc cttgcccgct gctggacagg ggctcggctg  360
ttgggcactg acaattccgt ggtgttgtcg gggaaatcat cgtcctttcc ttggctgctc  420
gcctgtgttg ccacctggat tctgcgcggg acgtccttct gctacgtccc ttcggccctc  480
aatccagcgg accttccttc ccgcggcctg ctgccggctc tgcggcctct tccgcgtctt  540
cg                                                                 542

SEQ ID NO: 16          moltype = DNA  length = 168
FEATURE                Location/Qualifiers
misc_feature           1..168
                       note = constructed sequence
source                 1..168
                       mol_type = other DNA
                       organism = synthetic construct
SEQUENCE: 16
ctgcgcgctc gctcgctcac tgaggccgcc cgggcaaagc ccgggcgtcg ggcgaccttt  60
ggtcgcccgg cctcagtgag cgagcgagcg cgcagagagg gagtggccaa ctccatcact  120
aggggttcct tgtagttaat gattaacccg ccatgctact tatctacg               168

SEQ ID NO: 17          moltype = DNA  length = 168
FEATURE                Location/Qualifiers
misc_feature           1..168
                       note = constructed sequence
source                 1..168
                       mol_type = other DNA
                       organism = synthetic construct
SEQUENCE: 17
cgtagataag tagcatggcg ggttaatcat taactacaag gaacccctag tgatggagtt  60
ggccactccc tctctgcgcg ctcgctcgct cactgaggcc gggcgaccaa aggtcgcccg  120
acgcccgggc tttgcccggg cggcctcagt gagcgagcga gcgcgcag               168

SEQ ID NO: 18          moltype = DNA  length = 1421
FEATURE                Location/Qualifiers
misc_feature           1..1421
                       note = constructed sequence
source                 1..1421
                       mol_type = other DNA
                       organism = synthetic construct
SEQUENCE: 18
gtttgtttcc ttttttaaaa tacattgagt atgcttgcct tttagatata gaaatatctg  60
atgctgtctt cttcactaaa ttttgattac atgatttgac agcaatattg aagagtctaa  120
cagccagcac gcaggttggt aagtactggt tctttgttag ctaggttttc ttcttcttca  180
tttttaaaac taaatagatc gacaatgctt atgatgcatt tatgtttaat aaacactgtt  240
cagttcatga tttggtcatg taattcctgt tagaaaacat tcatctcctt ggtttaaaaa  300
aattaaaagt gggaaaacaa agaaatagca gaatatagtg aaaaaaaata accacattat  360
```

-continued

```
ttttgtttgg acttaccact ttgaaatcaa aatgggaaac aaaagcacaa acaatggcct  420
tatttacaca aaaagtctga ttttaagata tatgacattt caaggtttca gaagtatgta  480
atgaggtgtg tctctaattt tttaaattat atatcttcaa tttaaagttt tagttaaaac  540
ataaagatta acctttcatt agcaagctgt tagttatcac caaagctttt catggattag  600
gaaaaaatca ttttgtctct atgtcaaaca tcttggagtt gatatttggg gaaacacaat  660
actcagttga gttccctagg ggagaaaagc aagcttaaga attgacataa agagtaggaa  720
gttagctaat gcaacatata tcactttgtt ttttcacaac tacagtgact ttatgtattt  780
cccagaggaa ggcatacagg gaagaaatta tcccatttgg acaaacagca tgttctcaca  840
ggaagcattt atcacactta cttgtcaact ttctagaatc aaatctagta gctgacagta  900
ccaggatcag gggtgccaac cctaagcacc cccagaaagc tgactggccc tgtggttccc  960
actccagaca tgatgtcagc tggaccataa ttaggcttct gttcttcagg agacatttgt  1020
tcaaagtcat ttgggcaacc atattctgaa aacagcccag ccagggtgat ggatcacttt  1080
gcaaagatcc tcaatgagct attttcaagt gatgacaaag tgtgaagtta accgctcatt  1140
tgagaacttt ctttttcatc caaagtaaat tcaaatatga ttagaaatct gaccttttat  1200
tactggaatt ctcttgacta aaagtaaaat tgaattttaa ttcctaaatc tccatgtgta  1260
tacagtactg tgggaacatc acagattttg gctccatgcc ctaaagagaa attggctttc  1320
agattatttg gattaaaaac aaagactttc ttaagagatg taaaattttc atgatgtttt  1380
ctttttgct aaaactaaag aattattctt ttacatttca g                     1421

SEQ ID NO: 19          moltype = AA  length = 738
FEATURE                Location/Qualifiers
REGION                 1..738
                       note = AAV8
source                 1..738
                       mol_type = protein
                       organism = unidentified
SEQUENCE: 19
MAADGYLPDW LEDNLSEGIR EWWALKPGAP KPKANQQKQD DGRGLVLPGY KYLGPFNGLD  60
KGEPVNAADA AALEHDKAYD QQLQAGDNPY LRYNHADAEF QERLQEDTSF GGNLGRAVFQ  120
AKKRVLEPLG LVEEGAKTAP GKKRPVEPSP QRSPDSSTGI GKKGQQPARK RLNFGQTGDS  180
ESVPDPQPLG EPPAAPSGVG PNTMAAGGGA PMADNNEGAD GVGSSSGNWH CDSTWLGDRV  240
ITTSTRTWAL PTYNNHLYKQ ISNGTSGGAT NDNTYFGYST PWGYFDFNRF HCHFSPRDWQ  300
RLINNNWGFR PKRLSFKLFN IQVKEVTQNE GTKTIANNLT STIQVFTDSE YQLPYVLGSA  360
HQGCLPPFPA DVFMIPQYGY LTLNNGSQAV GRSSFYCLEY FPSQMLRTGN NFQFTYTFED  420
VPFHSSYAHS QSLDRLMNPL IDQYLYYLSR TQTTGGTANT QTLGFSQGGP NTMANQAKNW  480
LPGPCYRQQR VSTTTGQNNN SNFAWTAGTK YHLNGRNSLA NPGIAMATHK DDEERFFPSN  540
GILIFGKQNA ARDNADYSDV MLTSEEEIKT TNPVATEEYG IVADNLQQQN TAPQIGTVNS  600
QGALPGMVWQ NRDVYLQGPI WAKIPHTDGN FHPSPLMGGF GLKHPPPQIL IKNTPVPADP  660
PTTFNQSKLN SFITQYSTGQ VSVEIEWELQ KENSKRWNPE IQYTSNYYKS TSVDFAVNTE  720
GVYSEPRPIG TRYLTRNL                                               738

SEQ ID NO: 20          moltype = DNA  length = 735
FEATURE                Location/Qualifiers
misc_feature           1..735
                       note = constructed sequence
source                 1..735
                       mol_type = other DNA
                       organism = synthetic construct
SEQUENCE: 20
gctcagaggc acacaggagt ttctgggctc accctgcccc cttccaaccc ctcagttccc  60
atcctccagc agctgtttgt gtgctgcctc tgaagtccac actgaacaaa cttcagccta  120
ctcatgtccc taaaatgggc aaacattgca agcagcaaac agcaaacaca cagccctccc  180
tgcctgctga ccttggagct ggggcagagg tcagagacct ctctgggccc atgccacctc  240
caacatccac tcgacccctt ggaatttcgg tggagaggag cagaggttgt cctggcgtgg  300
tttaggtagt gtgagagggc gcgccgatct tgctaccagt ggaacagcca ctaaggattc  360
tgcagtgaga gcagagggcc agctaagtgg tactctccca gagactgtct gactcacgcc  420
acccccctcca ccttggacac aggacgctgt ggtttctgag ccaggtacaa tgactccttt  480
cggtaagtgc agtggaagct gtacactgcc caggcaaagc gtccgggcag cgtaggcggg  540
cgactcagat cccagccagt ggacttagcc cctgtttgct cctccgataa ctggggtgac  600
cttggttaat attcaccagc agcctccccc gttgcccctc tggatccact gcttaaatac  660
ggacgaggac agggccctgt ctcctcagct tcaggcacca ccactgacct gggacagtag  720
atctagctta cttgt                                                  735

SEQ ID NO: 21          moltype = DNA  length = 727
FEATURE                Location/Qualifiers
misc_feature           1..727
                       note = constructed sequence
source                 1..727
                       mol_type = other DNA
                       organism = synthetic construct
SEQUENCE: 21
agttaatttt taaaaagcag tcaaaagtcc aagtgccctt gcgagcattt actctctctg  60
tttgctctgg ttaataatct caggagcaca aacattcctt actagttcta ggagttaatt  120
tttaaaaagc agtcaaaagt ccaagtgccc ttgcgagcat ttactctctc tgtttgctct  180
ggttaataat ctcaggagca caaacattcc ttactagttc tagagcggcc gccagtgtgc  240
tggaattcgg ctttttagg gctggaagct acctttgaca tcatttcctc tgcgaatgca  300
tgtataattt ctacagaacc tattagaaag gatcacccag cctctgcttt tgtacaactt  360
tcccttaaaa aactgccaat cccactgctg tttggcccaa tagtgagaac tttttcctgc  420
tgcctcttgg tgcttttgcc tatggcccct attctgcctg ctgaagacac tcttgccagc  480
```

-continued

```
atggacttaa accccctccag ctctgacaat cctctttctc ttttgtttta catgaagggt  540
ctggcagcca aagcaatcac tcaaagttca aaccttatca ttttttgctt tgttcctctt  600
ggccttggtt ttgtacatca gctttgaaaa taccatccca gggttaatgc tggggttaat  660
ttataactga gagtgctcta gttctgcaat acaggacatg ctataaaaat ggaaagatgt  720
tgctttc                                                           727
```

```
SEQ ID NO: 22          moltype = DNA  length = 6026
FEATURE                Location/Qualifiers
misc_feature           1..6026
                       note = constructed sequence
source                 1..6026
                       mol_type = other DNA
                       organism = synthetic construct
SEQUENCE: 22
ctgcgcgctc gctcgctcac tgaggccgcc cgggcaaagc ccgggcgtcg ggcgaccttt  60
ggtcgcccgg cctcagtgag cgagcgagcg cgcagagagg gagtggccaa ctccatcact  120
aggggttcct tgtagttaat gattaacccg ccatgctact tatctacgta gccatgctct  180
aggaagatcg gaattcgccc ttaaggctca gaggcacaca ggagtttctg ggctcaccct  240
gccccccttcc aacccctcag ttcccatcct ccagcagctg tttgtgtgct gcctctgaag  300
tccacactga acaaacttca gcctactcat gtccctaaaa tgggcaaaca ttgcaagcag  360
caaacagcaa acacacagcc ctccctgcct gctgaccttg gagctggggc agaggtcaga  420
gacctctctg ggcccatgcc acctccaaca tccactcgac cccttggaat ttcggtggag  480
aggagcagag gttgtcctgg cgtggtttag gtagtgtgag agggcgcgcc gatcttgcta  540
ccagtggaac agccactaag gattctgcag tgagagcaga gggccagcta agtggtactc  600
tcccagagac tgtctgactc acgccacccc ctccaccttg gacacaggac gctgtggttt  660
ctgagccagg tacaatgact cctttcggta agtgcagtgg aagctgtaca ctgcccaggc  720
aaagcgtccg ggcagcgtag gcgggcgact cagatcccag ccagtggact tagcccctgt  780
ttgctcctcc gataactggg gtgaccttgg ttaatattca ccagcagcct cccccgttgc  840
ccctctggat ccactgctta aatacggacg aggacagggc cctgtctcct cagcttcagg  900
caccaccact gacctgggac agtagatcta gcttacttgt ggtaccgagc tcggatcctg  960
agaacttcag ggtgagtcta tgggaccctt gatgttttct ttccccttct tttctatggt  1020
taagttcatg tcataggaag gggagaagta acagggtaca catattgacc aaatcagggt  1080
aattttgcat ttgtaatttt aaaaaatgct ttcttctttt aatatacttt tttgtttatc  1140
ttatttctaa tactttccct aatctctttc tttcagggca ataatgatac aatgtatcat  1200
gcctctttgc accattctaa agaataacag tgataatttc tgggttaagg caatagcaat  1260
atttctgcat ataaatattt ctgcatataa attgtaactg atgtaagagg tttcatattg  1320
ctaatagcag ctacaatcca gctaccattc tgcttttatt ttatggttgg gataaggctg  1380
gattattctg agtccaagct aggccctttt gctaatcatg ttcatacctc ttatcttcct  1440
cccacagctc ctgggcaacg tgctggtctg tgtgctggcc catcactttg gcaaagaatt  1500
gatctcgagt aactgaaggc ggccgccacc atgagcagca agggctctgt ggtgctggcc  1560
tactctggcg gcctggacac cagctgtatc ctcgtgtggc tgaaagaaca gggctacgac  1620
gtgatcgcct acctggccaa catcggccag aaagaggact tcgaggaagc ccggaagaag  1680
gccctgaagc tgggcgccaa gaaggtgttc atcgaggacg tgtcccgcga gttcgtggaa  1740
gagttcatct ggcccgccat ccagagcagc gccctgtacg aggacagata cctgctgggc  1800
accagcctgg ccagaccctg tatcgcccgg aaacaggtgg aaatcgccca gcgcgagggc  1860
gccaaatacg tgtctcacgg cgccaccggc aagggcaacg accaggtgcg ctttgagctg  1920
agctgctact ccctggcccc ccagatcaaa gtgatcgccc cttggcggat gcccgagttc  1980
tacaaccggt tcaagggccg gaacgacctg atggaatacg ccaagcagca cggcatcccc  2040
atccccgtga cccccaagaa cccttggagc atggacgaga acctgatgca catcagctac  2100
gaggccggca tcctggaaaa ccccaagaat caggcccctc ccggcctgta cacaaagacc  2160
caggaccctg ccaaggcccc caacaccccc gacattctgg aaatcgagtt caagaaaggc  2220
gtgcccgtga aagtgaccaa cgtgaaggac ggcaccaccc accagacctc cctggaactg  2280
ttcatgtacc tgaacgaggt ggccggcaag cacggcgtgg gcagaatcga catcgtggaa  2340
aacagattca tcggcatgaa gtcccggggc atctacgaga caccagccgg caccatcctg  2400
taccacgccc acctggatat cgaggccttc accatggacc gggaagtgcg gaagatcaag  2460
cagggcctgg gcctgaagtt cgccgagctg gtgtacacag gcttttggca cagccccgag  2520
tgcgagtttg tgcggcactg cattgccaag agccaggaac gggtggaagg caaggtgcag  2580
gtgtccgtgc tgaagggcca ggtgtacatt ctgggcagag agagccccct gagcctgtac  2640
aacgaggaac tggtgtctat gaacgtgcag ggcgactacg agcccaccga cgccaccggc  2700
ttcatcaaca tcaacagcct gagactgaaa gagtaccacc ggctgcagtc caaagtgacc  2760
gccaagtgat aagcatgcgg atctgcctcg actgtgcctt ctagttgcca gccatctgtt  2820
gtttgcccct cccccgtgcc ttccttgacc ctggaaggtg ccactcccac tgtcctttcc  2880
taataaaatg aggaaattgc atcgcattgt ctgagtaggt gtcattctat tctggggggt  2940
ggggtggggc aggacagcaa gggggaggat tgggaagaca atagcaggca tgctggggac  3000
tcgagttaag ggcgaattcc cgataaggat cttcctagag catggctacg tagataagta  3060
gcatggcggg ttaatcatta actacaagga acccctagtg atggagttgg ccactccctc  3120
tctgcgcgct cgctcgctca ctgaggccgg gcgaccaaag gtcgcccgac gcccgggctt  3180
tgcccgggcg gcctcagtga gcgagcgagc gcgcagcctt aattaaccta attcactggc  3240
cgtcgtttta caacgtcgtg actgggaaaa ccctggcgtt acccaactta atcgccttgc  3300
agcacatccc cctttcgcca gctggcgtaa tagcgaagag gcccgcaccg atcgcccttc  3360
ccaacagttg cgcagcctga atggcgaatg ggacgcgccc tgtagcggcg cattaagcgc  3420
ggcgggtgtg gtggttacgc gcagcgtgac cgctacactt gccagcgccc tagcgcccgc  3480
tcctttcgct ttcttccctt cctttctcgc cacgttcgcc ggctttcccc gtcaagctct  3540
aaatcggggg ctccctttag ggttccgatt tagtgcttta cggcacctcg accccaaaaa  3600
acttgattag ggtgatggtt cacgtagtgg gccatcgccc tgatagacgg tttttcgccc  3660
tttgacgttg gagtccacgt tctttaatag tggactcttg ttccaaactg gaacaacact  3720
caaccctatc tcggtctatt cttttgattt ataagggatt ttgccgattt cggcctattg  3780
gttaaaaaat gagctgattt aacaaaaatt taacgcgaat tttaacaaaa tattaacgct  3840
tacaatttag gtggcacttt tcggggaaat gtgcgcggaa cccctatttg tttatttttc  3900
```

-continued

```
taaatacatt caaatatgta tccgctcatg agacaataac cctgataaat gcttcaataa  3960
tattgaaaaa ggaagagtat gagtattcaa catttccgtg tcgcccttat tccctttttt  4020
gcggcatttt gccttcctgt ttttgctcac ccagaaacgc tggtgaaagt aaaagatgct  4080
gaagatcagt tgggtgcacg agtgggttac atcgaactgg atctcaacag cggtaagatc  4140
cttgagagtt ttcgccccga agaacgtttt ccaatgatga gcacttttaa agttctgcta  4200
tgtggcgcgg tattatcccg tattgacgcc gggcaagagc aactcggtcg ccgcatacac  4260
tattctcaga atgacttggt tgagtactca ccagtcacag aaaagcatct tacggatggc  4320
atgacagtaa gagaattatg cagtgctgcc ataaccatga gtgataacac tgcggccaac  4380
ttacttctga caacgatcgg aggaccgaag gagctaaccg cttttttgca caacatgggg  4440
gatcatgtaa ctcgccttga tcgttgggaa ccggagctga atgaagccat accaaacgac  4500
gagcgtgaca ccacgatgcc tgtagcaatg gcaacaacgt tgcgcaaact attaactggc  4560
gaactactta ctctagcttc ccggcaacaa ttaatagact ggatggaggc ggataaagtt  4620
gcaggaccac ttctgcgctc ggcccttccg gctggctggt ttattgctga taaatctgga  4680
gccggtgagc gtgggtctcg cggtatcatt gcagcactgg ggccagatgg taagccctcc  4740
cgtatcgtag ttatctacac gacggggagt caggcaacta tggatgaacg aaatagacag  4800
atcgctgaga taggtgcctc actgattaag cattggtaac tgtcagacca agtttactca  4860
tatatacttt agattgattt aaaacttcat ttttaattta aaaggatcta ggtgaagatc  4920
ctttttgata atctcatgac caaaatccct taacgtgagt tttcgttcca ctgagcgtca  4980
gaccccgtag aaaagatcaa aggatcttct tgagatcctt tttttctgcg cgtaatctgc  5040
tgcttgcaaa caaaaaaacc accgctacca gcggtggttt gtttgccgga tcaagagcta  5100
ccaactcttt ttccgaaggt aactggcttc agcagagcgc agataccaaa tactgttctt  5160
ctagtgtagc cgtagttagg ccaccacttc aagaactctg tagcaccgcc tacatacctc  5220
gctctgctaa tcctgttacc agtggctgct gccagtggcg ataagtcgtg tcttaccggg  5280
ttggactcaa gacgatagtt accggataag gcgcagcggt cgggctgaac ggggggttcg  5340
tgcacacagc ccagcttgga gcgaacgacc tacaccgaac tgagatacct acagcgtgag  5400
ctatgagaaa gcgccacgct tcccgaaggg agaaaggcgg acaggtatcc ggtaagcggc  5460
agggtcggaa caggagagcg cacgagggag cttccagggg gaaacgcctg gtatctttat  5520
agtcctgtcg ggtttcgcca cctctgactt gagcgtcgat ttttgtgatg ctcgtcaggg  5580
gggcggagcc tatggaaaaa cgccagcaac gcggcctttt tacggttcct ggccttttgc  5640
tggccttttg ctcacatgtt ctttcctgcg ttatcccctg attctgtgga taaccgtatt  5700
accgcctttg agtgagctga taccgctcgc cgcagccgaa cgaccgagcg cagcgagtca  5760
gtgagcgagg aagcggaaga gcgcccaata cgcaaaccgc ctctccccgc gcgttggccg  5820
attcattaat gcagctggca cgacaggttt cccgactgga aagcgggcag tgagcgcaac  5880
gcaattaatg tgagttagct cactcattag gcaccccagg ctttacactt tatgcttccg  5940
gctcgtatgt tgtgtggaat tgtgagcgga taacaatttc acacaggaaa cagctatgac  6000
catgattacg ccagatttaa ttaagg                                        6026

SEQ ID NO: 23          moltype = DNA  length = 5141
FEATURE                Location/Qualifiers
misc_feature           1..5141
                       note = constructed sequence
source                 1..5141
                       mol_type = other DNA
                       organism = synthetic construct
SEQUENCE: 23
ctgcgcgctc gctcgctcac tgaggccgcc cgggcaaagc ccgggcgtcg ggcgaccttt  60
ggtcgcccgg cctcagtgag cgagcgagcg cgcagagagg gagtggccaa ctccatcact  120
aggggttcct tgtagttaat gattaacccg ccatgctact tatctacgta gccatgctct  180
aggaagatcg gaattcgccc ttaagctagc tgtttgctgc ttgcaatgtt tgcccatttt  240
agggtggaca caggacgctg tggtttctga gccagggggc gactcagatc ccagccagtg  300
gacttagccc ctgtttgctc ctccgataac tggggtgacc ttggttaata ttcaccagca  360
gcctcccccg ttgcccctct ggatccactg cttaaatacg gacgaggaca gggccctgtc  420
tcctcagctt caggcaccac cactgacctg ggacagtgaa tctgcagaag ttggtcgtga  480
ggcactgggc aggtaagtat caaggttaca agacaggttt aaggagacca atagaaactg  540
ggcttgtcga gacagagaag actcttgcgt ttctgatagg cacctattgg tcttactgac  600
atccactttg cctttctctc cacaggtgtc caggcggccg ccaccatgag cagcaagggc  660
tctgtggtgc tggcctactc tggcggcctg gacaccagct gtatcctcgt gtggctgaaa  720
gaacagggct acgacgtgat cgcctacctg gccaacatcg gccagaaaga ggacttcgag  780
gaagcccgga agaaggccct gaagctgggc gccaagaagg tgttcatcga ggacgtgtcc  840
cgcgagttcg tggaagagtt catctggccc gccatccaga gcagcgccct gtacgaggac  900
agatacctgc tgggcaccag cctggccaga ccctgtatcg cccggaaaca ggtggaaatc  960
gcccagcgcg agggcgccaa atacgtgtct cacggcgcca ccggcaaggg caacgaccag  1020
gtgcgctttg agctgagctg ctactccctg gccccccaga tcaaagtgat cgccccttgg  1080
cggatgcccg agttctacaa ccggttcaag ggccggaacg acctgatgga atacgccaag  1140
cagcacggca tccccatccc cgtgaccccc aagaaccctt ggagcatgga cgagaacctg  1200
atgcacatca gctacgaggc cggcatcctg gaaaacccca agaatcaggc ccctcccggc  1260
ctgtacacaa agacccagga ccctgccaag gcccccaaca cccccgacat tctggaaatc  1320
gagttcaaga aaggcgtgcc cgtgaaagtg accaacgtga aggacggcac cacccaccag  1380
acctccctgg aactgttcat gtacctgaac gaggtggccg gcaagcacgg cgtgggcaga  1440
atcgacatcg tggaaaacag attcatcggc atgaagtccc ggggcatcta cgagacacca  1500
gccggcacca tcctgtacca cgcccacctg gatatcgagg ccttcaccat ggaccgggaa  1560
gtgcggaaga tcaagcaggg cctgggcctg aagttcgccg agctggtgta cacaggcttt  1620
tggcacagcc ccgagtgcga gtttgtgcgg cactgcattg ccaagagcca ggaacgggtg  1680
gaaggcaagg tgcaggtgtc cgtgctgaag ggccaggtgt acattctggg cagagagagc  1740
cccctgagcc tgtacaacga ggaactggtg tctatgaacg tgcagggcga ctacgagccc  1800
accgacgcca ccggcttcat caacatcaac agcctgagac tgaaagagta ccaccggctg  1860
cagtccaaag tgaccgccaa gtgataagca tgcggatctg cctcgactgt gccttctagt  1920
tgccagccat ctgttgtttg cccctccccc gtgccttcct tgaccctgga aggtgccact  1980
cccactgtcc tttcctaata aaatgaggaa attgcatcgc attgtctgag taggtgtcat  2040
```

-continued

```
tctattctgg ggggtggggt ggggcaggac agcaaggggg aggattggga agacaatagc  2100
aggcatgctg gggactcgag ttaagggcga attcccgatt aggatcttcc tagagcatgg  2160
ctacgtagat aagtagcatg gcgggttaat cattaactac aaggaacccc tagtgatgga  2220
gttggccact ccctctctgc gcgctcgctc gctcactgag gccgggcgac caaaggtcgc  2280
ccgacgcccg ggctttgccc gggcggcctc agtgagcgag cgagcgcgca gccttaatta  2340
acctaattca ctggccgtcg ttttacaacg tcgtgactgg gaaaaccctg gcgttaccca  2400
acttaatcgc cttgcagcac atcccccttt cgccagctgg cgtaatagcg aagaggcccg  2460
caccgatcgc ccttcccaac agttgcgcag cctgaatggc gaatgggacg cgccctgtag  2520
cggcgcatta agcgcggcgg gtgtggtggt tacgcgcagc gtgaccgcta cacttgccag  2580
cgccctagcg cccgctcctt tcgctttctt cccttccttt ctcgccacgt tcgccggctt  2640
tccccgtcaa gctctaaatc gggggctccc tttagggttc cgatttagtg ctttacggca  2700
cctcgacccc aaaaaacttg attagggtga tggttcacgt agtgggccat cgccctgata  2760
gacggttttt cgccctttga cgttggagtc cacgttcttt aatagtggac tcttgttcca  2820
aactggaaca acactcaacc ctatctcggt ctattctttt gatttataag ggattttgcc  2880
gatttcggcc tattggttaa aaaatgagct gatttaacaa aaatttaacg cgaattttaa  2940
caaaatatta acgcttacaa tttaggtggc acttttcggg gaaatgtgcg cggaacccct  3000
atttgtttat ttttctaaat acattcaaat atgtatccgc tcatgagaca ataaccctga  3060
taaatgcttc aataatattg aaaaaggaag agtatgagta ttcaacattt ccgtgtcgcc  3120
cttattccct tttttgcggc attttgcctt cctgtttttg ctcacccaga aacgctggtg  3180
aaagtaaaag atgctgaaga tcagttgggt gcacgagtgg gttacatcga actggatctc  3240
aacagcggta agatccttga gagttttcgc cccgaagaac gttttccaat gatgagcact  3300
tttaaagttc tgctatgtgg cgcggtatta tcccgtattg acgccgggca agagcaactc  3360
ggtcgccgca tacactattc tcagaatgac ttggttgagt actcaccagt cacagaaaag  3420
catcttacgg atggcatgac agtaagagaa ttatgcagtg ctgccataac catgagtgat  3480
aacactgcgg ccaacttact tctgacaacg atcggaggac cgaaggagct aaccgctttt  3540
ttgcacaaca tgggggatca tgtaactcgc cttgatcgtt gggaaccgga gctgaatgaa  3600
gccataccaa acgacgagcg tgacaccacg atgcctgtag caatggcaac aacgttgcgc  3660
aaactattaa ctggcgaact acttactcta gcttcccggc aacaattaat agactggatg  3720
gaggcggata aagttgcagg accacttctg cgctcggccc ttccggctgg ctggtttatt  3780
gctgataaat ctggagccgg tgagcgtggg tctcgcggta tcattgcagc actggggcca  3840
gatggtaagc cctcccgtat cgtagttatc tacacgacgg ggagtcaggc aactatggat  3900
gaacgaaata gacagatcgc tgagataggt gcctcactga ttaagcattg gtaactgtca  3960
gaccaagttt actcatatat actttagatt gatttaaaac ttcattttta atttaaaagg  4020
atctaggtga agatcctttt tgataatctc atgaccaaaa tcccttaacg tgagttttcg  4080
ttccactgag cgtcagaccc cgtagaaaag atcaaaggat cttcttgaga tccttttttt  4140
ctgcgcgtaa tctgctgctt gcaaacaaaa aaaccaccgc taccagcggt ggtttgtttg  4200
ccggatcaag agctaccaac tctttttccg aaggtaactg gcttcagcag agcgcagata  4260
ccaaatactg ttcttctagt gtagccgtag ttaggccacc acttcaagaa ctctgtagca  4320
ccgcctacat acctcgctct gctaatcctg ttaccagtgg ctgctgccag tggcgataag  4380
tcgtgtctta ccgggttgga ctcaagacga tagttaccgg ataaggcgca gcggtcgggc  4440
tgaacggggg gttcgtgcac acagcccagc ttggagcgaa cgacctacac cgaactgaga  4500
tacctacagc gtgagctatg agaaagcgcc acgcttcccg aagggagaaa ggcggacagg  4560
tatccggtaa gcggcagggt cggaacagga gagcgcacga gggagcttcc agggggaaac  4620
gcctggtatc tttatagtcc tgtcgggttt cgccacctct gacttgagcg tcgatttttg  4680
tgatgctcgt caggggggcg gagcctatgg aaaaacgcca gcaacgcggc ctttttacgg  4740
ttcctggcct tttgctggcc ttttgctcac atgttctttc ctgcgttatc ccctgattct  4800
gtggataacc gtattaccgc ctttgagtga gctgataccg ctcgccgcag ccgaacgacc  4860
gagcgcagcg agtcagtgag cgaggaagcg gaagagcgcc caatacgcaa accgcctctc  4920
cccgcgcgtt ggccgattca ttaatgcagc tggcacgaca ggtttcccga ctggaaagcg  4980
ggcagtgagc gcaacgcaat taatgtgagt tagctcactc attaggcacc ccaggcttta  5040
cactttatgc ttccggctcg tatgttgtgt ggaattgtga gcggataaca atttcacaca  5100
ggaaacagct atgaccatga ttacgccaga tttaattaag g                      5141

SEQ ID NO: 24          moltype = DNA  length = 6071
FEATURE                Location/Qualifiers
misc_feature           1..6071
                       note = constructed sequence
source                 1..6071
                       mol_type = other DNA
                       organism = synthetic construct
SEQUENCE: 24
ctgcgcgctc gctcgctcac tgaggccgcc cgggcaaagc ccgggcgtcg ggcgaccttt  60
ggtcgcccgg cctcagtgag cgagcgagcg cgcagagagg gagtggccaa ctccatcact  120
aggggttcct tgtagttaat gattaacccg ccatgctact tatctacgta gccatgctct  180
aggaagatcg gaattcgccc ttaagctagg ggggatccac tagtactcga gacctaggag  240
ttaattttta aaaagcagtc aaaagtccaa gtgcccttgc gagcatttac tctctctgtt  300
tgctctggtt aataatctca ggagcacaaa cattccttac tagttctagg agttaatttt  360
taaaaagcag tcaaaagtcc aagtgccctt gcgagcattt actctctctg tttgctctgg  420
ttaataatct caggagcaca aacattcctt actagttcta gagcggccgc cagtgtgctg  480
gaattcggct tttttagggc tggaagctac ctttgacatc atttcctctg cgaatgcatg  540
tataatttct acagaaccta ttagaaagga tcacccagcc tctgcttttg tacaactttc  600
ccttaaaaaa ctgccaatcc cactgctgtt tggcccaata gtgagaactt tttcctgctg  660
cctcttggtg cttttgccta tggcccctat tctgcctgct gaagacactc ttgccagcat  720
ggacttaaac ccctccagct ctgacaatcc tctttctctt ttgttttaca tgaagggtct  780
ggcagccaaa gcaatcactc aaagttcaaa ccttatcatt ttttgctttg ttcctcttgg  840
ccttggtttt gtacatcagc tttgaaaata ccatcccagg gttaatgctg gggttaattt  900
ataactgaga gtgctctagt tctgcaatac aggacatgct ataaaaatgg aaagatgttg  960
ctttctgaga gatcagctta cttgtggtac cgagctcgga tcctgagaac ttcagggtga  1020
gtctatggga cccttgatgt tttctttccc cttcttttct atggttaagt tcatgtcata  1080
```

-continued ggaaggggag aagtaacagg gtacacatat tgaccaaatc agggtaattt tgcatttgta 1140
attttaaaaa atgctttctt cttttaatat acttttttgt ttatcttatt tctaatactt 1200
tccctaatct ctttctttca gggcaataat gatacaatgt atcatgcctc tttgcaccat 1260
tctaaagaat aacagtgata atttctgggt taaggcaata gcaatatttc tgcatataaa 1320
tatttctgca tataaattgt aactgatgta agaggtttca tattgctaat agcagctaca 1380
atccagctac cattctgctt ttattttatg gttgggataa ggctggatta ttctgagtcc 1440
aagctaggcc cttttgctaa tcatgttcat acctcttatc ttcctcccac agctcctggg 1500
caacgtgctg gtctgtgtgc tggcccatca ctttggcaaa gaattgatct cgagtaactg 1560
aaggcggccg ccaccatgag cagcaagggc tctgtggtgc tggcctactc tggcggcctg 1620
gacaccagct gtatcctcgt gtggctgaaa gaacagggct acgacgtgat cgcctacctg 1680
gccaacatcg gccagaaaga ggacttcgag gaagcccgga agaaggccct gaagctgggc 1740
gccaagaagg tgttcatcga ggacgtgtcc cgcgagttcg tggaagagtt catctggccc 1800
gccatccaga gcagcgccct gtacgaggac agatacctgc tgggcaccag cctggccaga 1860
ccctgtatcg cccggaaaca ggtggaaatc gcccagcgcg agggcgccaa atacgtgtct 1920
cacggcgcca ccggcaaggg caacgaccag gtgcgctttg agctgagctg ctactccctg 1980
gccccccaga tcaaagtgat cgccccttgg cggatgcccg agttctacaa ccggttcaag 2040
ggccggaacg acctgatgga atacgccaag cagcacggca tccccatccc cgtgaccccc 2100
aagaaccctt ggagcatgga cgagaacctg atgcacatca gctacgaggc cggcatcctg 2160
gaaaacccca agaatcaggc cctcccggc ctgtacacaa agacccagga ccctgccaag 2220
gcccccaaca cccccgacat tctggaaatc gagttcaaga aaggcgtgcc cgtgaaagtg 2280
accaacgtga aggacggcac cacccaccag acctccctgg aactgttcat gtacctgaac 2340
gaggtggccg gcaagcacgg cgtgggcaga atcgacatcg tggaaaacag attcatcggc 2400
atgaagtccc ggggcatcta cgagacacca gccggcacca tcctgtacca cgcccacctg 2460
gatatcgagg ccttcaccat ggaccgggaa gtgcggaaga tcaagcaggg cctgggcctg 2520
aagttcgccg agctggtgta cacaggcttt tggcacagcc ccgagtgcga gtttgtgcgg 2580
cactgcattg ccaagagcca ggaacgggtg gaaggcaagg tgcaggtgtc cgtgctgaag 2640
ggccaggtgt acattctggg cagagagagc cccctgagcc tgtacaacga ggaactggtg 2700
tctatgaacg tgcagggcga ctacgagccc accgacgcca ccggcttcat caacatcaac 2760
agcctgagac tgaaagagta ccaccggctg cagtccaaag tgaccgccaa gtgataagca 2820
tgcggatctg cctcgactgt gccttctagt tgccagccat ctgttgtttg cccctccccc 2880
gtgccttcct tgaccctgga aggtgccact cccactgtcc tttcctaata aaatgaggaa 2940
attgcatcgc attgtctgag taggtgtcat tctattctgg ggggtggggt ggggcaggac 3000
agcaaggggg aggattggga agacaatagc aggcatgctg gggactcgag ttaagggcga 3060
attcccgatt aggatcttcc tagagcatgg ctacgtagat aagtagcatg gcgggttaat 3120
cattaactac aaggaacccc tagtgatgga gttggccact ccctctctgc gcgctcgctc 3180
gctcactgag gccgggcgac caaaggtcgc ccgacgcccg ggctttgccc gggcggcctc 3240
agtgagcgag cgagcgcgca gccttaatta acctaattca ctggccgtcg ttttacaacg 3300
tcgtgactgg gaaaaccctg gcgttaccca acttaatcgc cttgcagcac atcccccttt 3360
cgccagctgg cgtaatagcg aagaggcccg caccgatcgc ccttcccaac agttgcgcag 3420
cctgaatggc gaatgggacg cgccctgtag cggcgcatta agcgcggcgg gtgtggtggt 3480
tacgcgcagc gtgaccgcta cacttgccag cgccctagcg cccgctcctt tcgctttctt 3540
cccttccttt ctcgccacgt tcgccggctt tccccgtcaa gctctaaatc gggggctccc 3600
tttagggttc cgatttagtg ctttacggca cctcgacccc aaaaaacttg attagggtga 3660
tggttcacgt agtgggccat cgccctgata gacggttttt cgccctttga cgttggagtc 3720
cacgttcttt aatagtggac tcttgttcca aactggaaca acactcaacc ctatctcggt 3780
ctattctttt gatttataag ggattttgcc gatttcggcc tattggttaa aaaatgagct 3840
gatttaacaa aaatttaacg cgaattttaa caaaatatta acgcttacaa tttaggtggc 3900
acttttcggg gaaatgtgcg cggaacccct atttgtttat ttttctaaat acattcaaat 3960
atgtatccgc tcatgagaca ataaccctga taaatgcttc aataatattg aaaaaggaag 4020
agtatgagta ttcaacattt ccgtgtcgcc cttattccct tttttgcggc attttgcctt 4080
cctgtttttg ctcacccaga aacgctggtg aaagtaaaag atgctgaaga tcagttgggt 4140
gcacgagtgg gttacatcga actggatctc aacagcggta agatccttga gagttttcgc 4200
cccgaagaac gttttccaat gatgagcact tttaaagttc tgctatgtgg cgcggtatta 4260
tcccgtattg acgccgggca agagcaactc ggtcgccgca tacactattc tcagaatgac 4320
ttggttgagt actcaccagt cacagaaaag catcttacgg atggcatgac agtaagagaa 4380
ttatgcagtg ctgccataac catgagtgat aacactgcgg ccaacttact tctgacaacg 4440
atcggaggac cgaaggagct aaccgctttt ttgcacaaca tgggggatca tgtaactcgc 4500
cttgatcgtt gggaaccgga gctgaatgaa gccataccaa acgacgagcg tgacaccacg 4560
atgcctgtag caatggcaac aacgttgcgc aaactattaa ctggcgaact acttactcta 4620
gcttcccggc aacaattaat agactggatg gaggcggata aagttgcagg accacttctg 4680
cgctcggccc ttccggctgg ctggtttatt gctgataaat ctggagccgg tgagcgtggg 4740
tctcgcggta tcattgcagc actggggcca gatggtaagc cctcccgtat cgtagttatc 4800
tacacgacgg ggagtcaggc aactatggat gaacgaaata gacagatcgc tgagataggt 4860
gcctcactga ttaagcattg gtaactgtca gaccaagttt actcatatat actttagatt 4920
gatttaaaac ttcattttta atttaaaagg atctaggtga agatcctttt tgataatctc 4980
atgaccaaaa tcccttaacg tgagttttcg ttccactgag cgtcagaccc cgtagaaaag 5040
atcaaaggat cttcttgaga tccttttttt ctgcgcgtaa tctgctgctt gcaaacaaaa 5100
aaaccaccgc taccagcggt ggtttgtttg ccggatcaag agctaccaac tctttttccg 5160
aaggtaactg gcttcagcag agcgcagata ccaaatactg ttcttctagt gtagccgtag 5220
ttaggccacc acttcaagaa ctctgtagca ccgcctacat acctcgctct gctaatcctg 5280
ttaccagtgg ctgctgccag tggcgataag tcgtgtctta ccgggttgga ctcaagacga 5340
tagttaccgg ataaggcgca gcggtcgggc tgaacggggg gttcgtgcac acagcccagc 5400
ttggagcgaa cgacctacac cgaactgaga tacctacagc gtgagctatg agaaagcgcc 5460
acgcttcccg aagggagaaa ggcggacagg tatccggtaa gcggcagggt cggaacagga 5520
gagcgcacga gggagcttcc agggggaaac gcctggtatc tttatagtcc tgtcgggttt 5580
cgccacctct gacttgagcg tcgatttttg tgatgctcgt caggggggcg gagcctatgg 5640
aaaaacgcca gcaacgcggc ctttttacgg ttcctggcct tttgctggcc ttttgctcac 5700
atgttctttc ctgcgttatc ccctgattct gtggataacc gtattaccgc ctttgagtga 5760
gctgataccg ctcgccgcag ccgaacgacc gagcgcagcg agtcagtgag cgaggaagcg 5820

-continued

```
gaagagcgcc caatacgcaa accgcctctc cccgcgcgtt ggccgattca ttaatgcagc  5880
tggcacgaca ggtttcccga ctggaaagcg ggcagtgagc gcaacgcaat taatgtgagt  5940
tagctcactc attaggcacc ccaggcttta cactttatgc ttccggctcg tatgttgtgt  6000
ggaattgtga gcggataaca atttcacaca ggaaacagct atgaccatga ttacgccaga  6060
tttaattaag g                                                       6071

SEQ ID NO: 25          moltype = DNA  length = 6135
FEATURE                Location/Qualifiers
misc_feature           1..6135
                       note = constructed sequence
source                 1..6135
                       mol_type = other DNA
                       organism = synthetic construct
SEQUENCE: 25
ctgcgcgctc gctcgctcac tgaggccgcc cgggcaaagc ccgggcgtcg ggcgaccttt  60
ggtcgcccgg cctcagtgag cgagcgagcg cgcagagagg gagtggccaa ctccatcact  120
aggggttcct tgtagttaat gattaacccg ccatgctact tatctacgta gccatgctct  180
aggaagatcg gaattcgccc ttaagctagc aggttaattt ttaaaaagca gtcaaaagtc  240
caagtggccc ttggcagcat ttactctctc tgtttgctct ggttaataat ctcaggagca  300
caaacattcc agatccaggt taatttttaa aaagcagtca aaagtccaag tggcccttgg  360
cagcatttac tctctctgtt tgctctggtt aataatctca ggagcacaaa cattccagat  420
ccggcgcgcc agggctggaa gctacctttg acatcatttc ctctgcgaat gcatgtataa  480
tttctacaga acctattaga aaggatcacc cagcctctgc ttttgtacaa ctttccctta  540
aaaaactgcc aattccactg ctgtttggcc caatagtgag aactttttcc tgctgcctct  600
tggtgctttt gcctatggcc cctattctgc ctgctgaaga cactcttgcc agcatggact  660
taaacccctc cagctctgac aatcctcttt ctcttttgtt ttacatgaag ggtctggcag  720
ccaaagcaat cactcaaagt tcaaacctta tcattttttg ctttgttcct cttggccttg  780
gttttgtaca tcagctttga aaataccatc ccagggttaa tgctggggtt aatttataac  840
taagagtgct ctagttttgc aatacaggac atgctataaa aatggaaaga tgttgctttc  900
tgagagactg cagaagttgg tcgtgaggca ctgggcaggt aagtatcaag gttacaagac  960
aggtttaagg agaccaatag aaactgggct tgtcgagaca gagaagactc ttgcgtttct  1020
gataggcacc tattggtctt actgacatcc actttgcctt tctctccaca ggtgtccagg  1080
cggccgccac catgagcagc aagggctctg tggtgctggc ctactctggc ggcctggaca  1140
ccagctgtat cctcgtgtgg ctgaaagaac agggctacga cgtgatcgcc tacctggcca  1200
acatcggcca gaaagaggac ttcgaggaag cccggaagaa ggccctgaag ctgggcgcca  1260
agaaggtgtt catcgaggac gtgtcccgcg agttcgtgga agagttcatc tggcccgcca  1320
tccagagcag cgccctgtac gaggacagat acctgctggg caccagcctg gccagaccct  1380
gtatcgcccg gaaacaggtg gaaatcgccc agcgcgaggg cgccaaatac gtgtctcacg  1440
gcgccaccgg caagggcaac gaccaggtgc gctttgagct gagctgctac tccctggccc  1500
cccagatcaa agtgatcgcc ccttggcgga tgcccgagtt ctacaaccgg ttcaagggcc  1560
ggaacgacct gatggaatac gccaagcagc acggcatccc catccccgtg acccccaaga  1620
acccttggag catggacgag aacctgatgc acatcagcta cgaggccggc atcctggaaa  1680
accccaagaa tcaggcccct cccggcctgt acacaaagac ccaggaccct gccaaggccc  1740
ccaacacccc cgacattctg gaaatcgagt tcaagaaagg cgtgcccgtg aaagtgacca  1800
acgtgaagga cggcaccacc caccagacct ccctggaact gttcatgtac ctgaacgagg  1860
tggccggcaa gcacggcgtg ggcagaatcg acatcgtgga aaacagattc atcggcatga  1920
agtcccgggg catctacgag acaccagccg gcaccatcct gtaccacgcc cacctggata  1980
tcgaggcctt caccatggac cgggaagtgc ggaagatcaa gcagggcctg ggcctgaagt  2040
tcgccgagct ggtgtacaca ggcttttggc acagccccga gtgcgagttt gtgcggcact  2100
gcattgccaa gagccaggaa cgggtggaag gcaaggtgca ggtgtccgtg ctgaagggcc  2160
aggtgtacat tctgggcaga gagagccccc tgagcctgta caacgaggaa ctggtgtcta  2220
tgaacgtgca gggcgactac gagcccaccg acgccaccgg cttcatcaac atcaacagcc  2280
tgagactgaa agagtaccac cggctgcagt ccaaagtgac cgccaagtga taagcatgcg  2340
gatccaatca acctctggat tacaaaattt gtgaaagatt gactggtatt cttaactatg  2400
ttgctccttt tacgctatgt ggatacgctg ctttaatgcc tttgtatcat gctattgctt  2460
cccgtatggc tttcattttc tcctccttgt ataaatcctg gttgctgtct ctttatgagg  2520
agttgtggcc cgttgtcagg caacgtggcg tggtgtgcac tgtgtttgct gacgcaaccc  2580
ccactggttg gggcattgcc accacctgtc agctcctttc cgggactttc gctttccccc  2640
tccctattgc cacggcggaa ctcatcgccg cctgccttgc ccgctgctgg acaggggctc  2700
ggctgttggg cactgacaat tccgtggtgt tgtcggggaa gctgacgtcc tttccatggc  2760
tgctcgcctg tgttgccacc tggattctgc gcgggacgtc cttctgctac gtcccttcgg  2820
ccctcaatcc agcggacctt ccttcccgcg gcctgctgcc ggctctgcgg cctcttccgc  2880
gtcttcgaga tctgcctcga ctgtgccttc tagttgccag ccatctgttg tttgcccctc  2940
ccccgtgcct tccttgaccc tggaaggtgc cactcccact gtcctttcct aataaaatga  3000
ggaaattgca tcgcattgtc tgagtaggtg tcattctatt ctggggggtg gggtggggca  3060
ggacagcaag ggggaggatt gggaagacaa tagcaggcat gctggggact cgagttaagg  3120
gcgaattccc gattaggatc ttcctagagc atggctacgt agataagtag catggcgggt  3180
taatcattaa ctacaaggaa cccctagtga tggagttggc cactccctct ctgcgcgctc  3240
gctcgctcac tgaggccggg cgaccaaagg tcgcccgacg cccgggcttt gcccgggcgg  3300
cctcagtgag cgagcgagcg cgcagcctta attaacctaa ttcactggcc gtcgttttac  3360
aacgtcgtga ctgggaaaac cctggcgtta cccaacttaa tcgccttgca gcacatcccc  3420
ctttcgccag ctggcgtaat agcgaagagg cccgcaccga tcgcccttcc caacagttgc  3480
gcagcctgaa tggcgaatgg gacgcgccct gtagcggcgc attaagcgcg gcgggtgtgg  3540
tggttacgcg cagcgtgacc gctacacttg ccagcgccct agcgcccgct cctttcgctt  3600
tcttcccttc ctttctcgcc acgttcgccg gctttccccg tcaagctcta aatcgggggc  3660
tccctttagg gttccgattt agtgctttac ggcacctcga ccccaaaaaa cttgattagg  3720
gtgatggttc acgtagtggg ccatcgccct gatagacggt ttttcgccct ttgacgttgg  3780
agtccacgtt ctttaatagt ggactcttgt tccaaactgg aacaacactc aaccctatct  3840
cggtctattc ttttgattta taagggattt tgccgatttc ggcctattgg ttaaaaaatg  3900
```

-continued

```
agctgattta acaaaaattt aacgcgaatt ttaacaaaat attaacgctt acaatttagg  3960
tggcactttt cggggaaatg tgcgcggaac ccctatttgt ttatttttct aaatacattc  4020
aaatatgtat ccgctcatga gacaataacc ctgataaatg cttcaataat attgaaaaag  4080
gaagagtatg agtattcaac atttccgtgt cgcccttatt cccttttttg cggcattttg  4140
ccttcctgtt tttgctcacc cagaaacgct ggtgaaagta aaagatgctg aagatcagtt  4200
gggtgcacga gtgggttaca tcgaactgga tctcaacagc ggtaagatcc ttgagagttt  4260
tcgccccgaa gaacgttttc caatgatgag cacttttaaa gttctgctat gtggcgcggt  4320
attatcccgt attgacgccg ggcaagagca actcggtcgc cgcatacact attctcagaa  4380
tgacttggtt gagtactcac cagtcacaga aaagcatctt acggatggca tgacagtaag  4440
agaattatgc agtgctgcca taaccatgag tgataacact gcggccaact tacttctgac  4500
aacgatcgga ggaccgaagg agctaaccgc ttttttgcac aacatggggg atcatgtaac  4560
tcgccttgat cgttgggaac cggagctgaa tgaagccata ccaaacgacg agcgtgacac  4620
cacgatgcct gtagcaatgg caacaacgtt gcgcaaacta ttaactggcg aactacttac  4680
tctagcttcc cggcaacaat taatagactg gatggaggcg gataaagttg caggaccact  4740
tctgcgctcg gcccttccgg ctggctggtt tattgctgat aaatctggag ccggtgagcg  4800
tgggtctcgc ggtatcattg cagcactggg gccagatggt aagccctccc gtatcgtagt  4860
tatctacacg acggggagtc aggcaactat ggatgaacga aatagacaga tcgctgagat  4920
aggtgcctca ctgattaagc attggtaact gtcagaccaa gtttactcat atatacttta  4980
gattgattta aaacttcatt tttaatttaa aaggatctag gtgaagatcc tttttgataa  5040
tctcatgacc aaaatccctt aacgtgagtt ttcgttccac tgagcgtcag accccgtaga  5100
aaagatcaaa ggatcttctt gagatccttt ttttctgcgc gtaatctgct gcttgcaaac  5160
aaaaaaacca ccgctaccag cggtggtttg tttgccggat caagagctac caactctttt  5220
tccgaaggta actggcttca gcagagcgca gataccaaat actgttcttc tagtgtagcc  5280
gtagttaggc caccacttca agaactctgt agcaccgcct acatacctcg ctctgctaat  5340
cctgttacca gtggctgctg ccagtggcga taagtcgtgt cttaccgggt tggactcaag  5400
acgatagtta ccggataagg cgcagcggtc gggctgaacg gggggttcgt gcacacagcc  5460
cagcttggag cgaacgacct acaccgaact gagataccta cagcgtgagc tatgagaaag  5520
cgccacgctt cccgaaggga gaaaggcgga caggtatccg gtaagcggca gggtcggaac  5580
aggagagcgc acgagggagc ttccaggggg aaacgcctgg tatctttata gtcctgtcgg  5640
gtttcgccac ctctgacttg agcgtcgatt tttgtgatgc tcgtcagggg ggcggagcct  5700
atggaaaaac gccagcaacg cggccttttt acggttcctg gccttttgct ggccttttgc  5760
tcacatgttc tttcctgcgt tatcccctga ttctgtggat aaccgtatta ccgcctttga  5820
gtgagctgat accgctcgcc gcagccgaac gaccgagcgc agcgagtcag tgagcgagga  5880
agcggaagag cgcccaatac gcaaaccgcc tctccccgcg cgttggccga ttcattaatg  5940
cagctggcac gacaggtttc ccgactggaa agcgggcagt gagcgcaacg caattaatgt  6000
gagttagctc actcattagg caccccaggc tttacacttt atgcttccgg ctcgtatgtt  6060
gtgtggaatt gtgagcggat aacaatttca cacaggaaac agctatgacc atgattacgc  6120
cagatttaat taagg                                                   6135

SEQ ID NO: 26          moltype = DNA  length = 5587
FEATURE                Location/Qualifiers
misc_feature           1..5587
                       note = constructed sequence
source                 1..5587
                       mol_type = other DNA
                       organism = synthetic construct
SEQUENCE: 26
ctgcgcgctc gctcgctcac tgaggccgcc cgggcaaagc ccgggcgtcg ggcgaccttt  60
ggtcgcccgg cctcagtgag cgagcgagcg cgcagagagg gagtggccaa ctccatcact  120
aggggttcct tgtagttaat gattaacccg ccatgctact tatctacgta gccatgctct  180
aggaagatcg gaattcgccc ttaagctagc aggttaattt ttaaaaagca gtcaaaagtc  240
caagtggccc ttggcagcat ttactctctc tgtttgctct ggttaataat ctcaggagca  300
caaacattcc agatccaggt taatttttaa aaagcagtca aaagtccaag tggcccttgg  360
cagcatttac tctctctgtt tgctctggtt aataatctca ggagcacaaa cattccagat  420
ccggcgcgcc agggctggaa gctacctttg acatcatttc ctctgcgaat gcatgtataa  480
tttctacaga acctattaga aaggatcacc cagcctctgc ttttgtacaa ctttccctta  540
aaaaactgcc aattccactg ctgtttggcc caatagtgag aactttttcc tgctgcctct  600
tggtgctttt gcctatggcc cctattctgc ctgctgaaga cactcttgcc agcatggact  660
taaacccctc cagctctgac aatcctcttt ctcttttgtt ttacatgaag ggtctggcag  720
ccaaagcaat cactcaaagt tcaaacctta tcattttttg ctttgttcct cttggccttg  780
gttttgtaca tcagctttga aaataccatc ccagggttaa tgctggggtt aatttataac  840
taagagtgct ctagttttgc aatacaggac atgctataaa aatggaaaga tgttgctttc  900
tgagagactg cagaagttgg tcgtgaggca ctgggcaggt aagtatcaag gttacaagac  960
aggtttaagg agaccaatag aaactgggct tgtcgagaca gagaagactc ttgcgtttct  1020
gataggcacc tattggtctt actgacatcc actttgcctt tctctccaca ggtgtccagg  1080
cggccgccac catgagcagc aagggctctg tggtgctggc ctactctggc ggcctggaca  1140
ccagctgtat cctcgtgtgg ctgaaagaac agggctacga cgtgatcgcc tacctggcca  1200
acatcggcca gaaagaggac ttcgaggaag cccggaagaa ggccctgaag ctgggcgcca  1260
agaaggtgtt catcgaggac gtgtcccgcg agttcgtgga agagttcatc tggcccgcca  1320
tccagagcag cgccctgtac gaggacagat acctgctggg caccagcctg gccagaccct  1380
gtatcgcccg gaaacaggtg gaaatcgccc agcgcgaggg cgccaaatac gtgtctcacg  1440
gcgccaccgg caagggcaac gaccaggtgc gctttgagct gagctgctac tccctggccc  1500
cccagatcaa agtgatcgcc ccttggcgga tgcccgagtt ctacaaccgg ttcaagggcc  1560
ggaacgacct gatggaatac gccaagcagc acggcatccc catccccgtg acccccaaga  1620
acccttggag catggacgag aacctgatgc acatcagcta cgaggccggc atcctggaaa  1680
accccaagaa tcaggcccct cccggcctgt acacaaagac ccaggaccct gccaaggccc  1740
ccaacacccc cgacattctg gaaatcgagt tcaagaaagg cgtgcccgtg aaagtgacca  1800
acgtgaagga cggcaccacc caccagacct ccctggaact gttcatgtac ctgaacgagg  1860
tggccggcaa gcacggcgtg ggcagaatcg acatcgtgga aaacagattc atcggcatga  1920
```

-continued

```
agtcccgggg catctacgag acaccagccg gcaccatcct gtaccacgcc cacctggata  1980
tcgaggcctt caccatggac cgggaagtgc ggaagatcaa gcagggcctg ggcctgaagt  2040
tcgccgagct ggtgtacaca ggcttttggc acagccccga gtgcgagttt gtgcggcact  2100
gcattgccaa gagccaggaa cgggtggaag gcaaggtgca ggtgtccgtg ctgaagggcc  2160
aggtgtacat tctgggcaga gagagccccc tgagcctgta caacgaggaa ctggtgtcta  2220
tgaacgtgca gggcgactac gagcccaccg acgccaccgg cttcatcaac atcaacagcc  2280
tgagactgaa agagtaccac cggctgcagt ccaaagtgac cgccaagtga taagcatgcg  2340
gatctgcctc gactgtgcct tctagttgcc agccatctgt tgtttgcccc tcccccgtgc  2400
cttccttgac cctggaaggt gccactccca ctgtcctttc ctaataaaat gaggaaattg  2460
catcgcattg tctgagtagg tgtcattcta ttctgggggg tggggtgggg caggacagca  2520
agggggagga ttgggaagac aatagcaggc atgctgggga ctcgagttaa gggcgaattc  2580
ccgattagga tcttcctaga gcatggctac gtagataagt agcatggcgg gttaatcatt  2640
aactacaagg aacccctagt gatggagttg gccactccct ctctgcgcgc tcgctcgctc  2700
actgaggccg ggcgaccaaa ggtcgcccga cgcccgggct ttgcccgggc ggcctcagtg  2760
agcgagcgag cgcgcagcct taattaacct aattcactgg ccgtcgtttt acaacgtcgt  2820
gactgggaaa accctggcgt tacccaactt aatcgccttg cagcacatcc ccctttcgcc  2880
agctggcgta atagcgaaga ggcccgcacc gatcgccctt cccaacagtt gcgcagcctg  2940
aatggcgaat gggacgcgcc ctgtagcggc gcattaagcg cggcgggtgt ggtggttacg  3000
cgcagcgtga ccgctacact tgccagcgcc ctagcgcccg ctcctttcgc tttcttccct  3060
tcctttctcg ccacgttcgc cggctttccc cgtcaagctc taaatcgggg gctcccttta  3120
gggttccgat ttagtgcttt acggcacctc gaccccaaaa aacttgatta gggtgatggt  3180
tcacgtagtg ggccatcgcc ctgatagacg gtttttcgcc ctttgacgtt ggagtccacg  3240
ttctttaata gtggactctt gttccaaact ggaacaacac tcaaccctat ctcggtctat  3300
tcttttgatt tataagggat tttgccgatt tcggcctatt ggttaaaaaa tgagctgatt  3360
taacaaaaat ttaacgcgaa ttttaacaaa atattaacgc ttacaattta ggtggcactt  3420
ttcggggaaa tgtgcgcgga acccctattt gtttattttt ctaaatacat tcaaatatgt  3480
atccgctcat gagacaataa ccctgataaa tgcttcaata atattgaaaa aggaagagta  3540
tgagtattca acatttccgt gtcgccctta ttcccttttt tgcggcattt tgccttcctg  3600
tttttgctca cccagaaacg ctggtgaaag taaaagatgc tgaagatcag ttgggtgcac  3660
gagtgggtta catcgaactg gatctcaaca gcggtaagat ccttgagagt tttcgccccg  3720
aagaacgttt tccaatgatg agcactttta aagttctgct atgtggcgcg gtattatccc  3780
gtattgacgc cgggcaagag caactcggtc gccgcataca ctattctcag aatgacttgg  3840
ttgagtactc accagtcaca gaaaagcatc ttacggatgg catgacagta agagaattat  3900
gcagtgctgc cataaccatg agtgataaca ctgcggccaa cttacttctg acaacgatcg  3960
gaggaccgaa ggagctaacc gcttttttgc acaacatggg ggatcatgta actcgccttg  4020
atcgttggga accggagctg aatgaagcca taccaaacga cgagcgtgac accacgatgc  4080
ctgtagcaat ggcaacaacg ttgcgcaaac tattaactgg cgaactactt actctagctt  4140
cccggcaaca attaatagac tggatggagg cggataaagt tgcaggacca cttctgcgct  4200
cggcccttcc ggctggctgg tttattgctg ataaatctgg agccggtgag cgtgggtctc  4260
gcggtatcat tgcagcactg gggccagatg gtaagccctc ccgtatcgta gttatctaca  4320
cgacggggag tcaggcaact atggatgaac gaaatagaca gatcgctgag ataggtgcct  4380
cactgattaa gcattggtaa ctgtcagacc aagtttactc atatatactt tagattgatt  4440
taaaacttca tttttaattt aaaaggatct aggtgaagat cctttttgat aatctcatga  4500
ccaaaatccc ttaacgtgag ttttcgttcc actgagcgtc agaccccgta gaaaagatca  4560
aaggatcttc ttgagatcct ttttttctgc gcgtaatctg ctgcttgcaa acaaaaaaac  4620
caccgctacc agcggtggtt tgtttgccgg atcaagagct accaactctt tttccgaagg  4680
taactggctt cagcagagcg cagataccaa atactgttct tctagtgtag ccgtagttag  4740
gccaccactt caagaactct gtagcaccgc ctacatacct cgctctgcta atcctgttac  4800
cagtggctgc tgccagtggc gataagtcgt gtcttaccgg gttggactca agacgatagt  4860
taccggataa ggcgcagcgg tcgggctgaa cggggggttc gtgcacacag cccagcttgg  4920
agcgaacgac ctacaccgaa ctgagatacc tacagcgtga gctatgagaa agcgccacgc  4980
ttcccgaagg gagaaaggcg gacaggtatc cggtaagcgg cagggtcgga acaggagagc  5040
gcacgaggga gcttccaggg ggaaacgcct ggtatcttta tagtcctgtc gggtttcgcc  5100
acctctgact tgagcgtcga tttttgtgat gctcgtcagg ggggcggagc ctatggaaaa  5160
acgccagcaa cgcggccttt ttacggttcc tggccttttg ctggcctttt gctcacatgt  5220
tctttcctgc gttatcccct gattctgtgg ataaccgtat taccgccttt gagtgagctg  5280
ataccgctcg ccgcagccga acgaccgagc gcagcgagtc agtgagcgag gaagcggaag  5340
agcgcccaat acgcaaaccg cctctccccg cgcgttggcc gattcattaa tgcagctggc  5400
acgacaggtt tcccgactgg aaagcgggca gtgagcgcaa cgcaattaat gtgagttagc  5460
tcactcatta ggcaccccag gctttacact ttatgcttcc ggctcgtatg ttgtgtggaa  5520
ttgtgagcgg ataacaattt cacacaggaa acagctatga ccatgattac gccagattta  5580
attaagg                                                            5587

SEQ ID NO: 27          moltype = DNA  length = 5587
FEATURE                Location/Qualifiers
misc_feature           1..5587
                       note = constructed sequence
source                 1..5587
                       mol_type = other DNA
                       organism = synthetic construct
SEQUENCE: 27
ctgcgcgctc gctcgctcac tgaggccgcc cgggcaaagc ccgggcgtcg ggcgaccttt  60
ggtcgcccgg cctcagtgag cgagcgagcg cgcagagagg gagtggccaa ctccatcact  120
aggggttcct tgtagttaat gattaacccg ccatgctact tatctacgta gccatgctct  180
aggaagatcg gaattcgccc ttaagctagc aggttaattt ttaaaaagca gtcaaaagtc  240
caagtggccc ttggcagcat ttactctctc tgtttgctct ggttaataat ctcaggagca  300
caaacattcc agatccaggt taatttttaa aaagcagtca aaagtccaag tggcccttgg  360
cagcatttac tctctctgtt tgctctggtt aataatctca ggagcacaaa cattccagat  420
ccggcgcgcc agggctggaa gctacctttg acatcatttc ctctgcgaat gcatgtataa  480
```

-continued

```
tttctacaga acctattaga aaggatcacc cagcctctgc ttttgtacaa ctttccctta  540
aaaaactgcc aattccactg ctgtttggcc caatagtgag aactttttcc tgctgcctct  600
tggtgctttt gcctatggcc cctattctgc ctgctgaaga cactcttgcc agcatggact  660
taaacccctc cagctctgac aatcctcttt ctcttttgtt ttacatgaag ggtctggcag  720
ccaaagcaat cactcaaagt tcaaacctta tcatttttg ctttgttcct cttggccttg  780
gttttgtaca tcagctttga aaataccatc ccagggttaa tgctggggtt aatttataac  840
taagagtgct ctagttttgc aatacaggac atgctataaa aatggaaaga tgttgctttc  900
tgagagactg cagaagttgg tcgtgaggca ctgggcaggt aagtatcaag gttacaagac  960
aggtttaagg agaccaatag aaactgggct tgtcgagaca gagaagactc ttgcgtttct  1020
gataggcacc tattggtctt actgacatcc actttgcctt tctctccaca ggtgtccagg  1080
cggccgccac catgtccagc aaaggctccg tggttctggc ctacagtggc ggcctggaca  1140
cctcgtgcat cctcgtgtgg ctgaaggaac aaggctatga cgtcattgcc tatctggcca  1200
acattggcca gaaggaagac ttcgaggaag ccaggaagaa ggcactgaag cttggggcca  1260
aaaaggtgtt cattgaggat gtcagcaggg agtttgtgga ggagttcatc tggccggcca  1320
tccagtccag cgcactgtat gaggaccgct acctcctggg cacctctctt gccaggccct  1380
gcatcgcccg caaacaagtg gaaatcgccc agcgggaggg ggccaagtat gtgtcccacg  1440
gcgccacagg aaaggggaac gatcaggtcc ggtttgagct cagctgctac tcactggccc  1500
cccagataaa ggtcattgct ccctggagga tgcctgaatt ctacaaccgg ttcaagggcc  1560
gcaatgacct gatggagtac gcaaagcaac acgggattcc catcccggtc actcccaaga  1620
acccgtggag catggatgag aacctcatgc acatcagcta cgaggctgga atcctggaga  1680
accccaagaa ccaagcgcct ccaggtctct acacgaagac ccaggaccca gccaaagccc  1740
ccaacacccc tgacattctc gagatcgagt tcaaaaaagg ggtccctgtg aaggtgacca  1800
acgtcaagga tggcaccacc caccagacct ccttggagct cttcatgtac ctgaacgaag  1860
tcgcgggcaa gcatggcgtg ggccgtattg acatcgtgga gaaccgcttc attggaatga  1920
agtcccgagg tatctacgag accccagcag gcaccatcct ttaccacgct catttagaca  1980
tcgaggcctt caccatggac cgggaagtgc gcaaaatcaa acaaggcctg ggcttgaaat  2040
ttgctgagct ggtgtatacc ggtttctggc acagccctga gtgtgaattt gtccgccact  2100
gcatcgccaa gtcccaggag cgagtggaag ggaaagtgca ggtgtccgtc ctcaagggcc  2160
aggtgtacat cctcggccgg gagtccccac tgtctctcta caatgaggag ctggtgagca  2220
tgaacgtgca gggtgattat gagccaactg atgccaccgg gttcatcaac atcaattccc  2280
tcaggctgaa ggaatatcat cgtctccaga gcaaggtcac tgccaaatga taagcatgcg  2340
gatctgcctc gactgtgcct tctagttgcc agccatctgt tgtttgcccc tcccccgtgc  2400
cttccttgac cctggaaggt gccactccca ctgtcctttc ctaataaaat gaggaaattg  2460
catcgcattg tctgagtagg tgtcattcta ttctgggggg tggggtgggg caggacagca  2520
agggggagga ttgggaagac aatagcaggc atgctgggga ctcgagttaa gggcgaattc  2580
ccgattagga tcttcctaga gcatggctac gtagataagt agcatggcgg gttaatcatt  2640
aactacaagg aacccctagt gatggagttg gccactccct ctctgcgcgc tcgctcgctc  2700
actgaggccg ggcgaccaaa ggtcgcccga cgcccgggct ttgcccgggc ggcctcagtg  2760
agcgagcgag cgcgcagcct taattaacct aattcactgg ccgtcgtttt acaacgtcgt  2820
gactgggaaa accctggcgt tacccaactt aatcgccttg cagcacatcc ccctttcgcc  2880
agctggcgta atagcgaaga ggcccgcacc gatcgccctt cccaacagtt gcgcagcctg  2940
aatggcgaat gggacgcgcc ctgtagcggc gcattaagcg cggcgggtgt ggtggttacg  3000
cgcagcgtga ccgctacact tgccagcgcc ctagcgcccg ctcctttcgc tttcttccct  3060
tcctttctcg ccacgttcgc cggctttccc cgtcaagctc taaatcgggg gctcccttta  3120
gggttccgat ttagtgcttt acggcacctc gaccccaaaa aacttgatta gggtgatggt  3180
tcacgtagtg ggccatcgcc ctgatagacg gtttttcgcc ctttgacgtt ggagtccacg  3240
ttctttaata gtggactctt gttccaaact ggaacaacac tcaaccctat ctcggtctat  3300
tcttttgatt tataagggat tttgccgatt tcggcctatt ggttaaaaaa tgagctgatt  3360
taacaaaaat ttaacgcgaa ttttaacaaa atattaacgc ttacaattta ggtggcactt  3420
ttcggggaaa tgtgcgcgga acccctattt gtttattttt ctaaatacat tcaaatatgt  3480
atccgctcat gagacaataa ccctgataaa tgcttcaata atattgaaaa aggaagagta  3540
tgagtattca acatttccgt gtcgccctta ttcccttttt tgcggcattt tgccttcctg  3600
tttttgctca cccagaaacg ctggtgaaag taaaagatgc tgaagatcag ttgggtgcac  3660
gagtgggtta catcgaactg gatctcaaca gcggtaagat ccttgagagt tttcgccccg  3720
aagaacgttt tccaatgatg agcactttta aagttctgct atgtggcgcg gtattatccc  3780
gtattgacgc cgggcaagag caactcggtc gccgcataca ctattctcag aatgacttgg  3840
ttgagtactc accagtcaca gaaaagcatc ttacggatgg catgacagta agagaattat  3900
gcagtgctgc cataaccatg agtgataaca ctgcggccaa cttacttctg acaacgatcg  3960
gaggaccgaa ggagctaacc gcttttttgc acaacatggg ggatcatgta actcgccttg  4020
atcgttggga accggagctg aatgaagcca taccaaacga cgagcgtgac accacgatgc  4080
ctgtagcaat ggcaacaacg ttgcgcaaac tattaactgg cgaactactt actctagctt  4140
cccggcaaca attaatagac tggatggagg cggataaagt tgcaggacca cttctgcgct  4200
cggcccttcc ggctggctgg tttattgctg ataaatctgg agccggtgag cgtgggtctc  4260
gcggtatcat tgcagcactg gggccagatg gtaagccctc ccgtatcgta gttatctaca  4320
cgacggggag tcaggcaact atggatgaac gaaatagaca gatcgctgag ataggtgcct  4380
cactgattaa gcattggtaa ctgtcagacc aagtttactc atatatactt tagattgatt  4440
taaaacttca tttttaattt aaaaggatct aggtgaagat cctttttgat aatctcatga  4500
ccaaaatccc ttaacgtgag ttttcgttcc actgagcgtc agaccccgta gaaaagatca  4560
aaggatcttc ttgagatcct ttttttctgc gcgtaatctg ctgcttgcaa acaaaaaaac  4620
caccgctacc agcggtggtt tgtttgccgg atcaagagct accaactctt tttccgaagg  4680
taactggctt cagcagagcg cagataccaa atactgttct tctagtgtag ccgtagttag  4740
gccaccactt caagaactct gtagcaccgc ctacatacct cgctctgcta atcctgttac  4800
cagtggctgc tgccagtggc gataagtcgt gtcttaccgg gttggactca agacgatagt  4860
taccggataa ggcgcagcgg tcgggctgaa cggggggttc gtgcacacag cccagcttgg  4920
agcgaacgac ctacaccgaa ctgagatacc tacagcgtga gctatgagaa agcgccacgc  4980
ttcccgaagg gagaaaggcg gacaggtatc cggtaagcgg cagggtcgga acaggagagc  5040
gcacgaggga gcttccaggg ggaaacgcct ggtatcttta tagtcctgtc gggtttcgcc  5100
acctctgact tgagcgtcga tttttgtgat gctcgtcagg ggggcggagc ctatggaaaa  5160
acgccagcaa cgcggccttt ttacggttcc tggccttttg ctggcctttt gctcacatgt  5220
```

-continued

```
tctttcctgc gttatcccct gattctgtgg ataaccgtat taccgccttt gagtgagctg  5280
ataccgctcg ccgcagccga acgaccgagc gcagcgagtc agtgagcgag gaagcggaag  5340
agcgcccaat acgcaaaccg cctctccccg cgcgttggcc gattcattaa tgcagctggc  5400
acgacaggtt tcccgactgg aaagcgggca gtgagcgcaa cgcaattaat gtgagttagc  5460
tcactcatta ggcaccccag gctttacact ttatgcttcc ggctcgtatg ttgtgtggaa  5520
ttgtgagcgg ataacaattt cacacaggaa acagctatga ccatgattac gccagattta  5580
attaagg                                                            5587

SEQ ID NO: 28          moltype = DNA  length = 6026
FEATURE                Location/Qualifiers
misc_feature           1..6026
                       note = constructed sequence
source                 1..6026
                       mol_type = other DNA
                       organism = synthetic construct
SEQUENCE: 28
ctgcgcgctc gctcgctcac tgaggccgcc cgggcaaagc ccgggcgtcg ggcgaccttt  60
ggtcgcccgg cctcagtgag cgagcgagcg cgcagagagg gagtggccaa ctccatcact  120
aggggttcct tgtagttaat gattaacccg ccatgctact tatctacgta gccatgctct  180
aggaagatcg gaattcgccc ttaaggctca gaggcacaca ggagtttctg ggctcaccct  240
gccccccttcc aacccctcag ttcccatcct ccagcagctg tttgtgtgct gcctctgaag  300
tccacactga acaaacttca gcctactcat gtccctaaaa tgggcaaaca ttgcaagcag  360
caaacagcaa acacacagcc ctccctgcct gctgaccttg gagctggggc agaggtcaga  420
gacctctctg ggcccatgcc acctccaaca tccactcgac cccttggaat ttcggtggag  480
aggagcagag gttgtcctgg cgtggtttag gtagtgtgag agggcgcgcc gatcttgcta  540
ccagtggaac agccactaag gattctgcag tgagagcaga gggccagcta agtggtactc  600
tcccagagac tgtctgactc acgccacccc ctccaccttg gacacaggac gctgtggttt  660
ctgagccagg tacaatgact cctttcggta agtgcagtgg aagctgtaca ctgcccaggc  720
aaagcgtccg ggcagcgtag gcgggcgact cagatcccag ccagtggact tagcccctgt  780
ttgctcctcc gataactggg gtgaccttgg ttaatattca ccagcagcct cccccgttgc  840
ccctctggat ccactgctta aatacggacg aggacagggc cctgtctcct cagcttcagg  900
caccaccact gacctgggac agtagatcta gcttacttgt ggtaccgagc tcggatcctg  960
agaacttcag ggtgagtcta tgggaccctt gatgttttct ttccccttct tttctatggt  1020
taagttcatg tcataggaag gggagaagta acagggtaca catattgacc aaatcagggt  1080
aattttgcat ttgtaatttt aaaaaatgct ttcttctttt aatatacttt tttgtttatc  1140
ttatttctaa tactttccct aatctctttc tttcagggca ataatgatac aatgtatcat  1200
gcctctttgc accattctaa agaataacag tgataatttc tgggttaagg caatagcaat  1260
atttctgcat ataaatattt ctgcatataa attgtaactg atgtaagagg tttcatattg  1320
ctaatagcag ctacaatcca gctaccattc tgcttttatt ttatggttgg gataaggctg  1380
gattattctg agtccaagct aggccctttt gctaatcatg ttcatacctc ttatcttcct  1440
cccacagctc ctgggcaacg tgctggtctg tgtgctggcc catcactttg gcaaagaatt  1500
gatctcgagt aactgaaggc ggccgccacc atgtccagca aaggctccgt ggttctggcc  1560
tacagtggcg gcctggacac ctcgtgcatc ctcgtgtggc tgaaggaaca aggctatgac  1620
gtcattgcct atctggccaa cattggccag aaggaagact tcgaggaagc caggaagaag  1680
gcactgaagc ttggggccaa aaaggtgttc attgaggatg tcagcaggga gtttgtggag  1740
gagttcatct ggccggccat ccagtccagc gcactgtatg aggaccgcta cctcctgggc  1800
acctctcttg ccaggccctg catcgcccgc aaacaagtgg aaatcgccca gcgggagggg  1860
gccaagtatg tgtcccacgg cgccacagga aaggggaacg atcaggtccg gtttgagctc  1920
agctgctact cactggcccc ccagataaag gtcattgctc cctggaggat gcctgaattc  1980
tacaaccggt tcaagggccg caatgacctg atggagtacg caaagcaaca cgggattccc  2040
atcccggtca ctcccaagaa cccgtggagc atggatgaga acctcatgca catcagctac  2100
gaggctggaa tcctggagaa ccccaagaac caagcgcctc caggtctcta cacgaagacc  2160
caggacccag ccaaagcccc caacacccct gacattctcg agatcgagtt caaaaaaggg  2220
gtccctgtga aggtgaccaa cgtcaaggat ggcaccaccc accagacctc cttggagctc  2280
ttcatgtacc tgaacgaagt cgcgggcaag catggcgtgg gccgtattga catcgtggag  2340
aaccgcttca ttggaatgaa gtcccgaggt atctacgaga ccccagcagg caccatcctt  2400
taccacgctc atttagacat cgaggccttc accatggacc gggaagtgcg caaaatcaaa  2460
caaggcctgg gcttgaaatt tgctgagctg gtgtataccg gtttctggca cagccctgag  2520
tgtgaatttg tccgccactg catcgccaag tcccaggagc gagtggaagg gaaagtgcag  2580
gtgtccgtcc tcaagggcca ggtgtacatc ctcggccggg agtccccact gtctctctac  2640
aatgaggagc tggtgagcat gaacgtgcag ggtgattatg agccaactga tgccaccggg  2700
ttcatcaaca tcaattccct caggctgaag gaatatcatc gtctccagag caaggtcact  2760
gccaaatgat aagcatgcgg atctgcctcg actgtgcctt ctagttgcca gccatctgtt  2820
gtttgcccct cccccgtgcc ttccttgacc ctggaaggtg ccactcccac tgtcctttcc  2880
taataaaatg aggaaattgc atcgcattgt ctgagtaggt gtcattctat tctgggggtt  2940
ggggtggggc aggacagcaa gggggaggat tgggaagaca atagcaggca tgctggggac  3000
tcgagttaag ggcgaattcc cgataaggat cttcctagag catggctacg tagataagta  3060
gcatggcggg ttaatcatta actacaagga acccctagtg atggagttgg ccactccctc  3120
tctgcgcgct cgctcgctca ctgaggccgg gcgaccaaag gtcgcccgac gcccgggctt  3180
tgcccgggcg gcctcagtga gcgagcgagc gcgcagcctt aattaaccta attcactggc  3240
cgtcgtttta caacgtcgtg actgggaaaa ccctggcgtt acccaactta atcgccttgc  3300
agcacatccc cctttcgcca gctggcgtaa tagcgaagag gcccgcaccg atcgcccttc  3360
ccaacagttg cgcagcctga atggcgaatg ggacgcgccc tgtagcggcg cattaagcgc  3420
ggcgggtgtg gtggttacgc gcagcgtgac cgctacactt gccagcgccc tagcgcccgc  3480
tcctttcgct ttcttccctt cctttctcgc cacgttcgcc ggctttcccc gtcaagctct  3540
aaatcggggg ctccctttag ggttccgatt tagtgcttta cggcacctcg accccaaaaa  3600
acttgattag ggtgatggtt cacgtagtgg gccatcgccc tgatagacgg tttttcgccc  3660
tttgacgttg gagtccacgt tctttaatag tggactcttg ttccaaactg gaacaacact  3720
caaccctatc tcggtctatt cttttgattt ataagggatt tgccgatttc cggcctattg  3780
```

-continued

```
gttaaaaaat gagctgattt aacaaaaatt taacgcgaat tttaacaaaa tattaacgct  3840
tacaatttag gtggcacttt tcggggaaat gtgcgcggaa cccctatttg tttatttttc  3900
taaatacatt caaatatgta tccgctcatg agacaataac cctgataaat gcttcaataa  3960
tattgaaaaa ggaagagtat gagtattcaa catttccgtg tcgcccttat tccctttttt  4020
gcggcatttt gccttcctgt ttttgctcac ccagaaacgc tggtgaaagt aaaagatgct  4080
gaagatcagt tgggtgcacg agtgggttac atcgaactgg atctcaacag cggtaagatc  4140
cttgagagtt ttcgccccga agaacgtttt ccaatgatga gcacttttaa agttctgcta  4200
tgtggcgcgg tattatcccg tattgacgcc gggcaagagc aactcggtcg ccgcatacac  4260
tattctcaga atgacttggt tgagtactca ccagtcacag aaaagcatct tacggatggc  4320
atgacagtaa gagaattatg cagtgctgcc ataaccatga gtgataacac tgcggccaac  4380
ttacttctga caacgatcgg aggaccgaag gagctaaccg cttttttgca caacatgggg  4440
gatcatgtaa ctcgccttga tcgttgggaa ccggagctga atgaagccat accaaacgac  4500
gagcgtgaca ccacgatgcc tgtagcaatg gcaacaacgt tgcgcaaact attaactggc  4560
gaactactta ctctagcttc ccggcaacaa ttaatagact ggatggaggc ggataaagtt  4620
gcaggaccac ttctgcgctc ggcccttccg gctggctggt ttattgctga taaatctgga  4680
gccggtgagc gtgggtctcg cggtatcatt gcagcactgg ggccagatgg taagccctcc  4740
cgtatcgtag ttatctacac gacggggagt caggcaacta tggatgaacg aaatagacag  4800
atcgctgaga taggtgcctc actgattaag cattggtaac tgtcagacca agtttactca  4860
tatatacttt agattgattt aaaacttcat ttttaattta aaaggatcta ggtgaagatc  4920
ctttttgata atctcatgac caaaatccct taacgtgagt tttcgttcca ctgagcgtca  4980
gaccccgtag aaaagatcaa aggatcttct tgagatcctt tttttctgcg cgtaatctgc  5040
tgcttgcaaa caaaaaaacc accgctacca gcggtggttt gtttgccgga tcaagagcta  5100
ccaactcttt ttccgaaggt aactggcttc agcagagcgc agataccaaa tactgttctt  5160
ctagtgtagc cgtagttagg ccaccacttc aagaactctg tagcaccgcc tacatacctc  5220
gctctgctaa tcctgttacc agtggctgct gccagtggcg ataagtcgtg tcttaccggg  5280
ttggactcaa gacgatagtt accggataag gcgcagcggt cgggctgaac ggggggttcg  5340
tgcacacagc ccagcttgga gcgaacgacc tacaccgaac tgagatacct acagcgtgag  5400
ctatgagaaa gcgccacgct tcccgaaggg agaaaggcgg acaggtatcc ggtaagcggc  5460
agggtcggaa caggagagcg cacgagggag cttccagggg gaaacgcctg gtatctttat  5520
agtcctgtcg ggtttcgcca cctctgactt gagcgtcgat ttttgtgatg ctcgtcaggg  5580
gggcggagcc tatggaaaaa cgccagcaac gcggcctttt tacggttcct ggccttttgc  5640
tggccttttg ctcacatgtt ctttcctgcg ttatcccctg attctgtgga taaccgtatt  5700
accgcctttg agtgagctga taccgctcgc cgcagccgaa cgaccgagcg cagcgagtca  5760
gtgagcgagg aagcggaaga gcgcccaata cgcaaaccgc ctctccccgc gcgttggccg  5820
attcattaat gcagctggca cgacaggttt cccgactgga aagcgggcag tgagcgcaac  5880
gcaattaatg tgagttagct cactcattag gcaccccagg ctttacactt tatgcttccg  5940
gctcgtatgt tgtgtggaat tgtgagcgga taacaatttc acacaggaaa cagctatgac  6000
catgattacg ccagatttaa ttaagg                                        6026

SEQ ID NO: 29          moltype = DNA  length = 5876
FEATURE                Location/Qualifiers
misc_feature           1..5876
                       note = constructed sequence
source                 1..5876
                       mol_type = other DNA
                       organism = synthetic construct
SEQUENCE: 29
ctgcgcgctc gctcgctcac tgaggccgcc cgggcaaagc ccgggcgtcg ggcgaccttt  60
ggtcgcccgg cctcagtgag cgagcgagcg cgcagagagg gagtggccaa ctccatcact  120
aggggttcct tgtagttaat gattaacccg ccatgctact tatctacgta gccatgctct  180
aggaagatcg gaattcgccc ttaagctagc cgctgacaag gctcagaggc acacaggagt  240
ttctgggctc accctgcccc cttccaaccc ctcagttccc atcctccagc agctgtttgt  300
gtgctgcctc tgaagtccac actgaacaaa cttcagccta ctcatgtccc taaaatgggc  360
aaacattgca agcagcaaac agcaaacaca cagccctccc tgcctgctga ccttggagct  420
ggggcagagg tcagagacct ctctgggccc atgccacctc caacatccac tcgacccctt  480
ggaatttcgg tggagaggag cagaggttgt cctggcgtgg tttaggtagt gtgagaggga  540
gatccggcgc gcctggacac aggacgctgt ggtttctgag ccaggggggcg actcagatcc  600
cagccagtgg acttagcccc tgtttgctcc tccgataact ggggtgacct tggttaatat  660
tcaccagcag cctcccccgt tgcccctctg gatccactgc ttaaatacgg acgaggacag  720
ggccctgtct cctcagcttc aggcaccacc actgacctgg gacagtgaat agcgagatct  780
agcttacttg tggtaccagc tcggatcctg agaacttcag ggtgagtcta tgggaccctt  840
gatgttttct ttccccttct ttctatggt taagttcatg tcataggaag gggagaagta  900
acagggtaca catattgacc aaatcagggt aattttgcat ttgtaatttt aaaaaatgct  960
ttcttctttt aatatacttt tttgtttatc ttatttctaa tactttccct aatctctttc  1020
tttcagggca ataatgatac aatgtatcat gcctctttgc accattctaa agaataacag  1080
tgataatttc tgggttaagg caatagcaat atttctgcat ataaatattt ctgcatataa  1140
attgtaactg atgtaagagg tttcatattg ctaatagcag ctacaatcca gctaccattc  1200
tgcttttatt ttatggttgg gataaggctg gattattctg agtccaagct aggccctttt  1260
gctaatcatg ttcatacctc ttatcttcct cccacagctc ctgggcaacg tgctggtctg  1320
tgtgctggcc catcactttg gcaaagaatt gatctcgagt aactgaaggc ggccgccacc  1380
atgagcagca agggctctgt ggtgctggcc tactctggcg gcctggacac cagctgtatc  1440
ctcgtgtggc tgaaagaaca gggctacgac gtgatcgcct acctggccaa catcggccag  1500
aaagaggact tcgaggaagc ccggaagaag gccctgaagc tgggcgccaa gaaggtgttc  1560
atcgaggacg tgtcccgcga gttcgtggaa gagttcatct ggcccgccat ccagagcagc  1620
gccctgtacg aggacagata cctgctgggc accagcctgg ccagaccctg tatcgcccgg  1680
aaacaggtgg aaatcgccca gcgcgagggc gccaaatacg tgtctcacgg cgccaccggc  1740
aagggcaacg accaggtgcg ctttgagctg agctgctact ccctggcccc ccagatcaaa  1800
gtgatcgccc cttggcggat gcccgagttc tacaaccggt tcaagggccg gaacgacctg  1860
atggaatacg ccaagcagca cggcatcccc atccccgtga cccccaagaa cccttggagc  1920
```

```
atggacgaga acctgatgca catcagctac gaggccggca tcctggaaaa ccccaagaat  1980
caggcccctc ccggcctgta cacaaagacc caggaccctg ccaaggcccc caacacccc   2040
gacattctgg aaatcgagtt caagaaaggc gtgcccgtga aagtgaccaa cgtgaaggac  2100
ggcaccaccc accagacctc cctggaactg ttcatgtacc tgaacgaggt ggccggcaag  2160
cacggcgtgg gcagaatcga catcgtggaa aacagattca tcggcatgaa gtcccggggc  2220
atctacgaga caccagccgg caccatcctg taccacgccc acctggatat cgaggccttc  2280
accatggacc gggaagtgcg gaagatcaag cagggcctgg gcctgaagtt cgccgagctg  2340
gtgtacacag gcttttggca cagccccgag tgcgagtttg tgcggcactg cattgccaag  2400
agccaggaac gggtggaagg caaggtgcag gtgtccgtgc tgaagggcca ggtgtacatt  2460
ctgggcagag agagccccct gagcctgtac aacgaggaac tggtgtctat gaacgtgcag  2520
ggcgactacg agcccaccga cgccaccggc ttcatcaaca tcaacagcct gagactgaaa  2580
gagtaccacc ggctgcagtc caaagtgacc gccaagtgat aagcatgcgg atctgcctcg  2640
actgtgcctt ctagttgcca gccatctgtt gtttgcccct cccccgtgcc ttccttgacc  2700
ctggaaggtg ccactcccac tgtcctttcc taataaaatg aggaaattgc atcgcattgt  2760
ctgagtaggt gtcattctat tctggggggt ggggtggggc aggacagcaa gggggaggat  2820
tgggaagaca atagcaggca tgctggggac tcgagttaag ggcgaattcc cgataaggat  2880
cttcctagag catggctacg tagataagta gcatggcggg ttaatcatta actacaagga  2940
acccctagtg atggagttgg ccactccctc tctgcgcgct cgctcgctca ctgaggccgg  3000
gcgaccaaag gtcgcccgac gcccgggctt tgcccgggcg gcctcagtga gcgagcgagc  3060
gcgcagcctt aattaaccta attcactggc cgtcgtttta caacgtcgtg actgggaaaa  3120
ccctggcgtt acccaactta atcgccttgc agcacatccc cctttcgcca gctggcgtaa  3180
tagcgaagag gcccgcaccg atcgcccttc ccaacagttg cgcagcctga atggcgaatg  3240
ggacgcgccc tgtagcggcg cattaagcgc ggcgggtgtg gtggttacgc gcagcgtgac  3300
cgctacactt gccagcgccc tagcgcccgc tcctttcgct ttcttccctt cctttctcgc  3360
cacgttcgcc ggctttcccc gtcaagctct aaatcggggg ctccctttag ggttccgatt  3420
tagtgcttta cggcacctcg accccaaaaa acttgattag ggtgatggtt cacgtagtgg  3480
gccatcgccc tgatagacgg tttttcgccc tttgacgttg gagtccacgt tctttaatag  3540
tggactcttg ttccaaactg gaacaacact caaccctatc tcggtctatt cttttgattt  3600
ataagggatt ttgccgattt cggcctattg gttaaaaaat gagctgattt aacaaaaatt  3660
taacgcgaat tttaacaaaa tattaacgct tacaatttag gtggcacttt tcggggaaat  3720
gtgcgcggaa cccctatttg tttatttttc taaatacatt caaatatgta tccgctcatg  3780
agacaataac cctgataaat gcttcaataa tattgaaaaa ggaagagtat gagtattcaa  3840
catttccgtg tcgcccttat tccctttttt gcggcatttt gccttcctgt ttttgctcac  3900
ccagaaacgc tggtgaaagt aaaagatgct gaagatcagt tgggtgcacg agtgggttac  3960
atcgaactgg atctcaacag cggtaagatc cttgagagtt ttcgccccga agaacgtttt  4020
ccaatgatga gcacttttaa agttctgcta tgtggcgcgg tattatcccg tattgacgcc  4080
gggcaagagc aactcggtcg ccgcatacac tattctcaga atgacttggt tgagtactca  4140
ccagtcacag aaaagcatct tacggatggc atgacagtaa gagaattatg cagtgctgcc  4200
ataaccatga gtgataacac tgcggccaac ttacttctga caacgatcgg aggaccgaag  4260
gagctaaccg cttttttgca caacatgggg gatcatgtaa ctcgccttga tcgttgggaa  4320
ccggagctga atgaagccat accaaacgac gagcgtgaca ccacgatgcc tgtagcaatg  4380
gcaacaacgt tgcgcaaact attaactggc gaactactta ctctagcttc ccggcaacaa  4440
ttaatagact ggatggaggc ggataaagtt gcaggaccac ttctgcgctc ggcccttccg  4500
gctggctggt ttattgctga taaatctgga gccggtgagc gtgggtctcg cggtatcatt  4560
gcagcactgg ggccagatgg taagccctcc cgtatcgtag ttatctacac gacggggagt  4620
caggcaacta tggatgaacg aaatagacag atcgctgaga taggtgcctc actgattaag  4680
cattggtaac tgtcagacca agtttactca tatatacttt agattgattt aaaacttcat  4740
ttttaattta aaaggatcta ggtgaagatc ctttttgata atctcatgac caaaatccct  4800
taacgtgagt tttcgttcca ctgagcgtca gaccccgtag aaaagatcaa aggatcttct  4860
tgagatcctt tttttctgcg cgtaatctgc tgcttgcaaa caaaaaaacc accgctacca  4920
gcggtggttt gtttgccgga tcaagagcta ccaactcttt ttccgaaggt aactggcttc  4980
agcagagcgc agataccaaa tactgttctt ctagtgtagc cgtagttagg ccaccacttc  5040
aagaactctg tagcaccgcc tacatacctc gctctgctaa tcctgttacc agtggctgct  5100
gccagtggcg ataagtcgtg tcttaccggg ttggactcaa gacgatagtt accggataag  5160
gcgcagcggt cgggctgaac ggggggttcg tgcacacagc ccagcttgga gcgaacgacc  5220
tacaccgaac tgagatacct acagcgtgag ctatgagaaa gcgccacgct tcccgaaggg  5280
agaaaggcgg acaggtatcc ggtaagcggc agggtcggaa caggagagcg cacgagggag  5340
cttccagggg gaaacgcctg gtatctttat agtcctgtcg ggtttcgcca cctctgactt  5400
gagcgtcgat ttttgtgatg ctcgtcaggg gggcggagcc tatggaaaaa cgccagcaac  5460
gcggcctttt tacggttcct ggccttttgc tggccttttg ctcacatgtt ctttcctgcg  5520
ttatcccctg attctgtgga taaccgtatt accgcctttg agtgagctga taccgctcgc  5580
cgcagccgaa cgaccgagcg cagcgagtca gtgagcgagg aagcggaaga gcgcccaata  5640
cgcaaaccgc ctctccccgc gcgttggccg attcattaat gcagctggca cgacaggttt  5700
cccgactgga aagcgggcag tgagcgcaac gcaattaatg tgagttagct cactcattag  5760
gcaccccagg ctttacactt tatgcttccg gctcgtatgt tgtgtggaat tgtgagcgga  5820
taacaatttc acacaggaaa cagctatgac catgattacg ccagatttaa ttaagg      5876
```

```
SEQ ID NO: 30          moltype = DNA  length = 4893
FEATURE                Location/Qualifiers
misc_feature           1..4893
                       note = constructed sequence
source                 1..4893
                       mol_type = other DNA
                       organism = synthetic construct
SEQUENCE: 30
ctgcgcgctc gctcgctcac tgaggccgcc cgggcaaagc ccgggcgtcg ggcgaccttt  60
ggtcgcccgg cctcagtgag cgagcgagcg cgcagagagg gagtggccaa ctccatcact  120
aggggttcct tgtagttaat gattaacccg ccatgctact tatctactta agtgtttgct  180
gcttgcaatg tttgcccatt ttaggggaat tctggacaca ggacgctgtg gtttctgagc  240
```

-continued

```
caggggggcga ctcagatccc agccagtgga cttagcccct gtttgctcct ccgataactg  300
gggtgacctt ggttaatatt caccagcagc ctccccccgtt gcccctctgg atccactgct  360
taaatacgga cgaggacagg gccctgtctc ctcagcttca ggcaccacca ctgacctggg  420
acagtgaata gcggccgcca ccatgagcag caagggctct gtggtgctgg cctactctgg  480
cggcctggac accagctgta tcctcgtgtg gctgaaagaa cagggctacg acgtgatcgc  540
ctacctggcc aacatcggcc agaaagagga cttcgaggaa gcccggaaga aggccctgaa  600
gctgggcgcc aagaaggtgt tcatcgagga cgtgtcccgc gagttcgtgg aagagttcat  660
ctggcccgcc atccagagca gcgccctgta cgaggacaga tacctgctgg gcaccagcct  720
ggccagaccc tgtatcgccc ggaaacaggt ggaaatcgcc cagcgcgagg gcgccaaata  780
cgtgtctcac ggcgccaccg gcaagggcaa cgaccaggtg cgctttgagc tgagctgcta  840
ctccctggcc ccccagatca aagtgatcgc cccttggcgg atgcccgagt tctacaaccg  900
gttcaagggc cggaacgacc tgatggaata cgccaagcag cacggcatcc ccatccccgt  960
gacccccaag aacccttgga gcatggacga gaacctgatg cacatcagct acgaggccgg  1020
catcctggaa aaccccaaga atcaggcccc tcccggcctg tacacaaaga cccaggaccc  1080
tgccaaggcc cccaacaccc ccgacattct ggaaatcgag ttcaagaaag gcgtgcccgt  1140
gaaagtgacc aacgtgaagg acggcaccac ccaccagacc tccctggaac tgttcatgta  1200
cctgaacgag gtggccggca agcacggcgt gggcagaatc gacatcgtgg aaaacagatt  1260
catcggcatg aagtcccggg gcatctacga gacaccagcc ggcaccatcc tgtaccacgc  1320
ccacctggat atcgaggcct tcaccatgga ccgggaagtg cggaagatca agcagggcct  1380
gggcctgaag ttcgccgagc tggtgtacac aggcttttgg cacagccccg agtgcgagtt  1440
tgtgcggcac tgcattgcca agagccagga acgggtggaa ggcaaggtgc aggtgtccgt  1500
gctgaagggc caggtgtaca ttctgggcag agagagcccc ctgagcctgt acaacgagga  1560
actggtgtct atgaacgtgc agggcgacta cgagcccacc gacgccaccg gcttcatcaa  1620
catcaacagc ctgagactga aagagtacca ccggctgcag tccaaagtga ccgccaagtg  1680
ataagcatgc ggatctgcct cgactgtgcc ttctagttgc cagccatctg ttgtttgccc  1740
ctcccccgtg ccttccttga ccctggaagg tgccactccc actgtccttt cctaataaaa  1800
tgaggaaatt gcatcgcatt gtctgagtag gtgtcattct attctggggg gtggggtggg  1860
gcaggacagc aagggggagg attgggaaga caatagcagg catgctgggg actcgagtag  1920
ataagtagca tggcgggtta atcattaact acaaggaacc cctagtgatg gagttggcca  1980
ctccctctct gcgcgctcgc tcgctcactg aggccgggcg accaaaggtc gcccgacgcc  2040
cgggctttgc ccgggcggcc tcagtgagcg agcgagcgcg cagccttaat taacctaatt  2100
cactggccgt cgttttacaa cgtcgtgact gggaaaaccc tggcgttacc caacttaatc  2160
gccttgcagc acatccccct ttcgccagct ggcgtaatag cgaagaggcc cgcaccgatc  2220
gcccttccca acagttgcgc agcctgaatg gcgaatggga cgcgccctgt agcggcgcat  2280
taagcgcggc gggtgtggtg gttacgcgca gcgtgaccgc tacacttgcc agcgccctag  2340
cgcccgctcc tttcgctttc ttcccttcct ttctcgccac gttcgccggc tttccccgtc  2400
aagctctaaa tcgggggctc cctttagggt tccgatttag tgctttacgg cacctcgacc  2460
ccaaaaaact tgattagggt gatggttcac gtagtgggcc atcgccctga tagacggttt  2520
ttcgcccttt gacgttggag tccacgttct ttaatagtgg actcttgttc caaactggaa  2580
caacactcaa ccctatctcg gtctattctt ttgatttata agggattttg ccgatttcgg  2640
cctattggtt aaaaaatgag ctgatttaac aaaaatttaa cgcgaatttt aacaaaatat  2700
taacgcttac aatttaggtg gcacttttcg gggaaatgtg cgcggaaccc ctatttgttt  2760
atttttctaa atacattcaa atatgtatcc gctcatgaga caataaccct gataaatgct  2820
tcaataatat tgaaaaagga agagtatgag tattcaacat ttccgtgtcg cccttattcc  2880
cttttttgcg gcattttgcc ttcctgtttt tgctcaccca gaaacgctgg tgaaagtaaa  2940
agatgctgaa gatcagttgg gtgcacgagt gggttacatc gaactggatc tcaacagcgg  3000
taagatcctt gagagttttc gccccgaaga acgttttcca atgatgagca cttttaaagt  3060
tctgctatgt ggcgcggtat tatcccgtat tgacgccggg caagagcaac tcggtcgccg  3120
catacactat tctcagaatg acttggttga gtactcacca gtcacagaaa agcatcttac  3180
ggatggcatg acagtaagag aattatgcag tgctgccata accatgagtg ataacactgc  3240
ggccaactta cttctgacaa cgatcggagg accgaaggag ctaaccgctt ttttgcacaa  3300
catgggggat catgtaactc gccttgatcg ttgggaaccg gagctgaatg aagccatacc  3360
aaacgacgag cgtgacacca cgatgcctgt agcaatggca acaacgttgc gcaaactatt  3420
aactggcgaa ctacttactc tagcttcccg gcaacaatta atagactgga tggaggcgga  3480
taaagttgca ggaccacttc tgcgctcggc ccttccggct ggctggttta ttgctgataa  3540
atctggagcc ggtgagcgtg ggtctcgcgg tatcattgca gcactggggc cagatggtaa  3600
gccctcccgt atcgtagtta tctacacgac ggggagtcag gcaactatgg atgaacgaaa  3660
tagacagatc gctgagatag gtgcctcact gattaagcat tggtaactgt cagaccaagt  3720
ttactcatat atactttaga ttgatttaaa acttcatttt taatttaaaa ggatctaggt  3780
gaagatcctt tttgataatc tcatgaccaa aatcccttaa cgtgagtttt cgttccactg  3840
agcgtcagac cccgtagaaa agatcaaagg atcttcttga gatccttttt ttctgcgcgt  3900
aatctgctgc ttgcaaacaa aaaaaccacc gctaccagcg gtggtttgtt tgccggatca  3960
agagctacca actctttttc cgaaggtaac tggcttcagc agagcgcaga taccaaatac  4020
tgttcttcta gtgtagccgt agttaggcca ccacttcaag aactctgtag caccgcctac  4080
atacctcgct ctgctaatcc tgttaccagt ggctgctgcc agtggcgata agtcgtgtct  4140
taccgggttg gactcaagac gatagttacc ggataaggcg cagcggtcgg gctgaacggg  4200
gggttcgtgc acacagccca gcttggagcg aacgacctac accgaactga gatacctaca  4260
gcgtgagcta tgagaaagcg ccacgcttcc cgaagggaga aaggcggaca ggtatccggt  4320
aagcggcagg gtcggaacag gagagcgcac gagggagctt ccagggggaa acgcctggta  4380
tctttatagt cctgtcgggt ttcgccacct ctgacttgag cgtcgatttt tgtgatgctc  4440
gtcagggggg cggagcctat ggaaaaacgc cagcaacgcg gcctttttac ggttcctggc  4500
cttttgctgg ccttttgctc acatgttctt tcctgcgtta tcccctgatt ctgtggataa  4560
ccgtattacc gcctttgagt gagctgatac cgctcgccgc agccgaacga ccgagcgcag  4620
cgagtcagtg agcgaggaag cggaagagcg cccaatacgc aaaccgcctc tccccgcgcg  4680
ttggccgatt cattaatgca gctggcacga caggtttccc gactggaaag cgggcagtga  4740
gcgcaacgca attaatgtga gttagctcac tcattaggca ccccaggctt tacactttat  4800
gcttccggct cgtatgttgt gtggaattgt gagcggataa caatttcaca caggaaacag  4860
ctatgaccat gattacgcca gatttaatta agg                                4893
```

-continued

```
SEQ ID NO: 31          moltype = DNA  length = 4931
FEATURE                Location/Qualifiers
misc_feature           1..4931
                       note = constructed sequence
source                 1..4931
                       mol_type = other DNA
                       organism = synthetic construct
SEQUENCE: 31
ctgcgcgctc gctcgctcac tgaggccgcc cgggcaaagc ccgggcgtcg ggcgaccttt  60
ggtcgcccgg cctcagtgag cgagcgagcg cgcagagagg gagtggccaa ctccatcact  120
aggggttcct tgtagttaat gattaacccg ccatgctact tatctactta agctacctcg  180
tgatcgcccg gcccctgttc aaacatgtcc taatactctg tctctgcaag ggtcatcagt  240
agttttccat cttactcaac atcctcccag tggaattcat ttcatagaac gaatgttccg  300
atgctctaat ctctctagac aaggttcata tttgtatggg ttacttattc tctctttgtt  360
gactaagtca ataatcagaa tcagcaggtt tgcagtcaga ttggcaggga taagcagcct  420
agctcaggag aagtgagtat aaaagcccca ggctgggagc agccatcagc ggccgccacc  480
atgagcagca agggctctgt ggtgctggcc tactctggcg gcctggacac cagctgtatc  540
ctcgtgtggc tgaaagaaca gggctacgac gtgatcgcct acctggccaa catcggccag  600
aaagaggact tcgaggaagc ccggaagaag gccctgaagc tgggcgccaa gaaggtgttc  660
atcgaggacg tgtcccgcga gttcgtggaa gagttcatct ggcccgccat ccagagcagc  720
gccctgtacg aggacagata cctgctgggc accagcctgg ccagaccctg tatcgcccgg  780
aaacaggtgg aaatcgccca gcgcgagggc gccaaatacg tgtctcacgg cgccaccggc  840
aagggcaacg accaggtgcg ctttgagctg agctgctact ccctggcccc ccagatcaaa  900
gtgatcgccc cttggcggat gcccgagttc tacaaccggt tcaagggccg gaacgacctg  960
atggaatacg ccaagcagca cggcatcccc atccccgtga cccccaagaa cccttggagc  1020
atggacgaga acctgatgca catcagctac gaggccggca tcctggaaaa ccccaagaat  1080
caggcccctc ccggcctgta cacaaagacc caggaccctg ccaaggcccc caacaccccc  1140
gacattctgg aaatcgagtt caagaaaggc gtgcccgtga aagtgaccaa cgtgaaggac  1200
ggcaccaccc accagacctc cctggaactg ttcatgtacc tgaacgaggt ggccggcaag  1260
cacggcgtgg gcagaatcga catcgtggaa aacagattca tcggcatgaa gtcccggggc  1320
atctacgaga caccagccgg caccatcctg taccacgccc acctggatat cgaggccttc  1380
accatggacc gggaagtgcg gaagatcaag cagggcctgg gcctgaagtt cgccgagctg  1440
gtgtacacag gcttttggca cagccccgag tgcgagtttg tgcggcactg cattgccaag  1500
agccaggaac gggtggaagg caaggtgcag gtgtccgtgc tgaagggcca ggtgtacatt  1560
ctgggcagag agagccccct gagcctgtac aacgaggaac tggtgtctat gaacgtgcag  1620
ggcgactacg agcccaccga cgccaccggc ttcatcaaca tcaacagcct gagactgaaa  1680
gagtaccacc ggctgcagtc caaagtgacc gccaagtgat aagcatgcgg atctgcctcg  1740
actgtgcctt ctagttgcca gccatctgtt gtttgcccct cccccgtgcc ttccttgacc  1800
ctggaaggtg ccactcccac tgtcctttcc taataaaatg aggaaattgc atcgcattgt  1860
ctgagtaggt gtcattctat tctggggggt ggggtggggc aggacagcaa gggggaggat  1920
tgggaagaca atagcaggca tgctggggac tcgagtagat aagtagcatg gcgggttaat  1980
cattaactac aaggaacccc tagtgatgga gttggccact ccctctctgc gcgctcgctc  2040
gctcactgag gccgggcgac caaaggtcgc ccgacgcccg ggctttgccc gggcggcctc  2100
agtgagcgag cgagcgcgca gccttaatta acctaattca ctggccgtcg ttttacaacg  2160
tcgtgactgg gaaaaccctg gcgttaccca acttaatcgc cttgcagcac atcccccttt  2220
cgccagctgg cgtaatagcg aagaggcccg caccgatcgc ccttcccaac agttgcgcag  2280
cctgaatggc gaatggacgc gccctgtagc ggcgcattaa gcgcggcggg tgtggtggtt  2340
acgcgcagc gtgaccgcta cacttgccag cgccctagcg cccgctcctt tcgctttctt  2400
cccttccttt ctcgccacgt tcgccggctt tccccgtcaa gctctaaatc gggggctccc  2460
tttagggttc cgatttagtg ctttacggca cctcgacccc aaaaaacttg attagggtga  2520
tggttcacgt agtgggccat cgccctgata gacggttttt cgccctttga cgttggagtc  2580
cacgttcttt aatagtggac tcttgttcca aactggaaca acactcaacc ctatctcggt  2640
ctattctttt gatttataag ggattttgcc gatttcggcc tattggttaa aaaatgagct  2700
gatttaacaa aaatttaacg cgaattttaa caaaatatta acgcttacaa tttaggtggc  2760
acttttcggg gaaatgtgcg cggaacccct atttgtttat ttttctaaat acattcaaat  2820
atgtatccgc tcatgagaca ataaccctga taaatgcttc aataatattg aaaaaggaag  2880
agtatgagta ttcaacattt ccgtgtcgcc cttattccct tttttgcggc attttgcctt  2940
cctgtttttg ctcacccaga aacgctggtg aaagtaaaag atgctgaaga tcagttgggt  3000
gcacgagtgg gttacatcga actggatctc aacagcggta agatccttga gagttttcgc  3060
cccgaagaac gttttccaat gatgagcact tttaaagttc tgctatgtgg cgcggtatta  3120
tcccgtattg acgccgggca agagcaactc ggtcgccgca tacactattc tcagaatgac  3180
ttggttgagt actcaccagt cacagaaaag catcttacgg atggcatgac agtaagagaa  3240
ttatgcagtg ctgccataac catgagtgat aacactgcgg ccaacttact tctgacaacg  3300
atcggaggac cgaaggagct aaccgctttt ttgcacaaca tgggggatca tgtaactcgc  3360
cttgatcgtt gggaaccgga gctgaatgaa gccataccaa acgacgagcg tgacaccacg  3420
atgcctgtag caatggcaac aacgttgcgc aaactattaa ctggcgaact acttactcta  3480
gcttcccggc aacaattaat agactggatg gaggcggata aagttgcagg accacttctg  3540
cgctcggccc ttccggctgg ctggtttatt gctgataaat ctggagccgg tgagcgtggg  3600
tctcgcggta tcattgcagc actggggcca gatggtaagc cctcccgtat cgtagttatc  3660
tacacgacgg ggagtcaggc aactatggat gaacgaaata gacagatcgc tgagataggt  3720
gcctcactga ttaagcattg gtaactgtca gaccaagttt actcatatat actttagatt  3780
gatttaaaac ttcattttta atttaaaagg atctaggtga agatcctttt tgataatctc  3840
atgaccaaaa tcccttaacg tgagttttcg ttccactgag cgtcagaccc cgtagaaaag  3900
atcaaaggat cttcttgaga tccttttttt ctgcgcgtaa tctgctgctt gcaaacaaaa  3960
aaaccaccgc taccagcggt ggtttgtttg ccggatcaag agctaccaac tctttttccg  4020
aaggtaactg gcttcagcag agcgcagata ccaaatactg ttcttctagt gtagccgtag  4080
ttaggccacc acttcaagaa ctctgtagca ccgcctacat acctcgctct gctaatcctg  4140
ttaccagtgg ctgctgccag tggcgataag tcgtgtctta ccgggttgga ctcaagacga  4200
tagttaccgg ataaggcgca gcggtcgggc tgaacggggg gttcgtgcac acagcccagc  4260
```

```
ttggagcgaa cgacctacac cgaactgaga tacctacagc gtgagctatg agaaagcgcc  4320
acgcttcccg aagggagaaa ggcggacagg tatccggtaa gcggcagggt cggaacagga  4380
gagcgcacga gggagcttcc agggggaaac gcctggtatc tttatagtcc tgtcgggttt  4440
cgccacctct gacttgagcg tcgatttttg tgatgctcgt caggggggcg gagcctatgg  4500
aaaaacgcca gcaacgcggc ctttttacgg ttcctggcct tttgctggcc ttttgctcac  4560
atgttctttc ctgcgttatc ccctgattct gtggataacc gtattaccgc ctttgagtga  4620
gctgataccg ctcgccgcag ccgaacgacc gagcgcagcg agtcagtgag cgaggaagcg  4680
gaagagcgcc caatacgcaa accgcctctc cccgcgcgtt ggccgattca ttaatgcagc  4740
tggcacgaca ggtttcccga ctggaaagcg ggcagtgagc gcaacgcaat taatgtgagt  4800
tagctcactc attaggcacc ccaggcttta cactttatgc ttccggctcg tatgttgtgt  4860
ggaattgtga gcggataaca atttcacaca ggaaacagct atgaccatga ttacgccaga  4920
tttaattaag g                                                        4931

SEQ ID NO: 32          moltype = DNA  length = 6031
FEATURE                Location/Qualifiers
misc_feature           1..6031
                       note = constructed sequence
source                 1..6031
                       mol_type = other DNA
                       organism = synthetic construct
SEQUENCE: 32
ctgcgcgctc gctcgctcac tgaggccgcc cgggcaaagc ccgggcgtcg ggcgaccttt  60
ggtcgcccgg cctcagtgag cgagcgagcg cgcagagagg gagtggccaa ctccatcact  120
aggggttcct tgtagttaat gattaacccg ccatgctact tatctacgta gccatgctct  180
aggaagatcg gaattcgccc ttaagctagg agttaatttt taaaaagcag tcaaaagtcc  240
aagtgccctt gcgagcattt actctctctg tttgctctgg ttaataatct caggagcaca  300
aacattcctt actagttcta ggagttaatt tttaaaaagc agtcaaaagt ccaagtgccc  360
ttgcgagcat ttactctctc tgtttgctct ggttaataat ctcaggagca caaacattcc  420
ttactagttc tagagcggcc gccagtgtgc tggaattcgg ctttttttagg gctggaagct  480
acctttgaca tcatttcctc tgcgaatgca tgtataattt ctacagaacc tattagaaag  540
gatcacccag cctctgcttt tgtacaactt tcccttaaaa aactgccaat ccccactgctg  600
tttggcccaa tagtgagaac tttttcctgc tgcctcttgg tgcttttgcc tatggcccct  660
attctgcctg ctgaagacac tcttgccagc atggacttaa acccctccag ctctgacaat  720
cctctttctc ttttgtttta catgaagggt ctggcagcca aagcaatcac tcaaagttca  780
aaccttatca ttttttgctt tgttcctctt ggccttggtt ttgtacatca gctttgaaaa  840
taccatccca gggttaatgc tggggttaat ttataactga gagtgctcta gttctgcaat  900
acaggacatg ctataaaaat ggaaagatgt tgctttctga gagatcagct tacttgtggt  960
accgagctcg gatcctgaga acttcagggt gagtctatgg gacccttgat gttttctttc  1020
cccttctttt ctatggttaa gttcatgtca taggaagggg agaagtaaca gggtacacat  1080
attgaccaaa tcagggtaat tttgcatttg taattttaaa aaatgctttc ttcttttaat  1140
atactttttt gtttatctta tttctaatac tttccctaat ctctttcttt cagggcaata  1200
atgatacaat gtatcatgcc tctttgcacc attctaaaga ataacagtga taatttctgg  1260
gttaaggcaa tagcaatatt tctgcatata aatatttctg catataaatt gtaactgatg  1320
taagaggttt catattgcta atagcagcta caatccagct accattctgc ttttatttta  1380
tggttgggat aaggctggat tattctgagt ccaagctagg ccctttttgct aatcatgttc  1440
atacctctta tcttcctccc acagctcctg ggcaacgtgc tggtctgtgt gctggcccat  1500
cactttggca aagaattgat ctcgaggccg ccaccatgtc cagcaaaggc tccgtggttc  1560
tggcctacag tggcggcctg gacacctcgt gcatcctcgt gtggctgaag gaacaaggct  1620
atgacgtcat tgcctatctg gccaacattg gccagaagga agacttcgag gaagccagga  1680
agaaggcact gaagcttggg gccaaaaagg tgttcattga ggatgtcagc agggagtttg  1740
tggaggagtt catctggccg gccatccagt ccagcgcact gtatgaggac cgctacctcc  1800
tgggcacctc tcttgccagg ccctgcatcg cccgcaaaca agtggaaatc gcccagcggg  1860
agggggccaa gtatgtgtcc cacggcgcca caggaaaggg gaacgatcag gtccggtttg  1920
agctcagctg ctactcactg gccccccaga taaaggtcat tgctccctgg aggatgcctg  1980
aattctacaa ccggttcaag ggccgcaatg acctgatgga gtacgcaaag caacacggga  2040
ttcccatccc ggtcactccc aagaacccgt ggagcatgga tgagaacctc atgcacatca  2100
gctacgaggc tggaatcctg gagaacccca agaaccaagc gcctccaggt ctctacacga  2160
agacccagga cccagccaaa gcccccaaca cccctgacat tctcgagatc gagttcaaaa  2220
aaggggtccc tgtgaaggtg accaacgtca aggatggcac cacccaccag acctccttgg  2280
agctcttcat gtacctgaac gaagtcgcgg gcaagcatgg cgtgggccgt attgacatcg  2340
tggagaaccg cttcattgga atgaagtccc gaggtatcta cgagacccca gcaggcacca  2400
tcctttacca cgctcattta gacatcgagg ccttcaccat ggaccgggaa gtgcgcaaaa  2460
tcaaacaagg cctgggcttg aaatttgctg agctggtgta taccggtttc tggcacagcc  2520
ctgagtgtga atttgtccgc cactgcatcg ccaagtccca ggagcgagtg gaagggaaag  2580
tgcaggtgtc cgtcctcaag ggccaggtgt acatcctcgg ccgggagtcc ccactgtctc  2640
tctacaatga ggagctggtg agcatgaacg tgcagggtga ttatgagcca actgatgcca  2700
ccgggttcat caacatcaat tccctcaggc tgaaggaata tcatcgtctc cagagcaagg  2760
tcactgccaa atgataagca tgcggatctg cctcgactgt gccttctagt tgccagccat  2820
ctgttgtttg cccctccccc gtgccttcct tgaccctgga aggtgccact cccactgtcc  2880
tttcctaata aaatgaggaa attgcatcgc attgtctgag taggtgtcat tctattctgg  2940
ggggtggggt ggggcaggac agcaaggggg aggattggga agacaatagc aggcatgctg  3000
gggactcgag ttaagggcga attcccgata aggatcttcc tagagcatgg ctacgtagat  3060
aagtagcatg gcgggttaat cattaactac aaggaacccc tagtgatgga gttggccact  3120
ccctctctgc gcgctcgctc gctcactgag gccgggcgac caaaggtcgc ccgacgcccg  3180
ggctttgccc gggcggcctc agtgagcgag cgagcgcgca gccttaatta acctaattca  3240
ctggccgtcg ttttacaacg tcgtgactgg gaaaaccctg gcgttaccca acttaatcgc  3300
cttgcagcac atcccccttt cgccagctgg cgtaatagcg aagaggcccg caccgatcgc  3360
ccttcccaac agttgcgcag cctgaatggc gaatgggacg cgccctgtag cggcgcatta  3420
agcgcggcgg gtgtggtggt tacgcgcagc gtgaccgcta cacttgccag cgccctagcg  3480
```

-continued

```
cccgctcctt tcgctttctt cccttccttt ctcgccacgt tcgccggctt tccccgtcaa  3540
gctctaaatc gggggctccc tttagggttc cgatttagtg ctttacggca cctcgacccc  3600
aaaaaacttg attagggtga tggttcacgt agtgggccat cgccctgata gacggttttt  3660
cgccctttga cgttggagtc cacgttcttt aatagtggac tcttgttcca aactggaaca  3720
acactcaacc ctatctcggt ctattctttt gatttataag ggattttgcc gatttcggcc  3780
tattggttaa aaaatgagct gatttaacaa aaatttaacg cgaattttaa caaaatatta  3840
acgcttacaa tttaggtggc acttttcggg gaaatgtgcg cggaacccct atttgtttat  3900
ttttctaaat acattcaaat atgtatccgc tcatgagaca ataaccctga taaatgcttc  3960
aataatattg aaaaaggaag agtatgagta ttcaacattt ccgtgtcgcc cttattccct  4020
tttttgcggc attttgcctt cctgtttttg ctcacccaga aacgctggtg aaagtaaaag  4080
atgctgaaga tcagttgggt gcacgagtgg gttacatcga actggatctc aacagcggta  4140
agatccttga gagttttcgc cccgaagaac gttttccaat gatgagcact tttaaagttc  4200
tgctatgtgg cgcggtatta tcccgtattg acgccgggca agagcaactc ggtcgccgca  4260
tacactattc tcagaatgac ttggttgagt actcaccagt cacagaaaag catcttacgg  4320
atggcatgac agtaagagaa ttatgcagtg ctgccataac catgagtgat aacactgcgg  4380
ccaacttact tctgacaacg atcggaggac cgaaggagct aaccgctttt ttgcacaaca  4440
tgggggatca tgtaactcgc cttgatcgtt gggaaccgga gctgaatgaa gccataccaa  4500
acgacgagcg tgacaccacg atgcctgtag caatggcaac aacgttgcgc aaactattaa  4560
ctggcgaact acttactcta gcttcccggc aacaattaat agactggatg gaggcggata  4620
aagttgcagg accacttctg cgctcggccc ttccggctgg ctggtttatt gctgataaat  4680
ctggagccgg tgagcgtggg tctcgcggta tcattgcagc actggggcca gatggtaagc  4740
cctcccgtat cgtagttatc tacacgacgg ggagtcaggc aactatggat gaacgaaata  4800
gacagatcgc tgagataggt gcctcactga ttaagcattg gtaactgtca gaccaagttt  4860
actcatatat actttagatt gatttaaaac ttcattttta atttaaaagg atctaggtga  4920
agatcctttt tgataatctc atgaccaaaa tcccttaacg tgagttttcg ttccactgag  4980
cgtcagaccc cgtagaaaag atcaaaggat cttcttgaga tccttttttt ctgcgcgtaa  5040
tctgctgctt gcaaacaaaa aaaccaccgc taccagcggt ggtttgtttg ccggatcaag  5100
agctaccaac tctttttccg aaggtaactg gcttcagcag agcgcagata ccaaatactg  5160
ttcttctagt gtagccgtag ttaggccacc acttcaagaa ctctgtagca ccgcctacat  5220
acctcgctct gctaatcctg ttaccagtgg ctgctgccag tggcgataag tcgtgtctta  5280
ccgggttgga ctcaagacga tagttaccgg ataaggcgca gcggtcgggc tgaacggggg  5340
gttcgtgcac acagcccagc ttggagcgaa cgacctacac cgaactgaga tacctacagc  5400
gtgagctatg agaaagcgcc acgcttcccg aagggagaaa ggcggacagg tatccggtaa  5460
gcggcagggt cggaacagga gagcgcacga gggagcttcc agggggaaac gcctggtatc  5520
tttatagtcc tgtcgggttt cgccacctct gacttgagcg tcgatttttg tgatgctcgt  5580
caggggggcg gagcctatgg aaaaacgcca gcaacgcggc ctttttacgg ttcctggcct  5640
tttgctggcc ttttgctcac atgttctttc ctgcgttatc ccctgattct gtggataacc  5700
gtattaccgc ctttgagtga gctgataccg ctcgccgcag ccgaacgacc gagcgcagcg  5760
agtcagtgag cgaggaagcg gaagagcgcc caatacgcaa accgcctctc cccgcgcgtt  5820
ggccgattca ttaatgcagc tggcacgaca ggtttcccga ctggaaagcg ggcagtgagc  5880
gcaacgcaat taatgtgagt tagctcactc attaggcacc ccaggcttta cactttatgc  5940
ttccggctcg tatgttgtgt ggaattgtga gcggataaca atttcacaca ggaaacagct  6000
atgaccatga ttacgccaga tttaattaag g                                6031

SEQ ID NO: 33          moltype = DNA  length = 6850
FEATURE                Location/Qualifiers
misc_feature           1..6850
                       note = constructed sequence
source                 1..6850
                       mol_type = other DNA
                       organism = synthetic construct
SEQUENCE: 33
ctgcgcgctc gctcgctcac tgaggccgcc cgggcaaagc ccgggcgtcg ggcgaccttt  60
ggtcgcccgg cctcagtgag cgagcgagcg cgcagagagg gagtggccaa ctccatcact  120
aggggttcct tgtagttaat gattaacccg ccatgctact tatctacgta gccatgctct  180
aggaagatcg gaattcgccc ttaagctagc ggatccaggt taatttttaa aaagcagtca  240
aaagtccaag tggcccttgg cagcatttac tctctctgtt tgctctggtt aataatctca  300
ggagcacaaa cattccagat ccaggttaat ttttaaaaag cagtcaaaag tccaagtggc  360
ccttggcagc atttactctc tctgtttgct ctggttaata atctcaggag cacaaacatt  420
ccagatccgg cgcgccaggg ctggaagcta cctttgacat catttcctct gcgaatgcat  480
gtataatttc tacagaacct attagaaagg atcacccagc ctctgctttt gtacaacttt  540
cccttaaaaa actgccaatt ccactgctgt ttggcccaat agtgagaact ttttcctgct  600
gcctcttggt gcttttgcct atggccccta ttctgcctgc tgaagacact cttgccagca  660
tggacttaaa cccctccagc tctgacaatc ctctttctct tttgttttac atgaagggtc  720
tggcagccaa agcaatcact caaagttcaa accttatcat tttttgcttt gttcctcttg  780
gccttggttt tgtacatcag ctttgaaaat accatcccag ggttaatgct ggggttaatt  840
tataactaag agtgctctag ttttgcaata caggacatgc tataaaaatg gaaagatgtt  900
gctttctgag agagcggccg cgtttgtttc ctttttttaaa atacattgag tatgcttgcc  960
ttttagatat agaaatatct gatgctgtct tcttcactaa attttgatta catgatttga  1020
cagcaatatt gaagagtcta acagccagca cgcaggttgg taagtactgg ttctttgtta  1080
gctaggtttt cttcttcttc atttttaaaa ctaaatagat cgacaatgct tatgatgcat  1140
ttatgtttaa taaacactgt tcagttcatg atttggtcat gtaattcctg ttagaaaaca  1200
ttcatctcct tggtttaaaa aaattaaaag tgggaaaaca aagaaatagc agaatatagt  1260
gaaaaaaaat aaccacatta tttttgtttg gacttaccac tttgaaatca aaatgggaaa  1320
caaaagcaca aacaatggcc ttatttacac aaaaagtctg attttaagat atatgacatt  1380
tcaaggtttc agaagtatgt aatgaggtgt gtctctaatt ttttaaatta tatatcttca  1440
atttaaagtt ttagttaaaa cataaagatt aacctttcat tagcaagctg ttagttatca  1500
ccaaagcttt tcatggatta ggaaaaaatc attttgtctc tatgtcaaac atcttggagt  1560
tgatatttgg ggaaacacaa tactcagttg agttccctag ggagaaaaag caagcttaag  1620
```

-continued

```
aattgacata aagagtagga agttagctaa tgcaacatat atcactttgt tttttcacaa  1680
ctacagtgac tttatgtatt tcccagagga aggcatacag ggaagaaatt atcccatttg  1740
gacaaacagc atgttctcac aggaagcatt tatcacactt acttgtcaac tttctagaat  1800
caaatctagt agctgacagt accaggatca ggggtgccaa ccctaagcac ccccagaaag  1860
ctgactggcc ctgtggttcc cactccagac atgatgtcag ctggaccata attaggcttc  1920
tgttcttcag gagacatttg ttcaaagtca tttgggcaac catattctga aaacagccca  1980
gccagggtga tggatcactt tgcaaagatc ctcaatgagc tattttcaag tgatgacaaa  2040
gtgtgaagtt aaccgctcat ttgagaactt tctttttcat ccaaagtaaa ttcaaatatg  2100
attagaaatc tgacctttta ttactggaat tctcttgact aaaagtaaaa ttgaatttta  2160
attcctaaat ctccatgtgt atacagtact gtgggaacat cacagatttt ggctccatgc  2220
cctaaagaga aattggcttt cagattattt ggattaaaaa caaagacttt cttaagagat  2280
gtaaaatttt catgatgttt tctttttgc taaaactaaa gaattattct tttacatttc  2340
agatggccgc caccatgagc agcaagggct ctgtggtgct ggcctactct ggcggcctgg  2400
acaccagctg tatcctcgtg tggctgaaag aacagggcta cgacgtgatc gcctacctgg  2460
ccaacatcgg ccagaaagag gacttcgagg aagcccggaa gaaggccctg aagctgggcg  2520
ccaagaaggt gttcatcgag gacgtgtccc gcgagttcgt ggaagagttc atctggcccg  2580
ccatccagag cagcgccctg tacgaggaca gatacctgct gggcaccagc ctggccagac  2640
cctgtatcgc ccggaaacag gtggaaatcg cccagcgcga gggcgccaaa tacgtgtctc  2700
acggcgccac cggcaagggc aacgaccagg tgcgctttga gctgagctgc tactccctgg  2760
ccccccagat caaagtgatc gccccttggc ggatgcccga gttctacaac cggttcaagg  2820
gccggaacga cctgatggaa tacgccaagc agcacggcat ccccatcccc gtgacccccca  2880
agaacccttg gagcatggac gagaacctga tgcacatcag ctacgaggcc ggcatcctgg  2940
aaaaccccaa gaatcaggcc cctcccggcc tgtacacaaa gacccaggac cctgccaagg  3000
cccccaacac ccccgacatt ctggaaatcg agttcaagaa aggcgtgccc gtgaaagtga  3060
ccaacgtgaa ggacggcacc acccaccaga cctccctgga actgttcatg tacctgaacg  3120
aggtggccgg caagcacggc gtgggcagaa tcgacatcgt ggaaaacaga ttcatcggca  3180
tgaagtcccg gggcatctac gagacaccag ccggcaccat cctgtaccac gcccacctgg  3240
atatcgaggc cttcaccatg gaccgggaag tgcggaagat caagcagggc ctgggcctga  3300
agttcgccga gctggtgtac acaggctttt ggcacagccc cgagtgcgag tttgtgcggc  3360
actgcattgc caagagccag gaacgggtgg aaggcaaggt gcaggtgtcc gtgctgaagg  3420
gccaggtgta cattctgggc agagagagcc ccctgagcct gtacaacgag gaactggtgt  3480
ctatgaacgt gcagggcgac tacgagccca ccgacgccac cggcttcatc aacatcaaca  3540
gcctgagact gaaagagtac caccggctgc agtccaaagt gaccgccaag tgataagcat  3600
gcggatctgc ctcgactgtg ccttctagtt gccagccatc tgttgtttgc ccctcccccg  3660
tgccttcctt gaccctggaa ggtgccactc ccactgtcct ttcctaataa aatgaggaaa  3720
ttgcatcgca ttgtctgagt aggtgtcatt ctattctggg gggtggggtg gggcaggaca  3780
gcaaggggga ggattgggaa gacaatagca ggcatgctgg ggactcgagt taagggcgaa  3840
ttcccgataa ggatcttcct agagcatggc tacgtagata agtagcatgg cgggttaatc  3900
attaactaca aggaacccct agtgatggag ttggccactc cctctctgcg cgctcgctcg  3960
ctcactgagg ccgggcgacc aaaggtcgcc cgacgcccgg gctttgcccg ggcggcctca  4020
gtgagcgagc gagcgcgcag ccttaattaa cctaattcac tggccgtcgt tttacaacgt  4080
cgtgactggg aaaaccctgg cgttacccaa cttaatcgcc ttgcagcaca tccccctttc  4140
gccagctggc gtaatagcga agaggcccgc accgatcgcc cttcccaaca gttgcgcagc  4200
ctgaatggcg aatgggacgc gccctgtagc ggcgcattaa gcgcggcggg tgtggtggtt  4260
acgcgcagcg tgaccgctac acttgccagc gccctagcgc ccgctccttt cgctttcttc  4320
ccttcctttc tcgccacgtt cgccggcttt ccccgtcaag ctctaaatcg ggggctccct  4380
ttagggttcc gatttagtgc tttacggcac ctcgacccca aaaaacttga ttagggtgat  4440
ggttcacgta gtgggccatc gccctgatag acggtttttc gccctttgac gttggagtcc  4500
acgttcttta atagtggact cttgttccaa actggaacaa cactcaaccc tatctcggtc  4560
tattcttttg atttataagg gattttgccg atttcggcct attggttaaa aaatgagctg  4620
atttaacaaa aatttaacgc gaattttaac aaaatattaa cgcttacaat ttaggtggca  4680
cttttcgggg aaatgtgcgc ggaaccccta tttgtttatt tttctaaata cattcaaata  4740
tgtatccgct catgagacaa taaccctgat aaatgcttca ataatattga aaaaggaaga  4800
gtatgagtat tcaacatttc cgtgtcgccc ttattccctt ttttgcggca ttttgccttc  4860
ctgtttttgc tcacccagaa acgctggtga aagtaaaaga tgctgaagat cagttgggtg  4920
cacgagtggg ttacatcgaa ctggatctca acagcggtaa gatccttgag agttttcgcc  4980
ccgaagaacg ttttccaatg atgagcactt ttaaagttct gctatgtggc gcggtattat  5040
cccgtattga cgccgggcaa gagcaactcg gtcgccgcat acactattct cagaatgact  5100
tggttgagta ctcaccagtc acagaaaagc atcttacgga tggcatgaca gtaagagaat  5160
tatgcagtgc tgccataacc atgagtgata acactgcggc caacttactt ctgacaacga  5220
tcggaggacc gaaggagcta accgcttttt tgcacaacat gggggatcat gtaactcgcc  5280
ttgatcgttg ggaaccggag ctgaatgaag ccataccaaa cgacgagcgt gacaccacga  5340
tgcctgtagc aatggcaaca acgttgcgca aactattaac tggcgaacta cttactctag  5400
cttcccggca acaattaata gactggatgg aggcggataa agttgcagga ccacttctgc  5460
gctcggccct tccggctggc tggtttattg ctgataaatc tggagccggt gagcgtgggt  5520
ctcgcggtat cattgcagca ctggggccag atggtaagcc ctcccgtatc gtagttatct  5580
acacgacggg gagtcaggca actatggatg aacgaaatag acagatcgct gagataggtg  5640
cctcactgat taagcattgg taactgtcag accaagttta ctcatatata ctttagattg  5700
atttaaaact tcatttttaa tttaaaagga tctaggtgaa gatccttttt gataatctca  5760
tgaccaaaat cccttaacgt gagttttcgt tccactgagc gtcagacccc gtagaaaaga  5820
tcaaaggatc ttcttgagat cctttttttc tgcgcgtaat ctgctgcttg caaacaaaaa  5880
aaccaccgct accagcggtg gtttgtttgc cggatcaaga gctaccaact ctttttccga  5940
aggtaactgg cttcagcaga gcgcagatac caaatactgt tcttctagtg tagccgtagt  6000
taggccacca cttcaagaac tctgtagcac cgcctacata cctcgctctg ctaatcctgt  6060
taccagtggc tgctgccagt ggcgataagt cgtgtcttac cgggttggac tcaagacgat  6120
agttaccgga taaggcgcag cggtcgggct gaacgggggg ttcgtgcaca cagcccagct  6180
tggagcgaac gacctacacc gaactgagat acctacagcg tgagctatga gaaagcgcca  6240
cgcttcccga agggagaaag gcggacaggt atccggtaag cggcagggtc ggaacaggag  6300
agcgcacgag ggagcttcca gggggaaacg cctggtatct ttatagtcct gtcgggtttc  6360
```

-continued

```
gccacctctg acttgagcgt cgatttttgt gatgctcgtc aggggggcgg agcctatgga  6420
aaaacgccag caacgcggcc tttttacggt tcctggcctt ttgctggcct tttgctcaca  6480
tgttctttcc tgcgttatcc cctgattctg tggataaccg tattaccgcc tttgagtgag  6540
ctgataccgc tcgccgcagc cgaacgaccg agcgcagcga gtcagtgagc gaggaagcgg  6600
aagagcgccc aatacgcaaa ccgcctctcc ccgcgcgttg gccgattcat taatgcagct  6660
ggcacgacag gtttcccgac tggaaagcgg gcagtgagcg caacgcaatt aatgtgagtt  6720
agctcactca ttaggcaccc caggctttac actttatgct tccggctcgt atgttgtgtg  6780
gaattgtgag cggataacaa tttcacacag gaaacagcta tgaccatgat tacgccagat  6840
ttaattaagg                                                        6850

SEQ ID NO: 34          moltype = DNA  length = 5608
FEATURE                Location/Qualifiers
misc_feature           1..5608
                       note = constructed sequence
source                 1..5608
                       mol_type = other DNA
                       organism = synthetic construct
SEQUENCE: 34
ctgcgcgctc gctcgctcac tgaggccgcc cgggcaaagc ccgggcgtcg ggcgaccttt  60
ggtcgcccgg cctcagtgag cgagcgagcg cgcagagagg gagtggccaa ctccatcact  120
aggggttcct tgtagttaat gattaacccg ccatgctact tatctacgta gccatgctct  180
aggaagatcg gaattcgccc ttaagctacc tcgtgatcgc ccggcccctg ttcaaacatg  240
tcctaatact ctgtctctgc aagggtcatc agtagttttc catcttactc aacatcctcc  300
cagtggaatt catttcatag aacgaatgtt ccgatgctct aatctctcta gacaaggttc  360
atatttgtat gggttactta ttctctcttt gttgactaag tcaataatca gaatcagcag  420
gtttgcagtc agattggcag ggataagcag cctagctcag gagaagtgag tataaaagcc  480
ccaggctggg agcagccatc agcggccgat ctagcttact tgtggtacca gctcggatcc  540
tgagaacttc agggtgagtc tatgggaccc ttgatgtttt ctttcccctt cttttctatg  600
gttaagttca tgtcatagga aggggagaag taacagggta cacatattga ccaaatcagg  660
gtaattttgc atttgtaatt ttaaaaaatg ctttcttctt ttaatatact tttttgttta  720
tcttatttct aatactttcc ctaatctctt tctttcaggg caataatgat acaatgtatc  780
atgcctcttt gcaccattct aaagaataac agtgataatt tctgggttaa ggcaatagca  840
atatttctgc atataaatat ttctgcatat aaattgtaac tgatgtaaga ggtttcatat  900
tgctaatagc agctacaatc cagctaccat tctgctttta ttttatggtt gggataaggc  960
tggattattc tgagtccaag ctaggccctt ttgctaatca tgttcatacc tcttatcttc  1020
ctcccacagc tcctgggcaa cgtgctggtc tgtgtgctgg cccatcactt tggcaaagaa  1080
ttgatctcga gtaactgaag gcggccgcca ccatgtccag caaaggctcc gtggttctgg  1140
cctacagtgg cggcctggac acctcgtgca tcctcgtgtg gctgaaggaa caaggctatg  1200
acgtcattgc ctatctggcc aacattggcc agaaggaaga cttcgaggaa gccaggaaga  1260
aggcactgaa gcttggggcc aaaaaggtgt tcattgagga tgtcagcagg gagtttgtgg  1320
aggagttcat ctggccggcc atccagtcca gcgcactgta tgaggaccgc tacctcctgg  1380
gcacctctct tgccaggccc tgcatcgccc gcaaacaagt ggaaatcgcc cagcgggagg  1440
gggccaagta tgtgtcccac ggcgccacag gaaaggggaa cgatcaggtc cggtttgagc  1500
tcagctgcta ctcactggcc ccccagataa aggtcattgc tccctggagg atgcctgaat  1560
tctacaaccg gttcaagggc cgcaatgacc tgatggagta cgcaaagcaa cacgggattc  1620
ccatcccggt cactcccaag aacccgtgga gcatggatga gaacctcatg cacatcagct  1680
acgaggctgg aatcctggag aaccccaaga accaagcgcc tccaggtctc tacacgaaga  1740
cccaggaccc agccaaagcc cccaacaccc ctgacattct cgagatcgag ttcaaaaaag  1800
gggtccctgt gaaggtgacc aacgtcaagg atggcaccac ccaccagacc tccttggagc  1860
tcttcatgta cctgaacgaa gtcgcgggca agcatggcgt gggccgtatt gacatcgtgg  1920
agaaccgctt cattggaatg aagtcccgag gtatctacga gaccccagca ggcaccatcc  1980
tttaccacgc tcatttagac atcgaggcct tcaccatgga ccgggaagtg cgcaaaatca  2040
aacaaggcct gggcttgaaa tttgctgagc tggtgtatac cggtttctgg cacagccctg  2100
agtgtgaatt tgtccgccac tgcatcgcca agtcccagga gcgagtggaa gggaaagtgc  2160
aggtgtccgt cctcaagggc caggtgtaca tcctcggccg ggagtcccca ctgtctctct  2220
acaatgagga gctggtgagc atgaacgtgc agggtgatta tgagccaact gatgccaccg  2280
ggttcatcaa catcaattcc ctcaggctga aggaatatca tcgtctccag agcaaggtca  2340
ctgccaaatg ataagcatgc ggatctgcct cgactgtgcc ttctagttgc cagccatctg  2400
ttgtttgccc ctcccccgtg ccttccttga ccctggaagg tgccactccc actgtccttt  2460
cctaataaaa tgaggaaatt gcatcgcatt gtctgagtag gtgtcattct attctggggg  2520
gtggggtggg gcaggacagc aagggggagg attgggaaga caatagcagg catgctgggg  2580
actcgagtta agggcgaatt cccgataagg atcttcctag agcatggcta cgtagataag  2640
tagcatggcg ggttaatcat taactacaag gaacccctag tgatggagtt ggccactccc  2700
tctctgcgcg ctcgctcgct cactgaggcc gggcgaccaa aggtcgcccg acgcccgggc  2760
tttgcccggg cggcctcagt gagcgagcga gcgcgcagcc ttaattaacc taattcactg  2820
gccgtcgttt tacaacgtcg tgactgggaa aaccctggcg ttacccaact taatcgcctt  2880
gcagcacatc ccccttttcgc cagctggcgt aatagcgaag aggcccgcac cgatcgccct  2940
tcccaacagt tgcgcagcct gaatggcgaa tgggacgcgc cctgtagcgg cgcattaagc  3000
gcggcgggtg tggtggttac gcgcagcgtg accgctacac ttgccagcgc cctagcgccc  3060
gctcctttcg ctttcttccc ttcctttctc gccacgttcg ccggctttcc ccgtcaagct  3120
ctaaatcggg ggctcccttt agggttccga tttagtgctt tacggcacct cgaccccaaa  3180
aaacttgatt agggtgatgg ttcacgtagt gggccatcgc cctgatagac ggtttttcgc  3240
cctttgacgt tggagtccac gttctttaat agtggactct tgttccaaac tggaacaaca  3300
ctcaacccta tctcggtcta ttcttttgat ttataaggga ttttgccgat ttcggcctat  3360
tggttaaaaa atgagctgat ttaacaaaaa tttaacgcga attttaacaa aatattaacg  3420
cttacaattt aggtggcact tttcggggaa atgtgcgcgg aacccctatt tgtttatttt  3480
tctaaataca ttcaaatatg tatccgctca tgagacaata accctgataa atgcttcaat  3540
aatattgaaa aaggaagagt atgagtattc aacatttccg tgtcgccctt attccctttt  3600
ttgcggcatt ttgccttcct gtttttgctc acccagaaac gctggtgaaa gtaaaagatg  3660
```

```
ctgaagatca gttgggtgca cgagtgggtt acatcgaact ggatctcaac agcggtaaga  3720
tccttgagag ttttcgcccc gaagaacgtt ttccaatgat gagcactttt aaagttctgc  3780
tatgtggcgc ggtattatcc cgtattgacg ccgggcaaga gcaactcggt cgccgcatac  3840
actattctca gaatgacttg gttgagtact caccagtcac agaaaagcat cttacggatg  3900
gcatgacagt aagagaatta tgcagtgctg ccataaccat gagtgataac actgcggcca  3960
acttacttct gacaacgatc ggaggaccga aggagctaac cgcttttttg cacaacatgg  4020
gggatcatgt aactcgcctt gatcgttggg aaccggagct gaatgaagcc ataccaaacg  4080
acgagcgtga caccacgatg cctgtagcaa tggcaacaac gttgcgcaaa ctattaactg  4140
gcgaactact tactctagct tcccggcaac aattaataga ctggatggag gcggataaag  4200
ttgcaggacc acttctgcgc tcggcccttc cggctggctg gtttattgct gataaatctg  4260
gagccggtga gcgtgggtct cgcggtatca ttgcagcact ggggccagat ggtaagccct  4320
cccgtatcgt agttatctac acgacgggga gtcaggcaac tatggatgaa cgaaatagac  4380
agatcgctga gataggtgcc tcactgatta agcattggta actgtcagac caagtttact  4440
catatatact ttagattgat ttaaaacttc atttttaatt taaaaggatc taggtgaaga  4500
tcctttttga taatctcatg accaaaatcc cttaacgtga gttttcgttc cactgagcgt  4560
cagaccccgt agaaaagatc aaaggatctt cttgagatcc tttttttctg cgcgtaatct  4620
gctgcttgca aacaaaaaaa ccaccgctac cagcggtggt ttgtttgccg gatcaagagc  4680
taccaactct ttttccgaag gtaactggct tcagcagagc gcagatacca aatactgttc  4740
ttctagtgta gccgtagtta ggccaccact tcaagaactc tgtagcaccg cctacatacc  4800
tcgctctgct aatcctgtta ccagtggctg ctgccagtgg cgataagtcg tgtcttaccg  4860
ggttggactc aagacgatag ttaccggata aggcgcagcg gtcgggctga acggggggtt  4920
cgtgcacaca gcccagcttg gagcgaacga cctacaccga actgagatac ctacagcgtg  4980
agctatgaga aagcgccacg cttcccgaag ggagaaaggc ggacaggtat ccggtaagcg  5040
gcagggtcgg aacaggagag cgcacgaggg agcttccagg gggaaacgcc tggtatcttt  5100
atagtcctgt cgggtttcgc cacctctgac ttgagcgtcg atttttgtga tgctcgtcag  5160
gggggcggag cctatggaaa aacgccagca acgcggcctt tttacggttc ctggcctttt  5220
gctggccttt tgctcacatg ttctttcctg cgttatcccc tgattctgtg gataaccgta  5280
ttaccgcctt tgagtgagct gataccgctc gccgcagccg aacgaccgag cgcagcgagt  5340
cagtgagcga ggaagcggaa gagcgcccaa tacgcaaacc gcctctcccc gcgcgttggc  5400
cgattcatta atgcagctgg cacgacaggt ttcccgactg gaaagcgggc agtgagcgca  5460
acgcaattaa tgtgagttag ctcactcatt aggcacccca ggctttacac tttatgcttc  5520
cggctcgtat gttgtgtgga attgtgagcg gataacaatt tcacacagga aacagctatg  5580
accatgatta cgccagattt aattaagg                                    5608

SEQ ID NO: 35          moltype = DNA  length = 5876
FEATURE                Location/Qualifiers
misc_feature           1..5876
                       note = constructed sequence
source                 1..5876
                       mol_type = other DNA
                       organism = synthetic construct
SEQUENCE: 35
ctgcgcgctc gctcgctcac tgaggccgcc cgggcaaagc ccgggcgtcg ggcgaccttt  60
ggtcgcccgg cctcagtgag cgagcgagcg cgcagagagg gagtggccaa ctccatcact  120
aggggttcct tgtagttaat gattaacccg ccatgctact tatctacgta gccatgctct  180
aggaagatcg gaattcgccc ttaagctagc cgctgacaag gctcagaggc acacaggagt  240
ttctgggctc accctgcccc cttccaaccc ctcagttccc atcctccagc agctgtttgt  300
gtgctgcctc tgaagtccac actgaacaaa cttcagccta ctcatgtccc taaaatgggc  360
aaacattgca agcagcaaac agcaaacaca cagccctccc tgcctgctga ccttggagct  420
ggggcagagg tcagagacct ctctgggccc atgccacctc caacatccac tcgacccctt  480
ggaatttcgg tggagaggag cagaggttgt cctggcgtgg tttaggtagt gtgagaggga  540
gatccggcgc gcctggacac aggacgctgt ggtttctgag ccagggggcg actcagatcc  600
cagccagtgg acttagcccc tgtttgctcc tccgataact ggggtgacct tggttaatat  660
tcaccagcag cctcccccgt tgcccctctg gatccactgc ttaaatacgg acgaggacag  720
ggccctgtct cctcagcttc aggcaccacc actgacctgg gacagtgaat agcgagatct  780
agcttacttg tggtaccagc tcggatcctg agaacttcag ggtgagtcta tgggaccctt  840
gatgttttct ttccccttct tttctatggt taagttcatg tcataggaag gggagaagta  900
acagggtaca catattgacc aaatcagggt aattttgcat ttgtaatttt aaaaaatgct  960
ttcttctttt aatatacttt tttgtttatc ttatttctaa tactttccct aatctctttc  1020
tttcagggca ataatgatac aatgtatcat gcctctttgc accattctaa agaataacag  1080
tgataatttc tgggttaagg caatagcaat atttctgcat ataaatattt ctgcatataa  1140
attgtaactg atgtaagagg tttcatattg ctaatagcag ctacaatcca gctaccattc  1200
tgcttttatt ttatggttgg gataaggctg gattattctg agtccaagct aggccctttt  1260
gctaatcatg ttcatacctc ttatcttcct cccacagctc ctgggcaacg tgctggtctg  1320
tgtgctggcc catcactttg gcaaagaatt gatctcgagt aactgaaggc ggccgccacc  1380
atgtccagca aaggctccgt ggttctggcc tacagtggcg gcctggacac ctcgtgcatc  1440
ctcgtgtggc tgaaggaaca aggctatgac gtcattgcct atctggccaa cattggccag  1500
aaggaagact tcgaggaagc caggaagaag gcactgaagc ttggggccaa aaaggtgttc  1560
attgaggatg tcagcaggga gtttgtggag gagttcatct ggccggccat ccagtccagc  1620
gcactgtatg aggaccgcta cctcctgggc acctctcttg ccaggccctg catcgcccgc  1680
aaacaagtgg aaatcgccca gcgggagggg gccaagtatg tgtcccacgg cgccacagga  1740
aaggggaacg atcaggtccg gtttgagctc agctgctact cactggcccc ccagataaag  1800
gtcattgctc cctggaggat gcctgaattc tacaaccggt tcaagggccg caatgacctg  1860
atggagtacg caaagcaaca cgggattccc atcccggtca ctcccaagaa cccgtggagc  1920
atggatgaga acctcatgca catcagctac gaggctggaa tcctggagaa ccccaagaac  1980
caagcgcctc caggtctcta cacgaagacc caggacccag ccaaagcccc caacacccct  2040
gacattctcg agatcgagtt caaaaaaggg gtccctgtga aggtgaccaa cgtcaaggat  2100
ggcaccaccc accagacctc cttggagctc ttcatgtacc tgaacgaagt cgcgggcaag  2160
catggcgtgg gccgtattga catcgtggag aaccgcttca ttggaatgaa gtcccgaggt  2220
```

-continued

```
atctacgaga ccccagcagg caccatcctt taccacgctc atttagacat cgaggccttc  2280
accatggacc gggaagtgcg caaaatcaaa caaggcctgg gcttgaaatt tgctgagctg  2340
gtgtataccg gtttctggca cagccctgag tgtgaatttg tccgccactg catcgccaag  2400
tcccaggagc gagtggaagg gaaagtgcag gtgtccgtcc tcaagggcca ggtgtacatc  2460
ctcggccggg agtccccact gtctctctac aatgaggagc tggtgagcat gaacgtgcag  2520
ggtgattatg agccaactga tgccaccggg ttcatcaaca tcaattccct caggctgaag  2580
gaatatcatc gtctccagag caaggtcact gccaaatgat aagcatgcgg atctgcctcg  2640
actgtgcctt ctagttgcca gccatctgtt gtttgcccct cccccgtgcc ttccttgacc  2700
ctggaaggtg ccactcccac tgtcctttcc taataaaatg aggaaattgc atcgcattgt  2760
ctgagtaggt gtcattctat tctggggggt ggggtggggc aggacagcaa gggggaggat  2820
tgggaagaca atagcaggca tgctggggac tcgagttaag ggcgaattcc cgataaggat  2880
cttcctagag catggctacg tagataagta gcatggcggg ttaatcatta actacaagga  2940
acccctagtg atggagttgg ccactccctc tctgcgcgct cgctcgctca ctgaggccgg  3000
gcgaccaaag gtcgcccgac gcccgggctt tgcccgggcg gcctcagtga gcgagcgagc  3060
gcgcagcctt aattaaccta attcactggc cgtcgtttta caacgtcgtg actgggaaaa  3120
ccctggcgtt acccaactta atcgccttgc agcacatccc cctttcgcca gctggcgtaa  3180
tagcgaagag gcccgcaccg atcgcccttc ccaacagttg cgcagcctga atggcgaatg  3240
ggacgcgccc tgtagcggcg cattaagcgc ggcgggtgtg gtggttacgc gcagcgtgac  3300
cgctacactt gccagcgccc tagcgcccgc tcctttcgct ttcttccctt cctttctcgc  3360
cacgttcgcc ggctttcccc gtcaagctct aaatcggggg ctccctttag ggttccgatt  3420
tagtgcttta cggcacctcg accccaaaaa acttgattag ggtgatggtt cacgtagtgg  3480
gccatcgccc tgatagacgg tttttcgccc tttgacgttg gagtccacgt tctttaatag  3540
tggactcttg ttccaaactg gaacaacact caaccctatc tcggtctatt cttttgattt  3600
ataagggatt ttgccgattt cggcctattg gttaaaaaat gagctgattt aacaaaaatt  3660
taacgcgaat tttaacaaaa tattaacgct tacaatttag gtggcacttt tcggggaaat  3720
gtgcgcggaa cccctatttg tttatttttc taaatacatt caaatatgta tccgctcatg  3780
agacaataac cctgataaat gcttcaataa tattgaaaaa ggaagagtat gagtattcaa  3840
catttccgtg tcgcccttat tccctttttt gcggcatttt gccttcctgt ttttgctcac  3900
ccagaaacgc tggtgaaagt aaaagatgct gaagatcagt tgggtgcacg agtgggttac  3960
atcgaactgg atctcaacag cggtaagatc cttgagagtt ttcgccccga agaacgtttt  4020
ccaatgatga gcacttttaa agttctgcta tgtggcgcgg tattatcccg tattgacgcc  4080
gggcaagagc aactcggtcg ccgcatacac tattctcaga atgacttggt tgagtactca  4140
ccagtcacag aaaagcatct tacggatggc atgacagtaa gagaattatg cagtgctgcc  4200
ataaccatga gtgataacac tgcggccaac ttacttctga caacgatcgg aggaccgaag  4260
gagctaaccg cttttttgca caacatgggg gatcatgtaa ctcgccttga tcgttgggaa  4320
ccggagctga atgaagccat accaaacgac gagcgtgaca ccacgatgcc tgtagcaatg  4380
gcaacaacgt tgcgcaaact attaactggc gaactactta ctctagcttc ccggcaacaa  4440
ttaatagact ggatggaggc ggataaagtt gcaggaccac ttctgcgctc ggcccttccg  4500
gctggctggt ttattgctga taaatctgga gccggtgagc gtgggtctcg cggtatcatt  4560
gcagcactgg ggccagatgg taagccctcc cgtatcgtag ttatctacac gacggggagt  4620
caggcaacta tggatgaacg aaatagacag atcgctgaga taggtgcctc actgattaag  4680
cattggtaac tgtcagacca agtttactca tatatacttt agattgattt aaaacttcat  4740
ttttaattta aaaggatcta ggtgaagatc ctttttgata atctcatgac caaaatccct  4800
taacgtgagt tttcgttcca ctgagcgtca gaccccgtag aaaagatcaa aggatcttct  4860
tgagatcctt tttttctgcg cgtaatctgc tgcttgcaaa caaaaaaacc accgctacca  4920
gcggtggttt gtttgccgga tcaagagcta ccaactcttt ttccgaaggt aactggcttc  4980
agcagagcgc agataccaaa tactgttctt ctagtgtagc cgtagttagg ccaccacttc  5040
aagaactctg tagcaccgcc tacatacctc gctctgctaa tcctgttacc agtggctgct  5100
gccagtggcg ataagtcgtg tcttaccggg ttggactcaa gacgatagtt accggataag  5160
gcgcagcggt cgggctgaac ggggggttcg tgcacacagc ccagcttgga gcgaacgacc  5220
tacaccgaac tgagatacct acagcgtgag ctatgagaaa gcgccacgct tcccgaaggg  5280
agaaaggcgg acaggtatcc ggtaagcggc agggtcggaa caggagagcg cacgagggag  5340
cttccagggg gaaacgcctg gtatctttat agtcctgtcg ggtttcgcca cctctgactt  5400
gagcgtcgat ttttgtgatg ctcgtcaggg gggcggagcc tatggaaaaa cgccagcaac  5460
gcggcctttt tacggttcct ggccttttgc tggccttttg ctcacatgtt ctttcctgcg  5520
ttatcccctg attctgtgga taaccgtatt accgcctttg agtgagctga taccgctcgc  5580
cgcagccgaa cgaccgagcg cagcgagtca gtgagcgagg aagcggaaga gcgcccaata  5640
cgcaaaccgc ctctccccgc gcgttggccg attcattaat gcagctggca cgacaggttt  5700
cccgactgga aagcgggcag tgagcgcaac gcaattaatg tgagttagct cactcattag  5760
gcaccccagg ctttacactt tatgcttccg gctcgtatgt tgtgtggaat tgtgagcgga  5820
taacaatttc acacaggaaa cagctatgac catgattacg ccagatttaa ttaagg      5876
```

```
SEQ ID NO: 36          moltype = DNA  length = 4393
FEATURE                Location/Qualifiers
source                 1..4393
                       mol_type = genomic DNA
                       organism = adeno-associated virus 8
SEQUENCE: 36
cagagaggga gtggccaact ccatcactag gggtagcgcg aagcgcctcc cacgctgccg  60
cgtcagcgct gacgtaaatt acgtcatagg ggagtggtcc tgtattagct gtcacgtgag  120
tgcttttgcg gcattttgcg acaccacgtg gccatttgag gtatatatgg ccgagtgagc  180
gagcaggatc tccattttga ccgcgaaatt tgaacgagca gcagccatgc cgggcttcta  240
cgagatcgtg atcaaggtgc cgagcgacct ggacgagcac ctgccgggca tttctgactc  300
gtttgtgaac tgggtggccg agaaggaatg ggagctgccc ccggattctg acatggatcg  360
gaatctgatc gagcaggcac ccctgaccgt ggccgagaag ctgcagcgcg acttcctggt  420
ccaatggcgc cgcgtgagta aggccccgga ggccctcttc tttgttcagt tcgagaaggg  480
cgagagctac tttcacctgc acgttctggt cgagaccacg gggtcaagt ccatggtgct  540
aggccgcttc ctgagtcaga ttcgggaaaa gcttggtcca gaccatctac ccgcggggtc  600
gagccccacc ttgcccaact ggttcgcggt gaccaaagac gcggtaatgg cgccggcggg  660
```

-continued

```
ggggaacaag gtggtggacg agtgctacat ccccaactac ctcctgccca agactcagcc  720
cgagctgcag tgggcgtgga ctaacatgga ggagtatata agcgcgtgct tgaacctggc  780
cgagcgcaaa cggctcgtgg cgcagcacct gacccacgtc agccagacgc aggagcagaa  840
caaggagaat ctgaacccca attctgacgc gcccgtgatc aggtcaaaaa cctccgcgcg  900
ctatatggag ctggtcgggt ggctggtgga ccggggcatc acctccgaga agcagtggat  960
ccaggaggac caggcctcgt acatctcctt caacgccgcc tccaactcgc ggtcccagat 1020
caaggccgcg ctggacaatg ccggcaagat catggcgctg accaaatccg cgcccgacta 1080
cctggtgggg ccctcgctgc ccgcggacat tacccagaac cgcatctacc gcatcctcgc 1140
tctcaacggc tacgaccctg cctacgccgg ctccgtcttt ctcggctggg ctcagaaaaa 1200
gttcgggaaa cgcaacacca tctggctgtt tggacccgcc accaccggca agaccaacat 1260
tgcggaagcc atcgcccacg ccgtgccctt ctacggctgc gtcaactgga ccaatgagaa 1320
ctttcccttc aatgattgcg tcgacaagat ggtgatctgg tgggaggagg gcaagatgac 1380
ggccaaggtc gtggagtccg ccaaggccat tctcggcggc agcaaggtgc gcgtggacca 1440
aaagtgcaag tcgtccgccc agatcgaccc cacccccgtg atcgtcacct ccaacaccaa 1500
catgtgcgcc gtgattgacg ggaacagcac caccttcgag caccagcagc ctctccagga 1560
ccggatgttt aagttcgaac tcacccgccg tctggagcac gactttggca aggtgacaaa 1620
gcaggaagtc aaagagttct tccgctgggc cagtgatcac gtgaccgagg tggcgcatga 1680
gttttacgtc agaaagggcg gagccagcaa aagacccgcc cccgatgacg cggataaaag 1740
cgagcccaag cgggcctgcc cctcagtcgc ggatccatcg acgtcagacg cggaaggagc 1800
tccggtggac tttgccgaca ggtaccaaaa caaatgttct cgtcacgcgg gcatgcttca 1860
gatgctgttt ccctgcaaaa cgtgcgagag aatgaatcag aatttcaaca tttgcttcac 1920
acacggggtc agagactgct cagagtgttt ccccggcgtg tcagaatctc aaccggtcgt 1980
cagaaagagg acgtatcgga aactctgtgc gattcatcat ctgctggggc gggctcccga 2040
gattgcttgc tcggcctgcg atctggtcaa cgtggacctg gatgactgtg tttctgagca 2100
ataaatgact taaaccaggt atggctgccg atggttatct tccagattgg ctcgaggaca 2160
acctctctga gggcattcgc gagtggtggg cgctgaaacc tggagccccg aagcccaaag 2220
ccaaccagca aaagcaggac gacggccggg gtctggtgct tcctggctac aagtacctcg 2280
gacccttcaa cggactcgac aaggggagc ccgtcaacgc ggcggacgca gcggccctcg 2340
agcacgacaa ggcctacgac cagcagctgc aggcgggtga caatccgtac ctgcggtata 2400
accacgccga cgccgagttt caggagcgtc tgcaagaaga tacgtctttt gggggcaacc 2460
tcgggcgagc agtcttccag gccaagaagc gggttctcga acctctcggt ctggttgagg 2520
aaggcgctaa gacggctcct ggaaagaaga gaccggtaga gccatcaccc cagcgttctc 2580
cagactcctc tacgggcatc ggcaagaaag gccaacagcc cgccagaaaa agactcaatt 2640
ttggtcagac tggcgactca gagtcagttc cagaccctca acctctcgga gaacctccag 2700
cagcgccctc tggtgtggga cctaatacaa tggctgcagg cggtggcgca ccaatggcag 2760
acaataacga aggcgccgac ggagtgggta gttcctcggg aaattggcat tgcgattcca 2820
catggctggg cgacagagtc atcaccacca gcacccgaac ctgggccctg cccacctaca 2880
acaaccacct ctacaagcaa atctccaacg ggacatcggg aggagccacc aacgacaaca 2940
cctacttcgg ctacagcacc ccctgggggt attttgactt taacagattc cactgccact 3000
tttcaccacg tgactggcag cgactcatca acaacaactg gggattccgg cccaagagac 3060
tcagcttcaa gctcttcaac atccaggtca aggaggtcac gcagaatgaa ggcaccaaga 3120
ccatcgccaa taacctcacc agcaccatcc aggtgtttac ggactcggag taccagctgc 3180
cgtacgttct cggctctgcc caccagggct gcctgcctcc gttcccggcg gacgtgttca 3240
tgattcccca gtacggctac ctaacactca acaacggtag tcaggccgtg ggacgctcct 3300
ccttctactg cctggaatac tttccttcgc agatgctgag aaccggcaac aacttccagt 3360
ttacttacac cttcgaggac gtgcctttcc acagcagcta cgcccacagc cagagcttgg 3420
accggctgat gaatcctctg attgaccagt acctgtacta cttgtctcgg actcaaacaa 3480
caggaggcac ggcaaatacg cagactctgg gcttcagcca aggtgggcct aatacaatgg 3540
ccaatcaggc aaagaactgg ctgccaggac cctgttaccg ccaacaacgc gtctcaacga 3600
caaccgggca aaacaacaat agcaactttg cctggactgc tgggaccaaa taccatctga 3660
atggaagaaa ttcattggct aatcctggca tcgctatggc aacacacaaa gacgacgagg 3720
agcgtttttt tcccagtaac gggatcctga tttttggcaa acaaaatgct gccagagaca 3780
atgcggatta cagcgatgtc atgctcacca gcgaggaaga aatcaaaacc actaaccctg 3840
tggctacaga ggaatacggt atcgtggcag ataacttgca gcagcaaaac acggctcctc 3900
aaattggaac tgtcaacagc caggggggcct tacccggtat ggtctggcag aaccgggacg 3960
tgtacctgca gggtcccatc tggccaaga ttcctcacac ggacggcaac ttccacccgt 4020
ctccgctgat gggcggcttt ggcctgaaac atcctccgcc tcagatcctg atcaagaaca 4080
cgcctgtacc tgcggatcct ccgaccacct tcaaccagtc aaagctgaac tctttcatca 4140
cgcaatacag caccggacag gtcagcgtgg aaattgaatg ggagctgcag aaggaaaaca 4200
gcaagcgctg gaaccccgag atccagtaca cctccaacta ctacaaatct acaagtgtgg 4260
actttgctgt taatacagaa ggcgtgtact ctgaaccccg ccccattggc acccgttacc 4320
tcacccgtaa tctgtaattg cctgttaatc aataaaccgg ttgattcgtt tcagttgaac 4380
tttggtctct gcg                                                    4393
```